United States Patent [19]

Hasegawa et al.

[11] Patent Number: 5,380,832
[45] Date of Patent: Jan. 10, 1995

[54] GANGLIOSIDE GM3 ANALOGS

[75] Inventors: Akira Hasegawa, 1735-160 Ohkurayama; Makoto Kiso, both of Gifu, Japan

[73] Assignees: The Nisshin Oil Mills, Ltd., Tokyo; Akira Hasegawa, Gifu, both of Japan

[21] Appl. No.: 243,525

[22] Filed: May 16, 1994

Related U.S. Application Data

[63] Continuation of Ser. No. 846,390, Mar. 5, 1992, abandoned.

[30] Foreign Application Priority Data

Mar. 29, 1991 [JP] Japan .................................. 3-089171

[51] Int. Cl.$^6$ ...................... C07H 15/10; A61K 31/72
[52] U.S. Cl. .................................. 536/17.9; 536/17.2; 536/53; 536/55; 536/55.1; 536/119
[58] Field of Search .................. 536/17.2, 17.9, 53, 536/55, 55.1, 119; 514/25

[56] References Cited

U.S. PATENT DOCUMENTS 4,918,170  4/1990  Hasegawa et al. ................... 536/1.1
4,990,603  2/1991  Ogawa et al. ...................... 536/17.4

FOREIGN PATENT DOCUMENTS 1-290689  11/1989  Japan .
 2-78694   3/1990  Japan .
 3-101691  4/1991  Japan .
 3-261796 11/1991  Japan .

OTHER PUBLICATIONS

Science of Life, vol. 38, No. 4, 1987, pp. 332–339, Yasuo Suzuki.
Experimental Medicine, vol. 6, No. 11, 1988, pp. 21(1037)–27(1043), Shuichi Tsuji.
(List continued on next page.)

Primary Examiner—John W. Rollins
Assistant Examiner—Kathleen Kahler Fonda
Attorney, Agent, or Firm—Oblon, Spivak, McClelland, Maier, & Neustadt

[57] ABSTRACT

Disclosed are ganglioside GM3 analogs represented by the formula

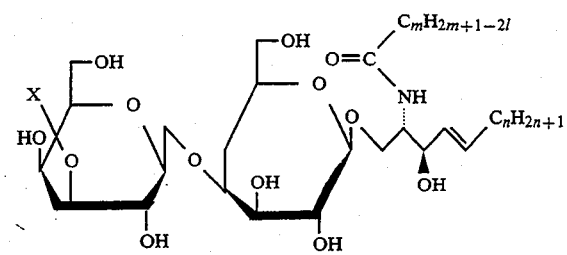

in which X represents a radical of the following formula

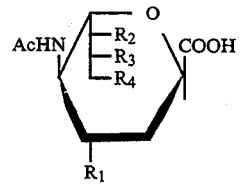

wherein at least one of $R_1$, $R_2$, $R_3$ and $R_4$ is hydrogen and the remainder is hydroxyl;

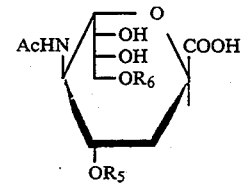

wherein at least one of $R_5$ and $R_6$ is hydrogen and the remainder is methyl;

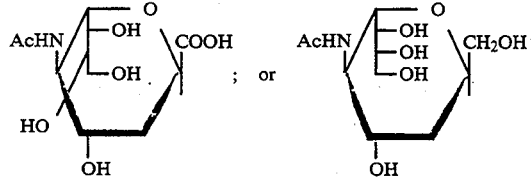

wherein m is an integer of 15 to 25, l is an integer of 0 to 3, n is an integer of 11 to 15 and Ac represents acetyl. The ganglioside GM3 analogs are expected to possess an inhibitory activity for influenza virus.

3 Claims, No Drawings

OTHER PUBLICATIONS

Neurochemistry International, vol. 5, No. 5, 1983, pp. 507–537.

Cell Biology Monographs, vol. 10, Sailic Acids, R. Schauer.

Biochemistry, vol. 62, No. 4, 1990, pp. 231–260. Yasuo Suzuki.

Nature, vol. 333, Jun. 1988, pp. 426–431, W. Weis, et al., "Structure of the Influenza Virus Haemagglutinin Complexed With Its Receptor, Sialic Acid".

Nature, vol. 303, May 5, 1983, pp. 41–45, P. M. Colman et al., "Structure of the Catalytic And Antigenic Sites in Influenza Virus Neuraminidase".

Glycoconjugate J, 7, 1990, pp. 349–357, Y. Suzuki, et al., "New Ganglioside Analogs That Inhibit Influenza Virus Sialidase".

Trends in Glycoscience and Glycotechnology, vol. 2, No. 4, Mar. 2, 1990, Y. Suzuki, pp. 112–118, "Biological Role of $Q$-Acetylated Sialic Acid".

T.I.B.S., 10, Sep. 1985, pp. 357–360, R. Schauer, "Sialic Acids and Their Role as Biological Masks".

Schauer, Roland *TIBS*, Sep. 1985, pp. 357–360.

Saito et al; J. Biol. Chem. 254(16): 7845–7854 (1979).

Sander-Wewer et al; Chemical Abstracts 98: 49369q (1983).

Klein et al; Eur. J. Biochem. 167: 417–424 (1987).

Hachida et al; Chemical Abstracts 113: 224285m (Dec. 17, 1990).

Hasegawa et al; J. Carbohydr. Chem. 11(1): 95–116 (Jan., 1992).

GANGLIOSIDE GM3 ANALOGS

This application is a continuation of application Ser. No. 07/846,390, filed on Mar. 5, 1992, now abandoned.

FIELD OF THE INVENTION

This invention relates to ganglioside GM$_3$ analogs containing the modified portion of sialic acid which is known as a constituent of gangliosides which are a physiologically active glycolipid participating in various biological phenomena.

BACKGROUND OF THE INVENTION

Ganglioside is the generic term for glycosphingolipids containing sialic acids, which are an amphiphilic molecular species consisting of a hydrophilic saccharide moiety and a hydrophobic ceramide moiety. They are ubiquitous constituents of mammalian cells.

Gangliosides play a fundamental role as an acceptor for a number of biological ligands such as various cytotoxins (cholera vibrio, tetanus bacillus, *Clostridium botulinum*, *Vibrio parahaemolyticus*, Staphylococcus, etc.), hormones (thyrotrophic hormone, luteinizing hormone), interferons, neurotransmitters (serotonin, noradrenalin, dopamine, histamine) and influenza viruses.

On the surface of influenza virus membrane occur hemagglutinin [W. Weis et al., Nature, Vol. 333, 426 (1988)] and neuraminidase [P. M. Colman et al., Nature, Vol. 303, 41 (1983)], the former specifically recognizing sialic acid-containing saccharide chains. They play an important role in adsorption on and invasion into animal cells of influenza viruses, which are important constituents in the mechanism of the adsorption and invasion when viewed from the host with respect to prevention of viral infection.

We have investigated the effects of various ganglioside analogs on activity of influenza virus neuraminidases with interesting results [Y. Suzuki et al., Glycoconjugate J., 7 (1990)].

Such substances strongly binding to influenza virus neuraminidases but not a substrate for the enzymes may be very useful for the analysis of the three-dimensional structure of activity center of the enzyme, leading to an approach for prevention of viral infections.

Partial acetylation of sialic acids may protect them against the action of sialidases, and may also influence the antigenicity of human melanoma cells and of bacterial polysaccharides. It has also been reported that the acetylatoin of sialic acids can be necessary for the binding of viruses [Y. Suzuki, TRENDS IN GLYCOSCIENCE AND GLYCOTECHNOLOGY, Vol. 2, 4, 112 (1990)].

Sialic acid is a generic term for a member of neuraminic acid derivatives, which contains acetyl and glycolyl groups as substituent on the amino group and acetyl, lactyl, phosphate, sulfate, methyl or other groups as substituent on the hydroxyl groups. Presently, approximately 30 species of sialic acid have occurred and determined for structure.

As principal functions of sialic acids are mentioned, for example, (1) providing glycoconjugates and cell membranes with negative charge, (2) influence upon the conformation of glycolipids or glycoproteins, (3) information transmission and (4) masking action on the antigenic site [R. Shauer, T.I.B.S., 10, 357 (1985)]. Role of sialic acids will attract increasing interests in the future.

As described above, gangliosides take part in a variety of biological phenomena. A constituent of the gangliosides, sialic acids are considered to have a great influence upon the occurrence of the activities.

In order to elucidate the effects of the structure of sialic acids upon the occurrence of the activities of gangliosides it is necessary to prepare a variety of gangliosides containing a chemically modified sialic acid. Elucidation of the function of gangliosides on a molecular level would be accomplished using such modified compounds.

SUMMARY OF THE INVENTION

An object of the invention is to provide new ganglioside GM$_3$ analogs having a wide variety of physiological activities and expected inhibitory activity for influenza virus.

Another object of the invention is to provide a new class of ganglioside GM$_3$ analogs.

In accordance with the present invention, there is provided a ganglioside GM$_3$ analog represented by the formula

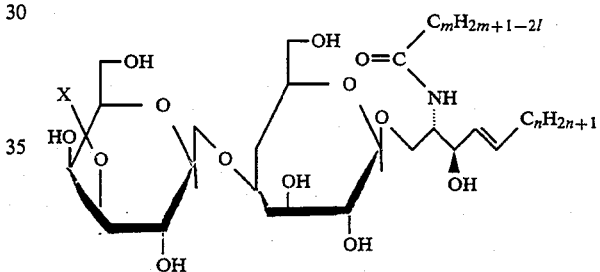

in which X represents a radical of the following formula

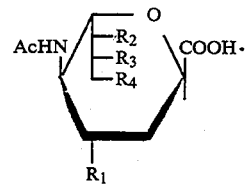

wherein at least one of R$_1$, R$_2$, R$_3$ and R$_4$ is hydrogen and the remainder is hydroxyl;

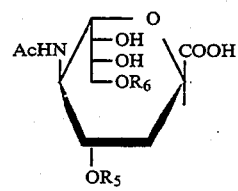

wherein at least one of R$_5$ and R$_6$ is hydrogen and the remainder is methyl;

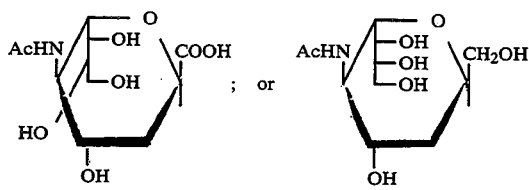

wherein m is an integer of 15 to 25, l is an integer of 0 to 3, n is an integer of 11 to 15 and Ac represents acetyl.

DETAILED DESCRIPTION OF THE INVENTION

Preferred examples of the present compounds include those containing the ceramide moiety wherein m is 15–25 (straight chain), l is 0–3 and n is 13 or 15 (straight chain).

Representative examples of the present compounds include Compounds 1 to 8 represented by the following formulas and the analogs thereof wherein the amidated fatty acid radical in the ceramide moiety is derived from a $C_{16-26}$ saturated, or mono-, di- or tri-unsaturated fatty acid and the $C_{13}H_{27}$ moiety in the aminoalcohol is modified to $C_{11}H_{23}$ or $C_{15}H_{31}$.

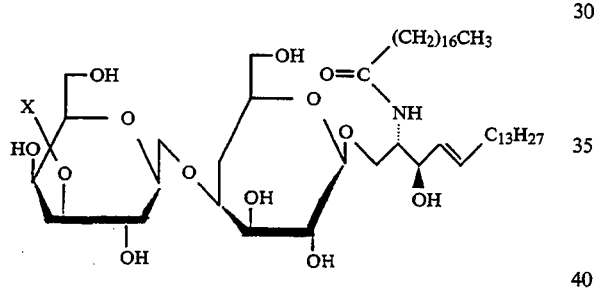

in which X represents a radical of the following formula:

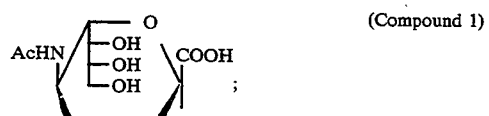
(Compound 1)

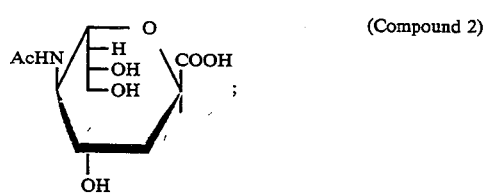
(Compound 2)

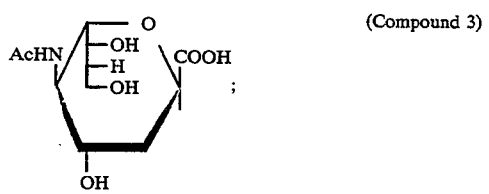
(Compound 3)

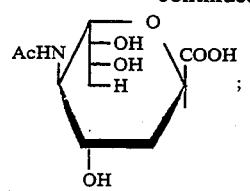
(Compound 4)

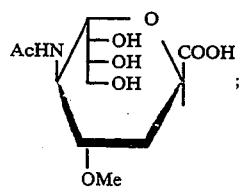
(Compound 5)

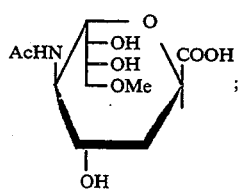
(Compound 6)

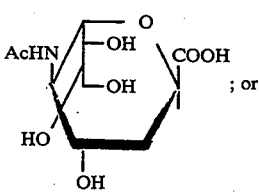
(Compound 7)

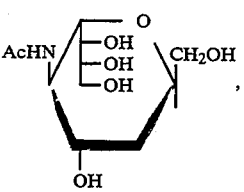
(Compound 8)

Compounds 1–4 are those of the generic formula wherein one of the hydroxyl groups in the sialic acid moiety is substituted with hydrogen; Compounds 5 and 6 are those of the generic formula wherein either one of the hydroxyl groups at the 4- and 9-position is subjected to methyletherification; Compound 7 is that of the generic formula wherein the hydroxyl group at the 8-position of the sialic acid is inverted and Compound 8 is that of the generic formula wherein the carboxyl group in the sialic acid is reduced. Those compounds have not disclosed in any references.

The ganglioside GM₃ analogs of the present invention not existing in nature are considered to have great resistance to neuraminidases, which is expected to inhibit the decomposition of metabolism of the ganglioside molecule in vivo and to have an influence on the physiological activity such as cellular recognition. Further, they may be useful in the development of medicines such as an influenzavirus inhibitor and in the clinical application.

The ganglioside GM₃ analogs of the present invention consist of the sialic acid derivative moiety, lactose moiety and ceramide moiety, as shown above in the chemical structure. Those GM₃ analogs can be prepared by the reaction steps of first synthesizing the thiomethyl form (SMe form) of the sialic acid derivative followed by condensation with the 2,6,6'-benzyl (2,6,6'-

Bz form) of lactose to form the sialyl lactose derivative and further introduction of the ceramide moiety.
The SMe of the sialic acid derivatives can be prepared as Compounds 15, 26, 35, 45, 49, 54 and 58, respectively by the reaction steps shown in Schemes 1, 2, 3, 4, 5, 6 and 7, respectively.
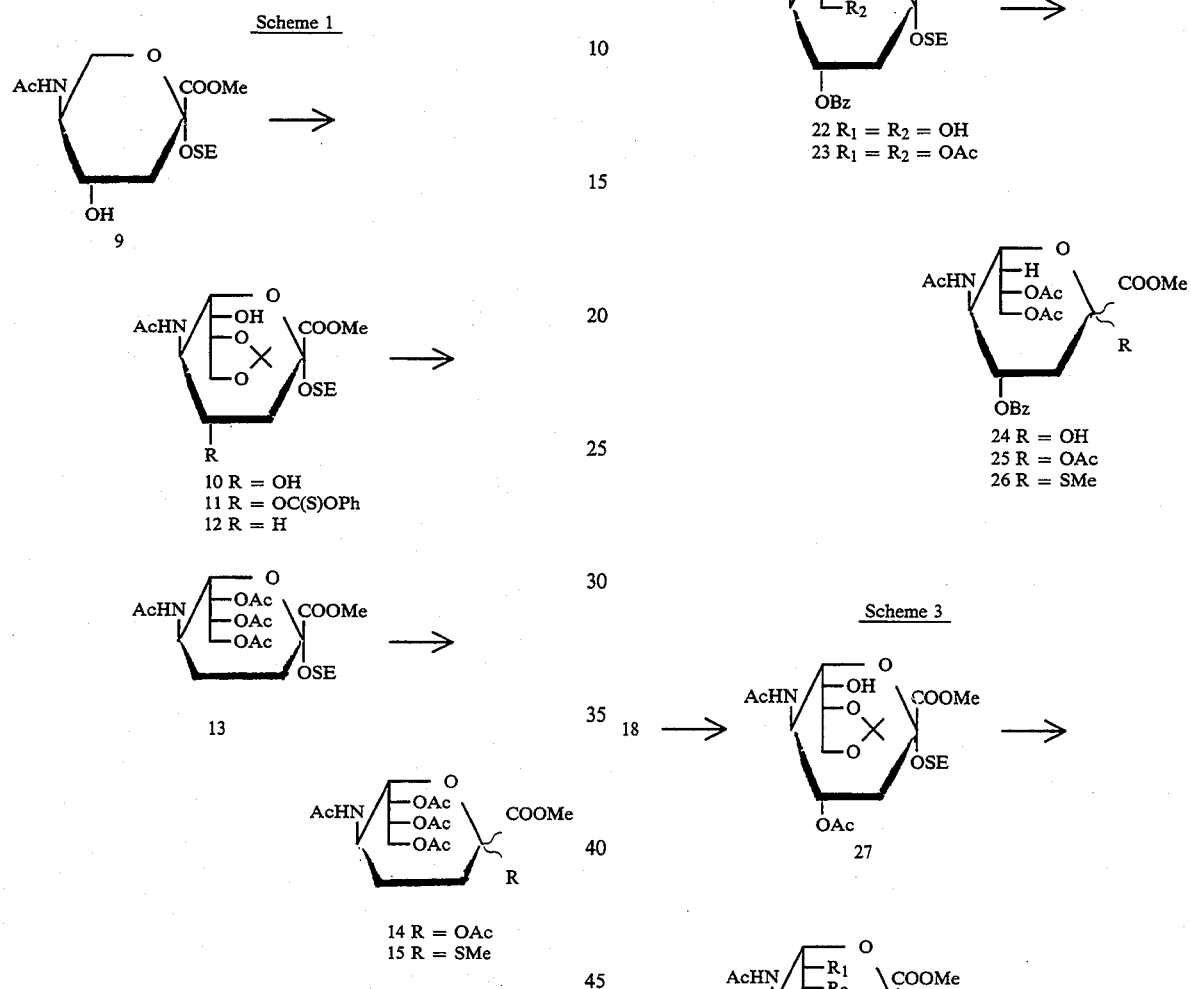
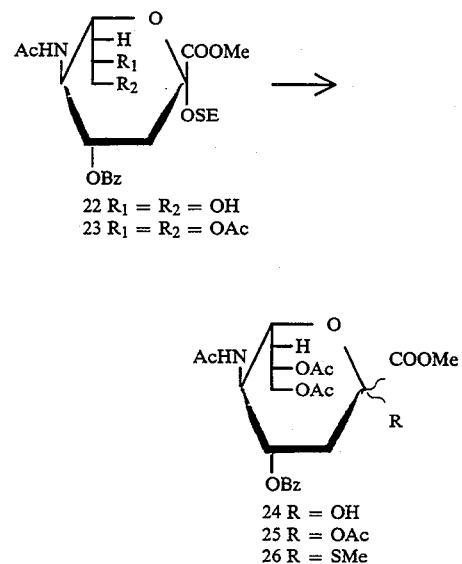
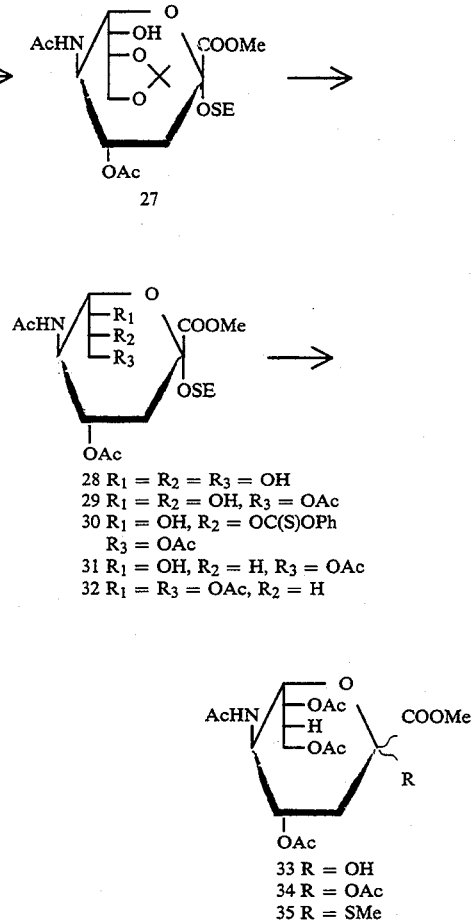
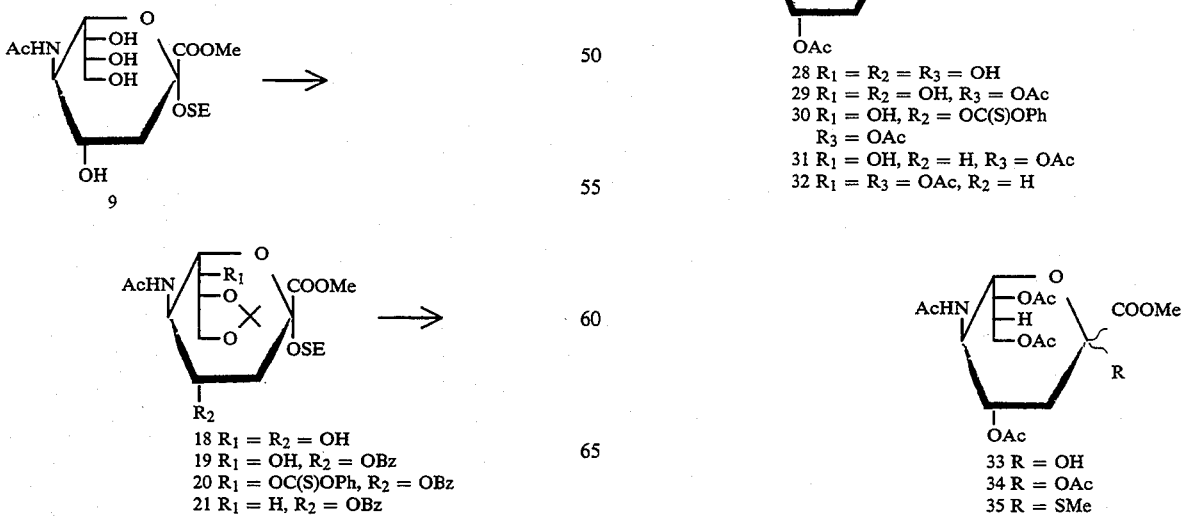

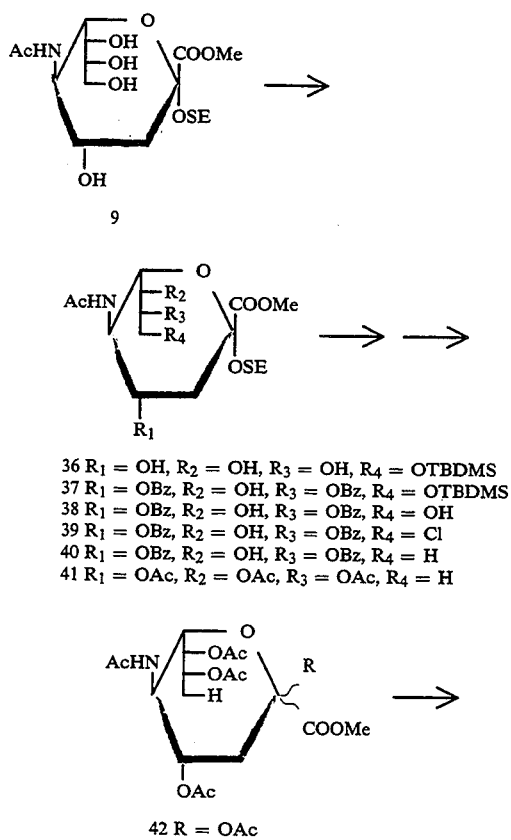
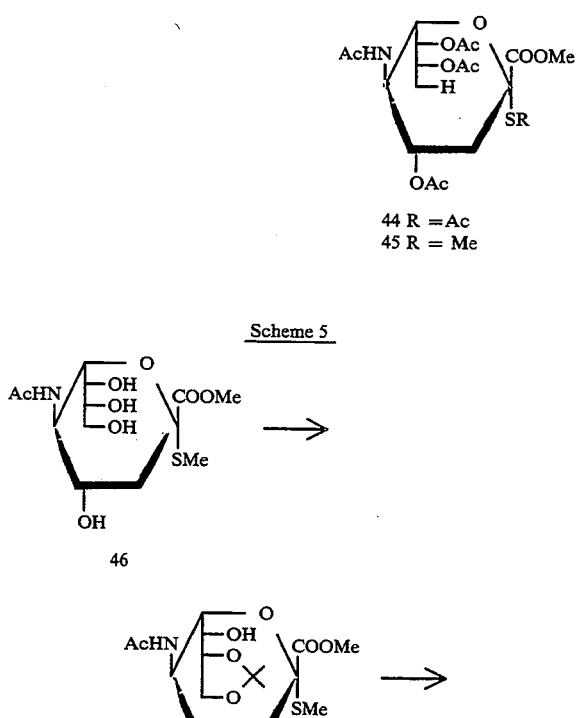
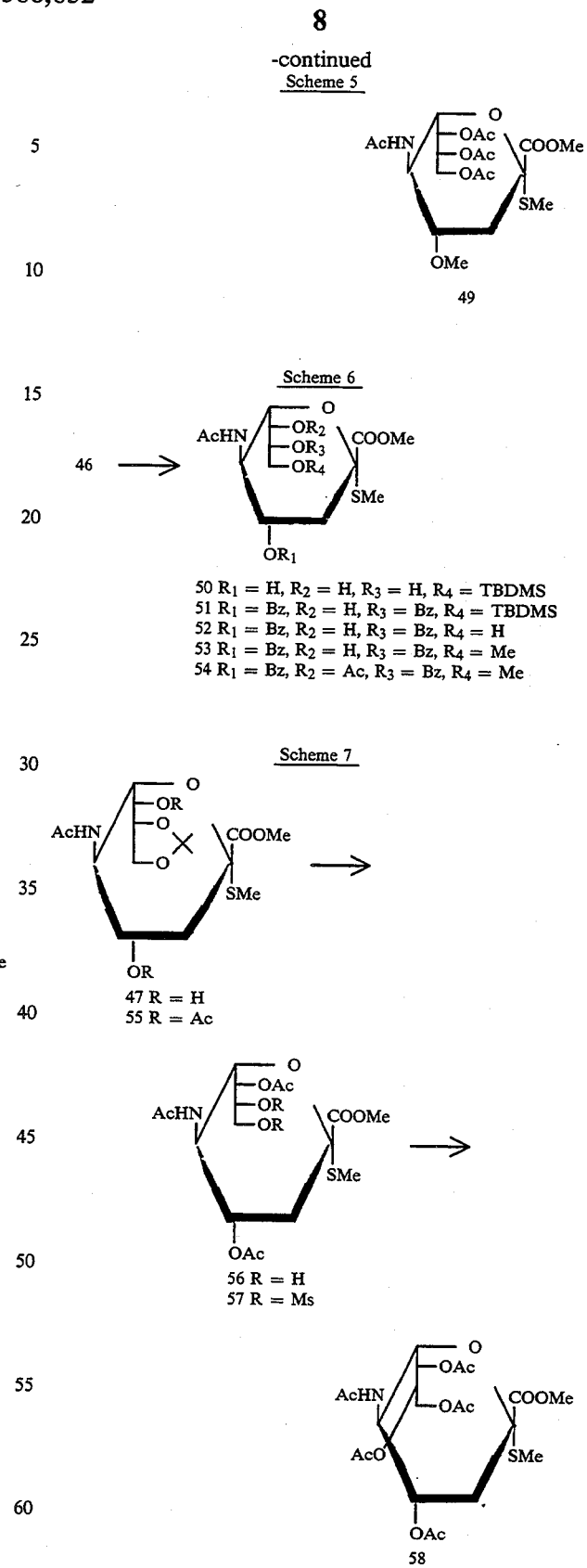
As shown in Scheme 1, Compound 15 is prepared starting from methyl[2-(trimethylsilyl)ethyl 5-acetamido-3,5-dideoxy-D-glycero-α-D-galacto-2-nonulopyranosid)onate (Compound 9) by the steps of reacting Compound 9 with 2,2-dimethoxypropane (DMP) at 50° C. in dimethylformamide in the presence of p-toluenesulfonic acid (p-TsOH) to provide the 8,9-isopropylidene (Compound 10); reacting it with phenyl chlorothionoformate to introduce selectively the leaving group, phenoxy(thiocarbonyl) group at the 4-position of Compound 10 thereby forming Compound 11; reacting it with tributyltin hydride and 2,2′-azobisisobutyronitrile in toluene at 100° C. to give Compound 12; removal of the isopropylidene group and acetylation with 80% acetic acid to provide Compound 13; reacting it with $BF_3 \cdot O(Et)_2$ for the conversion of the trimethylsilylethyl group (SE group) to the SMe group and further acetylating OAc at the 2-position to Compound 14; and reacting it with (methylthio)trimethylsilane (TMS-SMe) and trimethylsilyltrifuloromethanesulfonate (TMS-OTf) to afford the sugar donor, SMe Compound 15.

As shown in Scheme 2, Compound 26 is prepared starting from Compound 9 by the steps of reacting Compound 9 with 2,2-dimethoxypropane in dimethylformamide in the presence of p-toluenesulfonic acid to form the 8,9-isopropylidene (Compound 18=Compound 10); treating it with benzoyl chloride to provide Compound 19; reacting it with phenyl chlorothinoformate to introduce the phenoxy(thiocarbonyl) group thereby forming Compound 20; reacting this compound with tributyltin hydride and 2,2′-azobisisobutyronitrile to give Compound 21; hydrolyzing it to afford Compound 22; acetylating it with acetic anhydride to form Compound 23; treating this compound with boron trifluoride diethyl ether and further acetic anhydride to afford Compound 25; and reacting it with (methylthio)trimethylsilylsilane and trimethylsilyltrifluoromethanesulfonate to give the SMe Compound 26.

As shown in Scheme 3, Compound 35 is prepared starting from Compound 18 by the following steps. First, Compound 18 is reacted with AcCl at −40° C. to perform a selective acetylation at the 4-position with the formation of Compound 27. After removal of the isopropylidene group, Compound 28 is acetylated selectively at the 9-position at −50° C. to afford Compound 29 in high yield. Subsequently, phenoxythiocarbonyl group is introduced selectively to the hydroxyl group at the 8-position under the diluted solvent at room temperature to give Compound 30. This compound is reacted with tributyltin hydride and 2,2′-azobisisobutyronitrile, leading to Compound 31. Subsequently, Compound 31 is treated in a similar manner as described above, leading to the sugar donor, Compound 35.

The sialic acid donor (Compound 45) wherein the hydroxyl group at the 9-position is deoxidated is prepared by the reaction steps shown in Scheme 4. Compound 9 is treated with t-butyldimethylsilyl chloride (TBDMSCl) at 0° C. to introduce selectively a TBDMS group only at the 9-position, thus providing Compound 36. This compound is reacted with benzyl chloride at 0° C. to introduce selectively a benzyl group into the hydroxyl groups at the 4- and 8-positions, thus affording Compound 37. Next, the TBDMS group at the 9-position of Compound 37 is deprotected with 80% acetic acid, leading to Compound 38 containing the hydroxyl groups at the 7- and 9-positions. Compound 38 is reacted with triphenylphosphine and carbon tetrachloride in DMF at room temperature to introduce a leaving group, Cl at the 9-position, thus providing Compound 39. Subsequently, this compound is reduced with tributyltin hydride and 2,2′-azobisisobutyronitrile to afford Compound 40. After conversion of the benzyl group to the acetyl group, Compound 40 is subjected in sequence to removal of SE and introduction of OAc, Cl, SAc and SMe, leading to the sugar donor, Compound 45.

Similarly, Compounds 49 and 54 serving as the sugar donor are prepared respectively by the reaction steps shown in Schemes 5 and 6, respectively.

A pseudo sialic acid donor wherein the hydroxyl group at the 8-position is inversed, can be prepared by the reaction steps shown in Scheme 7. The 8,9-isopropylidene of the sialic acid, Compound 47 is acetylated at the hydroxyl groups at the 4- and 7-positions, followed by removal of the isopropylidene group, leading to Compound 56 containing the hydroxyl groups at the 8- and 9-positions. After introduction of a methanesulfonyl group (Ms) into the hydroxyl groups at the 8- and 9-positions, Compound 57 is reacted with cesium acetate at 120° C. in DMF to proceed with inversion in an intramolecular fashion with the removal of a methyl moiety from the carboxylmethyl group and further removal of the acetyl groups, which is methylated and acetylated again with methyl p-toluenesulfonate and triethylamine to afford the sugar donor, Compound 58.

The thiomethyl forms of the sialic acid derivatives as prepared above, Compounds 15, 26, 35, 45, 49, 54 and 58 are respectively condensed with the 2,6,6′-benzyl form of the lactose (Compound 16). In this condensation, dimethyl(methylthio)sulfonium triflate (DMTST) is used in acetonitrile as a promoter for condensation to obtain the sialyllactose derivatives (Compounds 1A–7A) in resio- and stereo-selectivity.

The resultant sialyllactose derivatives (Compounds 1A–7A) are acetylated respectively at the free hydroxyl groups to provide Compounds 1B–7B, respectively, which are treated with boron trifluoride diethyl ether to deprotect the SE group at the 4-position of glucose, thus providing Compounds 1C–7C, which are treated with 1,8-diazabicyclo[5.4.0]undec-7-ene (DBU) and $CCl_3CN$ to afford the trichloroacetimidate (Compounds 1D–7D).

Subsequently, Compounds 1D–7D are reacted respectively with the azidosphingosine derivative (Compound 17) in the presence of boron trifluoride diethyl ether to give Compounds 1E–7E. Reduction of the azide group in Compounds 1E–7E with $H_2S$ followed by condensation with stearic acid in the presence of a condensing agent such as 1-ethyl-3-(3-dimethylaminopropyl)carbodiimide hydrochloride (WSC) give Compounds 1F–7F. Finally, removal of all protecting groups affords the desired ganglioside $GM_3$ analogs (Compounds 1–7). The above reaction steps are shown in Scheme 8.

The ganglioside $GM_3$ analog, Compound 8 wherein the carboxyl group in the sialic acid is converted by reduction into the corresponding alcohol, is prepared by the reaction steps of reducing the sialyllactose derivative prepared by a conventional method (Compound 59) with $NaBH_4$ followed by reacetylation to give Compound 60 and subsequent removal of the SE group, imidation and introduction of a ceramide moiety to obtain the desired compound. Those reaction steps are shown in Scheme 9.

Scheme 8
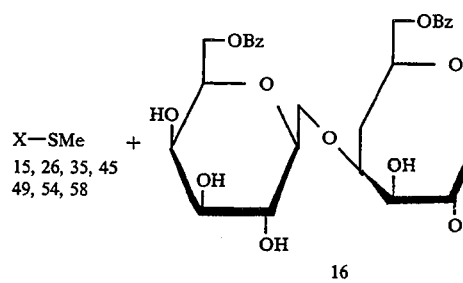
1A X = 4-deoxy-Neu5Ac(α configuration)
2A X = 7-deoxy-Neu5Ac(α configuration)
3A X = 8-deoxy-Neu5Ac(α configuration)
4A X = 9-deoxy-Neu5Ac
5A X = 4-OMe-Neu5Ac
6A X = 9-OMe-Neu5Ac
7A X = 8-epi-Neu5Ac
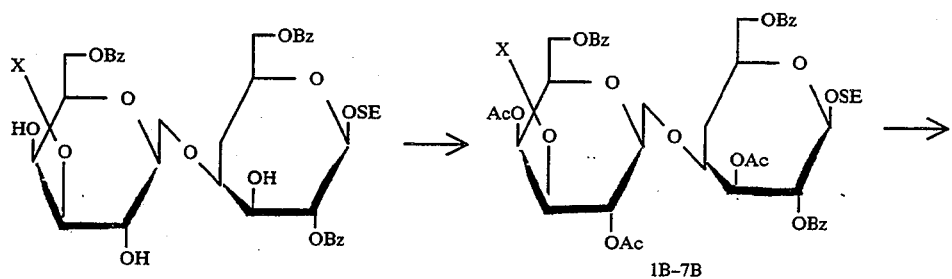
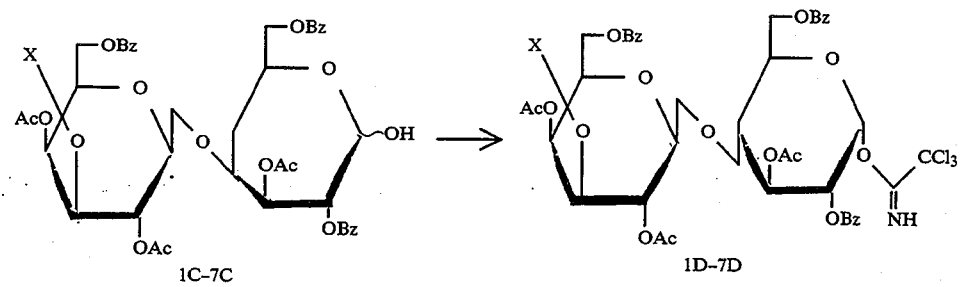
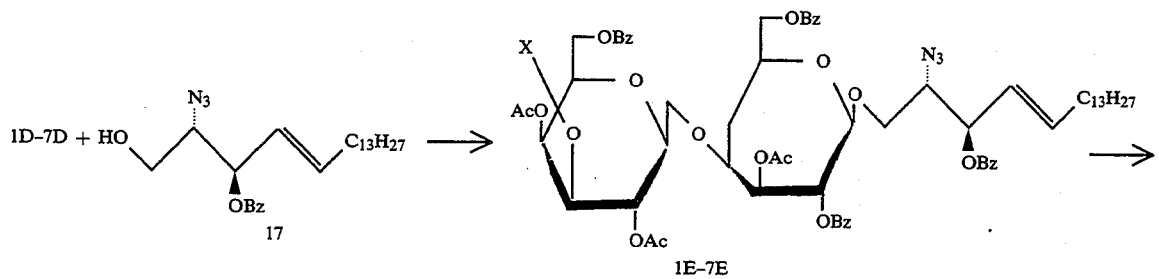
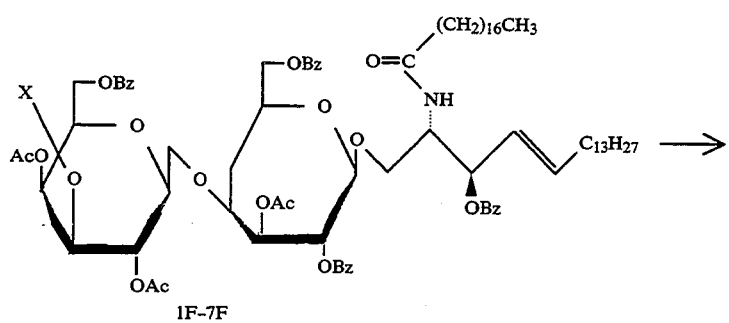

-continued
Scheme 8
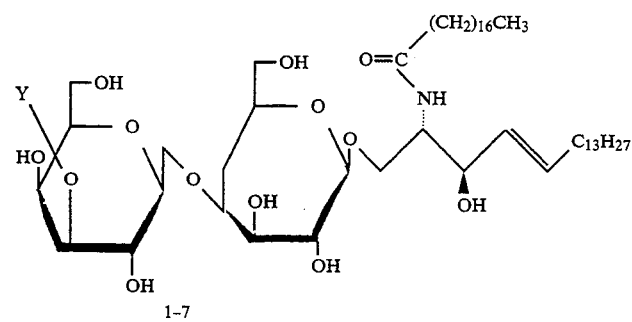
1-7
X:
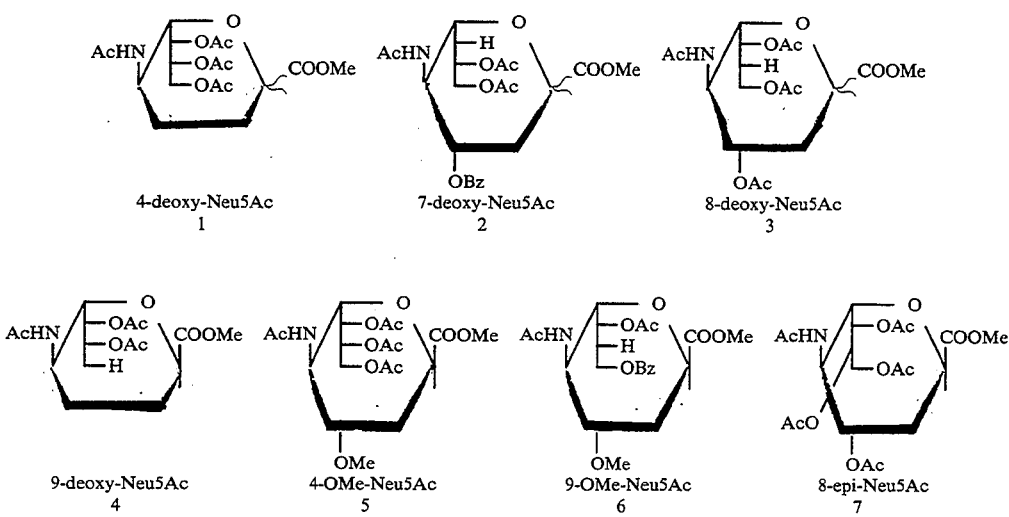
4-deoxy-Neu5Ac
1
7-deoxy-Neu5Ac
2
8-deoxy-Neu5Ac
3
9-deoxy-Neu5Ac
4
4-OMe-Neu5Ac
5
9-OMe-Neu5Ac
6
8-epi-Neu5Ac
7
Y:
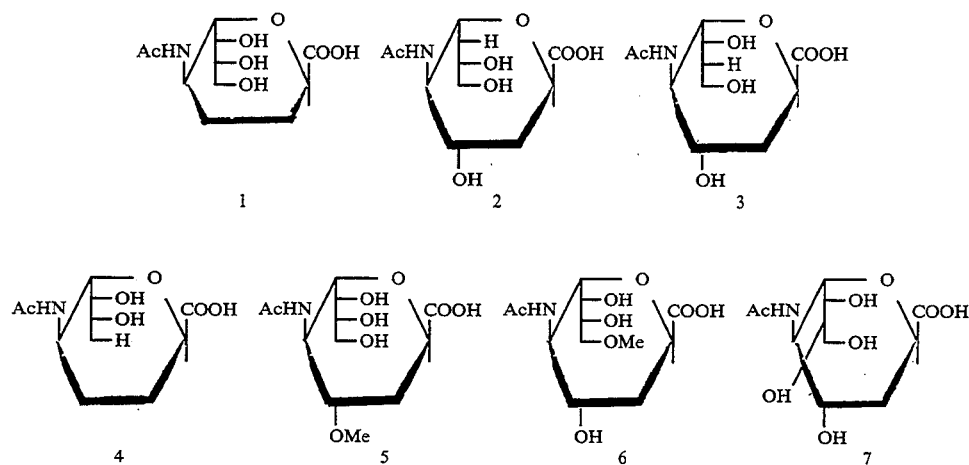
1
2
3
4
5
6
7

Scheme 9
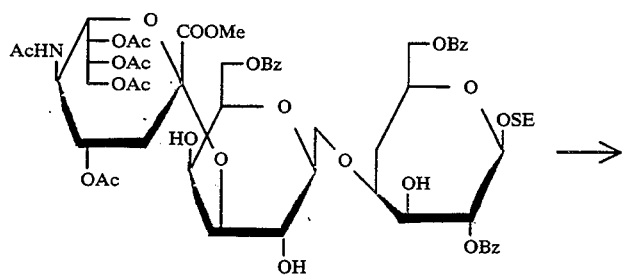
59
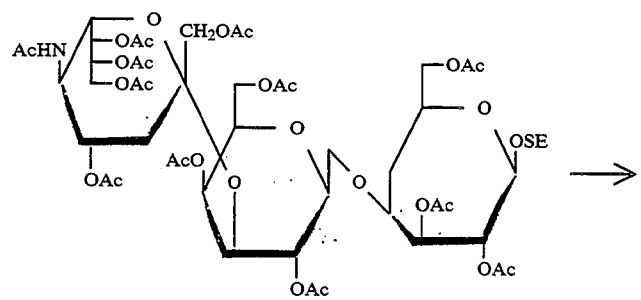
60
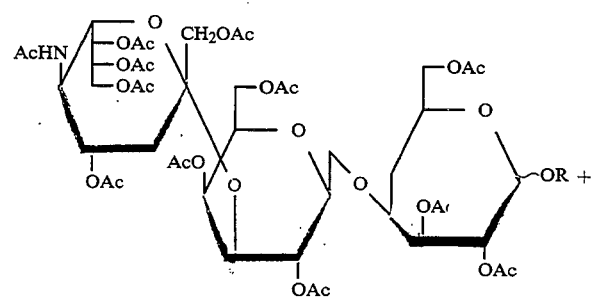
61 R = H
62 R = C(NH)CCl$_3$
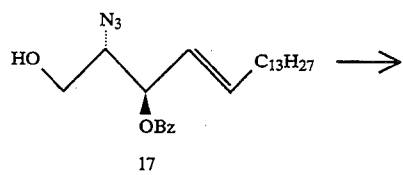
17
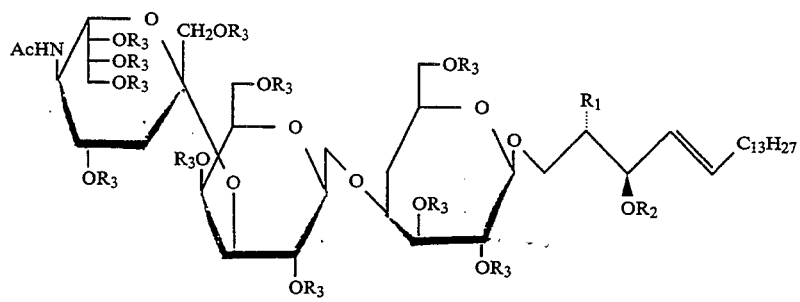
63 R$_1$ = N$_3$, R$_2$ = Bz, R$_3$ = Ac
64 R$_1$ = NHCO(CH$_2$)$_{16}$CH$_3$, R$_2$ = Bz, R$_3$ = Ac
8 R$_1$ = NHCO(CH$_2$)$_{16}$CH$_3$, R$_2$ = R$_3$ = H
The invention is further illustrated by the following examples.

Methyl[2-(trimethylsilyl)ethyl 5-acetamido-3,5-dideoxy-8,9-isopropylidene-D-glycero-α-D-galacto-2-nonulopyranosid]onate (Compound 10)

Methyl[2-(trimethylsilyl)ethyl 5-acetamido-3,5-dideoxy-D-glycero-α-D-galacto-2-nonulopyranosid]onate (Compound 9)(5.00 g, 11.81 mmol) was dissolved in dimethylformamide (50 ml), 2,2-dimethoxypropane (DMP)(7.3 ml) and Drierite ® (5.0 g) (calcium sulfate, anhydrous, Aldrich Chemical Co.) were added, and the mixture was stirred at room temperature for 3 hrs. Then p-toluenesulfonic acid was added for adjustment to pH 3 and the mixture was stirred at 40° C. for 45 minutes. After a completion of the reaction was confirmed by T.L.C. (dichloromethane:methanol=10:1), the reaction solution was neutralized with sodium bicarbonate, filtered through Celite (filter agent, Wakojunyaku Co., Japan) and concentrated under reduced pressure. The resultant syrup was subjected to column chromatography with an eluting solvent (ethyl acetate:hexane=2:1) to afford Compound 10 (5.19 g, 94.9%).

$C_{20}H_{37}NO_9Si$ (463.60)

Methyl[2-trimethylsilyl)ethyl 5-acetamido-3,5-dideoxy-8,9-O-isopropylidene-4-O-[phenoxy(thiocarbonyl)]-D-glycero-α-D-galacto-2-nonulopyranosid]onate (Compound 11)

Compound 10 (6.10 g, 13.16 mmol) was dissolved in a mixed solvent of 1/1 dichloromethane/pyridine (100 ml), the solution was cooled to 0° C., phenyl chlorothionoformate (2.0 ml) was added, and the mixture was stirred at 0° C. for 7 hrs. After a completion of the reaction was confirmed by T.L.C. (dichloromethane:methanol=20:1), the reaction solution was mixed with methanol and concentrated under reduced pressure. The resultant syrup was extracted with dichloromethane, the organic layer was washed with HCl and $H_2O$, dehydrated with anhydrous sodium sulfate, separated by filtration and concentrated under reduced pressure. The resultant syrup was subjected to column chromatography with and eluting solvent (ethyl acetate:hexane=2:3) to afford Compound 11 (7.70 g, 97.6%).

$C_{27}H_{41}NO_{10}SSi$ (599.77) $[\alpha]_D = -94.62°$ (c=1.414, $CHCl_3$)

IR $\nu^{film}_{max}cm^{-1}$: 3700–3150 (NH OH), 3170–2800 (CH), 1750 (ester), 1660, 1550 (amide), 860, 840 (TMS, $Me_2C$), 740, 700 (phenyl)

$^1H$ NMR ($CDCl_3$) 7.44–7.03 H(m, 5H, OBz), 6.25 (d, 1H, $J_{5, nh}$=8.06 Hz, NH) 5.24 (ddd, 1H, $J_{4,5}$=10.62 Hz, H-4), 4.33 (m, 1H, H-8), 4.23 (m, 1H, CHC $H_2Si$), 4.10 (q, 1H, H-5), 4.05 (dd, 1H, $J_{8,9}$=6.59 Hz, $J_{rcm}$=8.43 Hz, H-9), 3.81 (s, 3H, COOMe), 3.53 (dd, 1H, $J_{5,6}$=10.44 Hz, $J_{6,7}$=2.38 Hz, H-6), 2.67 (dd, 1H, $J_{3a,3c}$=12.64 Hz, $J_{3c,4}$=5.13 Hz, H-3e), 2.00 (s, 3H, NAc), 1.40, 1.36 (2s, 6H, $Me_2C$), 0.89 (m, 2H, $OCH_2CH_2Si$), 0.00 (s, 9H, $Me_3Si$) Methyl[2-trimethylsilyl)ethyl 5-acetamido-3,4,5-trideoxy-8,9-O-isopropylidene-α-D-manno-2-nonulopyranosid]onate (Compound 12)

Compound 1 (0.10 g, 0.17 mmol) was dissolved in toluene (5 ml), tributyltin hydride (0.45 ml) and 2,2'-azobisisobutylonitrile (2 mg) were added and the mixture was stirred at 100° C. for 20 minutes. After a completion of the reaction was confirmed by T.L.C. (dichloromethane:methanol=15:1), the reaction solution was concentrated under reduced pressure. The resultant syrup was subjected to column chromatography with an eluting solvent (dichloromethane:methanol=110:1) to afford Compound 12 (0.65 g, 84.24%).

$C_{20}H_{37}NO_8SI$(447.60) $[\alpha]_D$=1.66° (c=2.048, $CHCl_3$)
IR $\nu^{film}_{max}cm^{-1}$L 3700–3150 (NH, OH), 3150–2800 (CH), 1750 (ester), 1660, 1550 (amide), 860 840 (TMS, $Me_2C$)

$^1H$ NMR ($CDCl_3$) 6.17 (d, 1H, $J_{5, NH}$=8.43 Hz, NH), 4.28 (d, 1H, $J_{7, OH}$=5.13 Hz, OH-7), 3.80 (s, 3H, COOMe), 3.44 (m, 1H, $J_{5, 6}$=10.26 Hz, $J_{6, 7}$=2.56 Hz, H-6), 3.42 (m, 1H, CHC$H_2Si$), 2.36 (ddd, 1H, $J_{3a, 3c}$=13.36 Hz, H-3a), 2.00 (m, 1H, H-4e), 2.00 (s, 3H, NAc), 1.79 (ddd, 1H, $J_{3c, 4}$=4.40 Hz, H-3e), 1.40 (m, 1H, H-4-a), 1.42, 1.38 (2s, 6H, $Me_2C$), 0.87 (m, 2H, $OCH_2CH_2Si$), 0.00 (s, 9H, $Me_2Si$)

Methyl[2-(trimethylsilyl)ethyl 5-acetamido-7,8,9-tri-O-acetyl-3,4,5-trideoxy-α-D-manno-2-nonulopyranosid]onate (Compound 13)

Compound 12 (0.20 g, 0.45 mmol) was dissolved in 80% acetic acid (6 ml) and the mixture was stirred at room temperature for 15 hrs. After a completion of the reaction was confirmed by T.L.C. (dichloromethane:methanol=10:1), the reaction solution was concentrated under reduced pressure to dryness. Then the solid was dissolved in pyridine (10 ml), acetic anhydride (7 ml) was added and the mixture was stirred at room temperature overnight. After a completion of the reaction was confirmed by T.L.C. (dichloromethane:methanol=18:1), the reaction solution was mixed with methanol and concentrated under reduced pressure. The resultant syrup was extracted with dichloromethane, the dichloromethane layer was washed with HCl and $H_2O$, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=2:3) to afford Compound 13 (0.21 g, 88.2%).

$C_{23}H_{39}NO_{11}Si$ (533.65) $[\alpha]_D$= +12.66° (c=0.600, $CHCl_3$)

IR $\nu^{film}_{max}cm^{-1}$: 3700–3160 (NH), 3160–2800 (CH), 1750 (ester), 1660, 1550 (amide), 860, 840 (TMS)

$^1H$ NMR ($CDCl_3$) 5.40 (m, 1H, $J_{7, 8}$=10.80 Hz, $J_{8, 9}$=2.57 Hz, $J_{8,9'}$=5.31 Hz, H-8), 5.33 (dd, 1H, $J_{6,7}$=2.20 Hz, H-7), 5.27 (d, 1H, $J_{5,NH}$=9.34 Hz, NH), 4.30 (dd, 1H, $J_{gem}$=12.46 Hz, H-9), 4.11 (dd, 1H, H-9') 4.02 (dd, 1H, $J_{5,6}$=10.44 Hz, H-6), 3.94–3.81 (m, 2H, H-5, CHC$H_2Si$), 3.74 (s, 3H, COOMe), 3.25 (m, 1H, CH' C$H_2Si$), 2.27 (m, 1H, $J_{3a,3e}$=13.74 Hz, $J_{3a,4e}$=3.48 Hz, H-3a), 2.12–1.89 (4s, 12H, 3OAc, NAc), 1.76 (m, 1H, H-3e), 1.28 (m, 1H, $J_{4a,5}$ −10.26 Hz, H-4-a), 0.86 (m, 2H, $OCH_2CH_2Si$), 0.00 (s, 9H, $Me_3Si$)

Methyl(5-acetamido-2,7,8,9-tetra-O-acetyl-3,4,5-trideoxy-D-manno-2-nonulopyranosid)onate (Compound 14)

Compound 13 (0.20 g, 0.37 mmol) was dissolved in dichloromethane (5 ml), the solution was cooled to 0° C., boron trifluoride diethyl ether (0.15 ml) was added and the mixture was stirred at 0° C. for 2 hrs. After a completion of the reaction was confirmed by T.L.C. (dichloromethane:methanol=10:1), the reaction solution was extracted with dichloromethane. The dichloromethane layer was washed with sodium bicarbonate and $H_2O$, dehydrated with anhydrous sodium sulfate, separated by filtration and washed with dichloromethane. The combined filtrate and washings were concentrated under reduced pressure to dryness. It was dissolved in pyridine (8 ml), acetic anhydride (5 ml) was added and the mixture was stirred at room temperature overnight. After a completion of the reaction was confirmed by T.L.C. (dichloromethane:methanol=18:1), methanol was added, and the reaction solution was concentrated under reduced pressure. The resultant syrup was extracted with dichloromethane, the dichloromethane layer was washed with HCl and H$_2$O, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=3:2) to afford Compound 14 (0.12 g, 67.4%).

C$_{20}$H$_{29}$NO$_{12}$ (475.45)

IR $\nu^{film}_{max}$cm$^{-1}$: 3700–3160 (NH), 3160–2800 (CH), 1750 (ester), 1660, 1550 (amide)

Methyl(methyl 5-acetamido-7,8,9-tri-O-acetyl-3,4,5-trideoxy-2-thio-D-manno-2-nonulopyranosid)onate (Compound 15)

Compuond 14 (0.50 g, 1.05 mmol) was dissolved in dichloromethane (20 ml), TMS-SMe (0.40 g, 3.33 mmol) and TMS-OTf (0.12 g, 0.05 mmol) were added at 0° C. and the mixture was stirred at room temperature for 10 hrs. After a completion of the reaction was confirmed by T.L.C. (dichloromethane:methanol=18:1), the reaction solution was extracated with dichloromethane, the dichloromethane layer was washed with sodium bicarbonate and H$_2$O, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=2:1) to afford Compound 15 (0.45 g, 92.4%).

C$_{19}$H$_{29}$NO$_{10}$S (463.50)

IR $\nu^{film}_{max}$cm$^{-1}$: 3700–3170 (NH), 3170–2800 (CH), 1760 (ester), 1680, 1560 (amide)

2-(Trimethylsilyl)ethyl O-(methyl 5-acetamido-7,8,9-tri-O-acetyl-3,4,5-trideoxy-α-D-manno-2-nonulopyranosylonate)-(2→3)-O-(6-O-benzoyl-β-D-galactopyranosyl)-(1→4)-2,6-di-O-benzoyl-β-D-glucopyranoside (Compound 1A)

Compound 15 (1.60 g, 3.45 mmol) and Compound 16 (1.35 g, 1.79 mmol) were dissolved in acetonitrile (17 ml), Molecular Sieves 3A (5.0 g) was added and the mixture was stirred overnight. After cooling to −15° C., dimethyl(methylthio)sulfonium triflate (DMTST) (50%, 5.0 g) was added and the mixture was stirred at −15° C. for 2 days. After a completion of the reaction was confirmed by T.L.C. (dichloromethane:methanol=18:1), the reaction solution was filtered through Celite. The combined filtrate and washings were extracted with dichloromethane, the dichloromethane layer was washed with sodium carbonate and water. After dehydrating with anhydrous sodium sulfate, it was separated by filtration and washed with dichloromethane. The combined filtrate and washings were concentrated under reduced pressure. The resultant syrup was subjected to column chromatography with an eluting solvent (ethyl acetate:hexane=3:1) to afford Compound 1A (0.53 g, 25.4%).

C$_{56}$H$_{71}$NO$_{24}$Si(1170.26) [α]$_D$=+24.12° (c=0.970, CHCl$_3$)

IR $\nu^{film}_{max}$cm$^{-1}$: 3700–3150 (NH), 3150–2800 (CH), 1750 (ester), 1660, 1550 (amide), 860, 840 (Me$_3$Si), 710 (phenyl)

270 MHz $^1$H-NMR (CDCl$_3$)

Lac unit: δ 8.20–7.37 (m, 15H, 3 BzO), 5.38 (dd, 1H, J$_{1,2}$=8.06 Hz, J$_{2,3}$=9.53 Hz, H-2), 4.87 (dd, 1H, J$_{gem}$=11.72 Hz, H-6), 4.76 (d, 1H, H-1), 4.75 (d, 1H, J$_{1'}$, $_{2'}$=7.69 Hz, H-1), 4.62 (dd, 1H, H-6), 0.98 (m, 2H, CH$_2$CH$_2$Si), 0.00 (s, 9H, Me$_3$Si)

Neu5Ac unit: 5.91 (d, 1H, J$_{5,NH}$=9.89 Hz, NH), 5.52 (m, 2H, H-7, 8), 3.86 (s, 3H, COOMe), 2.50–1.54 (m, 4H, H-3a,3e,4a,4e), 2.26–2.04 (4s, 12H, 3AcO, AcN)

2-(Trimethylsilyl)ethyl O-(methyl 5-acetamido-7,8,9-tri-O-acetyl-3.4.5-trideoxy-α-D-manno-2-nonulopyranosylonate)-(2→3)-O-(2,4-di-O-acetyl-6-O-benzoyl-β-D-galactopyranosyl)-(1→4)-3-O-acetyl-2,6-di-O-benzyl-β-D-glucopyranoside (Compound 1B)

Compound 1A (0.43 g, 0.37 mmol) was dissolved in pyridine (15 ml), acetic anhydride (12 ml) was added and the mixture was stirred at room temperature overnight. After a completion of the reaction was confirmed by T.L.C. (dichloromethane:methanol=18:1), methanol was added to decompose excessive reagent and concentrated under reduced pressure. The resultant syrup was subjected to column chromatography with an eluting solvent (dichloromethane:methanol=70:1) to afford Compound 1B (0.40 g, 84.0%).

C$_{62}$H$_{77}$NO$_{27}$Si (1296.37) [α]$_D$= 19.76° (c=2.246, CHCl$_3$)

IR $\nu^{film}_{max}$cm$^{-1}$: 3700–3160 (NH), 3160–2800 (CH), 1730 (ester), 1650, 1530 (amide), 850, 830 (Me$_3$Si), 710 (phenyl)

270 MHz $^1$H-NMR (CDCl$_3$)

Lac unit: δ 8.19–7.27 (m, 15H, 3 BzO), 5.60 (t, 1H, J$_{2,3}$=J$_{3,4}$=9.53 Hz, H-3), 5.32 (dd, 1H, J$_{1,2}$=8.06 Hz, H-2), 5.16 (dd, 1H, J$_{1'}$, $_{2'}$=8.06 Hz, J$_{2',3'}$=10.07 HZ, H-2'), 5.09 (d, 1H, H-4'), 5.02 (d, 1H, H-1'), 4.78 (d, 1H, H-1), 4.67 (dd, 1H, J$_{3',4'}$=3.12 Hz, H-3'), 0.96 (m, 2H, CH$_2$CH$_2$Si), 0.00 (s, 9H, Me$_3$Si)

Neu5Ac unit: 5.72 (m, 1H-8), 5.47 (dd, 1H, J$_{6,7}$=2.56 Hz, J$_{7,8}$=9.34 Hz, H-7), 3.77 (s, 3H, COOMe), 2.33–1.99 (7s, 21H, 6AcO, AcN), 1.62 (m, 1H, H-3e), 1.41 (m, 1H, J$_{4a,5}$=10.45 Hz, H-4a)

O-(Methyl 5-acetamido-7,8,9-tri-O-acetyl-3,4,5-trideoxy-α-D-manno-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 1C)

Compound 1B (0.40 g, 0.31 mmol) was dissolved in dichloromethane (10 ml), boron trifluoride diethyl ether (0.5 ml) was added dropwise under ice-cooling and the mixture was stirred at 0° C. for 6 hrs. After a completion of the reaction was confirmed by T.L.C. (dichloromethane:methanol=18:1), the reaction solution was extracted with dichloromethane, the dichloromethane layer was washed with sodium bicarbonate and H$_2$O, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=55:1) to afford Compound 1C (0.35 g, 94.9%).

C$_{57}$H$_{65}$NO$_{27}$ (1196.13) [α]$_D$=+52.92° (c=1.470, CHCl$_3$)

IR $\nu^{film}{}_{max}$cm$^{-1}$: 3720–3140 (OH, NH), 3140–2800 (CH), 1740 (ester), 1670, 1530 (amide), 710 (phenyl)

O-Methyl 5-acetamido-7,8,9-tri-O-acetyl-3,4,5-trideoxy-α-D-manno-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloracetimidate (Compound 1D)

Compound 1C (0.35 g, 0.29 mmol) was dissolved in dichloromethane (4 ml), trichloroacetonitrile (1.0 ml) and 1,8-diazabicyclo[5.4.0]-undec-7-ene (40 mg) were added under ice-cooling and the mixture was stirred at 0° C. for 2 hrs. After a completion of the reaction was confirmed by T.L.C. (dichloromethane:methanol=18:1), the reaction solution was concentrated under reduced pressure. The resultant syrup was subjected to column chromatography with an eluting solvent (dichloromethane:methanol=70:1) to afford Compound 1D (0.32 g, 81.6%).

$C_{59}H_{65}N_2O_{27}Cl_3$ (1340.52) $[\alpha]_D = +55.81°$ (c=1.480, CHCl$_3$)

IR $\nu^{film}{}_{max}$cm$^{-1}$: 3700–3150 (NH), 3150–2800 (CH), 1740 (ester), 1670, 1540 (amide), 710 (phenyl)

270 MHz $^1$H-NMR (CDCl$_3$)

Lac unit: δ 8.55 (s, 1H, C=NH), 8.07–7.27 (m, 15H, 3 BzO), 6.65 (d, 1H, $J_{1,2}$=3.84 Hz, H-1), 5.87 (t, 1H, $J_{2,3}$=$J_{3,4}$=9.53 Hz, H-3), 5.28 (dd, 1H, H-2), 5/07(dd, 1H, H-2'), 4.95(d, 1H, $J_{1',2'}$=7.88 Hz H-1'), 4.82(dd, 1H, $J_{2',3'}$=10.07 Hz, $J_{3',4'}$=3.11 Hz H-3')

Neu5Ac unit: 5.57 (m, 1H, H-8), 5.35 (dd, 1H, $J_{6,7}$=2.57 Hz, $J_{7,8}$=9.15 Hz, H-7), 3.66 (s, 3H, COOMe), 2.19–1.87 (7s, 21H, 6 AcO, AcN), 1.50 (m, 1H, H-3e), 1.28 (m, 1H, H-4a)

O-(Methyl 5-acetamido-7,8,9-tri-O-acetyl-3,4,5-trideoxy-α-D-manno-2-nonulopyranosylonate)-2→3)-O-(2,4-di-O-acetyl-6-O-benzoyl-β-D-galactopyranosyl)-1→4)-O-(3-O-acetyl-2,6-di-O-benzoyl-β-D-glucopyranosyl)-(1→1)-(2S,3R,4E)-2-azido-3-O-benzoyl-4-octadecene-1,3-diol (Compound 1 D)

Compound 1D (0.18 g, 0.13 mmol) and Compound 17 (0.0 g, 0.23 mmol) were dissolved in dichloromethane (4 ml), Molecular Sieves 4A type AW 300 (2.5 g) was added and the mixture was stirred at room temperature for 30 minutes. The boron trifluoride diethyl ether (0.07 ml) was added dropwise under ice-cooling and the mixture was stirred at 0° C. for 4 hrs. After a completion of the reaction was confirmed by T.L.C. (dichloromethane:methanol=18:1), the reaction solution was filtered through Celite. The combined filtrate and washings were extracted with dichloromethane, the dichloromethane layer was washed with an aqueous sodium carbonate solution and dehydrated with anhydrous sodium sulfate, it was separated by filtration and washed with dichloromethane. The combined filtrate and washings were concentrated under reduced pressure. The resultant syrup was subjected to column chromatography with an eluting solvent (dichloromethane:methanol=70:1) to afford Compound 1E (0.17 g, 78.7%).

$C_{82}H_{102}N_4O_{29}$ (1607.72) $[\alpha]_D = +7.80°$ (c=1.512, CHCl$_3$)

IR $\nu^{film}{}_{max}$cm$^{-1}$: 3700–3140 (NH), 3140–2800 (CH), 2100 (N$_3$), 1740 (ester), 1660, 1540 (amide), 710(phenyl)

270 MHz $^1$H-NMR (CDCl$_3$)

Lac unit: δ 8.12–7.26 (m, 20H, 4 BzO), 5.49 (t, 1H, $J_{2,3}$=9.71 Hz, H-3), 5.24 (dd, 1H, $J_{1,2}$=8.06 Hz, H-2), 5.01 (dd, 1H, $J_{1',2'}$=7.51 Hz, $J_{3',3'}$=10.08 Hz, H-2'), 4.96 (d, 1H, H-4'), 4.90 (d, 1H, H-1'), 4.68 (d, 1H, H-1), 4.55 (dd, 1H, $J_{3',4'}$=3.11 Hz)H-3')

Neu5Ac unit: 5.35 (dd, 1H, $J_{6,7}$=2.93 Hz, $J_{7,8}$=9.16 Hz, H-7), 3.65 (s, 3H, COOMe), 2.19–1.86 (7s, 21H, 6AcO, AcN), 1.50 (m, 1H, H-4a)

Sphingosine unit: 5.66 (m, 1H, $J_{5,6}$=$J_{5,6'}$6.96 Hz, H-5), 1.24 (s, 22H, 11 CH$_2$), 0.87 (t, 3H, CH$_3$)

O-)Methyl 5-acetamido-7,8,9-tri-O-acetyl-3,4,5-trideoxy-α-D-manno-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-2-octadecanamide-4-octadencene-1,3-diol (Compound 1F)

Compound 1E (120 mg, 0.07 mmol) was dissolved in a mixed solvent of 5/1 pyridine/water (15 ml) and the solution was stirred at room temperature for 5 days while blowing hydrogen sulfide gas. After a completion of the reaction was confirmed by T.L.C. (ethyl acetate), the reaction solution was evaporated under reduced pressure to dryness. The solid was didsolved in dichloromethane (6 ml), stearic acid (100 mg, 0.34 mmol) and WSC (100 mg) were added and the mixture was stirred at room temperature overnight. After a completion of the reaction was confirmed by T.L.C. (dichloromethane:methanol=18:1), the reaction solution was extracted withdichloromethane. The dichloromethane layer was washed with water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=75:1) to afford Compound 1F (110 mg, 79.8%).

$C_{100}H_{138}N_2O_{30}$(1848.19) $[\alpha]_D = +17.98°$ (cb =2.068, CHCl$_3$)

IR $\nu^{film}{}_{max}$cm$^{-1}$: 3700–3140 (NH), 3140–2800 (CH), 1740 (ester), 1660, 1530 (amide), 710 (phenyl)

270 MHz $^1$H-NMR (CDCl$_3$)

Lac unit: δ 8.13–7.26 (m, 20H, 4 bzO), 5.48 (t, 1H, $J_{2,3}$=9.89 Hz, H-3), 5.18 (dd, 1H, $J_{1,2}$=7.69 Hz, H-2), 5.02 (dd, 1H, $J_{1',2'}$=8.06 Hz, H-2'), 4.98 (d, 1H, H-4'), 4.86 (d, 1H, H-1'), 4.60 (d, 1H, H-1), 4.55 (dd, 1H, $J_{2',3'}$=10.45 Hz, $J_{3',4'}$=3.30 Hz, H-3')

Neu5Ac unit: 5.65 (d, 1H, $J_{5,NH}$=9.34 Hz, NH), 5.55 (m, 1H, H-8), 5.37 (dd, 1H, $J_{6,7}$=2.74 Hz, $J_{7,8}$=9.15 Hz, H-7), 3.66 (s, 3H, COOMe), 2.16–1.87 (7s, 21H, 6AcO, AcN), 1.78 (m, 1H, H-3e)

Cer unit: 5.75 (td, 1H, $J_{5,6}$=$J_{5,6'}$=6.59 Hz, H-5), 1.26 (s, 50H, 25CH$_2$), 0.87 (t, 6H, 2CH$_3$)

O-(5-Acetamido-3,4,5-trideoxy-α-D-manno-2-nonulopyranosylonic acid)-(2→3)-O-(β-D-galactopyranosyl)-(1→4)-O-(β-D-glucopyranosyl)-(1→1)-(2S,3R,4E)-2-octadecanamide-4-octadecene-1,3-diol (Compound 1)

Compound 1F (105 mg, 0.057 mmol) was dissolved in methanol (3.5 ml), 28% sodium methylate solution (5 drops) was added and the mixture was stirred at room temperature for 6 hrs. Water (0.5 ml) was added and the mixture was stirred for further 24 hrs. After a completion of the reaction was confirmed by T.L.C. (butanol:ethanol:water=4:2:1), the reaction solution was neutralized with ion exchange resin IR-120 (H+), filtered and concentrated under reduced pressure. The resultant syrup was subjected to gel filtration with Sephadex LH-20 to afford Compound 1 (62 mg, 93.3%).

$C_{59}H_{108}N_2O_{20}$ (1165.51) $[\alpha]_D = -13.93°$ (c=1.292, MeOH:CH$_2$Cl$_2$=1:1)

IR $\nu^{KBr}_{max}$cm$^{-1}$: 3700–2800 (OH,NH), 2940, 2860 (Me, methylene), 1730 (C=O), 1640, 1550 (amide) 2700 MHz $^1$H-NMR (CDCl$_3$)

Lac unit: δ 4.42 (d, 1H, $J_{1',2'}$=7.51 Hz, H-1'), 4.30 (d, 1H, $J_{1,2}$=7.69 Hz, H-1)

Neu5Ac unit: 1.98 (s, 3H, NAc)

Cer unit: 5.68 (td, 1H, $J_{5,6}$=$J_{5,6'}$=6.59 Hz, H-5), 4.43 (dd, 1H, $J_{4,5}$=7.5 Hz, H-4), 1.28 (s, 50H, 25CH$_2$), 0.89 (t, 6H, 2CH$_3$)

EXAMPLE 2

Methyl[2-(trimethylsilyl)ethyl 5-acetamido-3,5-dideoxy-8,9-isopropylidene-D-glycero-α-D-galacto-2-nonulopyranosid]onate (Compound 18)

Compound 9 (5.00 g, 11.81 mmol) was dissolved in dimethylformamide (50 ml), 2,2-dimethoxypropane (DMP)(7.3 ml) and Drierite ® (5.0 g) were added, and the mixture was stirred at room temperature for 3 hrs. Then p-toluenesulfonic acid was added for adjustment to pH 3 and the mixture was stirred at 40° C. for 45 minutes. After a completion of the reaction was confirmed by T.L.C. (dichloromethane:methanol=10:1), the reaction solution was neutralized with sodium bicarbonate, filtered through Celite and concentrated under reduced pressure. The resultant syrup was subjected to column chromatography with an eluting solvent (ethyl acetate:hexane=2:1) to afford Compound 18 (5.19 g, 94.9%).

$C_{20}H_{37}NO_9Si$ (463.60)

Methyl[2-(trimethylsilyl)ethyl 5-acetamido-4-O-benzoyl-3,5-dideoxy-8,9-O-isopropylidene-D-glycero-α-D-galacto-2-nonulopyranosid]onate (Compound 19)

Compound 18 (5.00 g, 10.79 mmol) was dissolved in dichloromethane (100 ml) and the solution was cooled to −5° C. Then benzoyl chloride (2.1 ml) diluted with pyridine (25 ml) and dichloromethane was added dropwise and the mixture was stirred at that temperature for 15 minutes. After a completion of the reaction was confirmed by T.L.C. (dichloromethane:methanol=18:1), the reaction solution was mixed with methanol to decompose excessive reagent, concentrated under reduced pressure and extracted with dichloromethane. The organic layer was washed with HCl and H$_2$O, dehydrated with anhydrous sodium sulfate, separated by filtration and concentrated under reduced pressure. The resultant syrup was subjected to column chromatography with an eluting solvent (ethyl acetate:hexane=1:1) to afford Compound 19 (6.10 g, quant.).

$C_{27}H_{41}NO_{10}Si$ (567.71) $[\alpha]_D = -38.00°$ (c=0.100, CHCl$_3$)

IR $\nu^{film}_{max}$cm$^{-1}$: 3700–3150 (NH, OH), 3100–2900 (CH), 1730 (ester), 1660, 1550 (amide), 860, 840 (TMS ethyl), 720 (phenyl)

$^1$H NMR (CDCl$_3$) δ ppm 8.00–7.25 (m, 5H, Ph), 6.13 (d, 1H, $J_{5,NH}$=7.87 Hz, NH), 5.24 (ddd, 1H, $J_{3e,4}$=4.95 Hz, $J_{4,5}$=10.44 Hz, H-4), 4.38 (m, 1H, H-7), 4.33 (dd, 1H, $J_{9,9'}$=6.23 Hz, H-9), 4.10 (q, 1H, $J_{5,6}$=8.43 Hz, H-5), 4.10 (m, 1H, H-8), 4.09 (dd, 1H, H-9'), 3.92 (m, 1H, OCHCH$_2$Si), 3.81 (s, 3H, COOMe), 3.53 (m, 1H, OCH' CH$_2$Si), 3.53 (dd, 1H, H-6), 2.76 (dd, 1H, $J_{3a,3e}$=12.64 Hz, H-3e), 2.10 (t, 1H, H-3a), 1.90 (s, 3H, NAc), 1.41–1.37 (2s, 6H, CMe$_2$), 0.89 (m, 2H, OCH$_2$CH$_2$Si), 0.00 (s, 9H, SiMe$_3$)

Methyl[2-(trimethylsilyl)ethyl 5-acetamido-4-O-benzoyl-3,5-dideoxy-8,9-isopropylidene-7-O-[phenoxy(thiocarbonyl)]-D-glycero-α-D-galacto-2-nonulopyranosid]onate (Compound 20)

Compound 19 (3.05 g, 5.37 mmol) was dissolved in pyridine (140 ml), phenylchlorothiono formate (3.7 ml) was added, and the mixture was stirred at 60° C. for one hour. After a completion of the reaction was confirmed by T.L.C. (dichloromethane:methanol=40:1), the reaction solution was mixed with methanol to decompose excessive reagent and concentrated under reduced pressure. The resultant syrup was extracted with dichloromethane, the organic layer was washed with HCl and H$_2$O, dehydrated with anhydrous sodium sulfate, separated by filtration and concentrated under reduced pressure. The resultant syrup was subjected to column chromatography with an eluting solvent (ethyl acetate:hexane=1:4) to afford Compound 20 (1.83 g, 49.5%).

$C_{34}H_{45}NO_{11}Si$ (687.88)

$^1$H NMR (CDCl$_3$) δ ppm 8.00–7.18 (m, 10H, 2Ph), 6.20 (dd, 1H, $J_{6,7}$=1.83 Hz, $J_{7,8}$=2.93 Hz, H-7), 5.52 (d, 1H, NH), 5.21 (ddd, 1H, $J_{3c,4}$=4.77 Hz, H-4), 4.54 (ddd, 1H, $J_{8,9}$=6.59 Hz, H-8), 4.28 (q, 1H, $J_{4,5}$=$J_{5,NH}$=$J_{5,6}$=10.62 Hz, H-5), 4.24 (dd, 1H, H-6), 4.20 (dd, 1H, $J_{9,9'}$=8.42 Hz, H-9), 4.08 (m, 1H, OCHCH$_2$Si), 3.84 (dd, 1H, H-9'), 3.83 (s, 3H, COOMe), 3.46 (m, 1H, OCH' CH$_2$Si), 2.81 (dd, 1H, $J_{3a,3e}$=12.64 Hz, H-3e), 2.10 (t, 1H, H-3a), 1.73 (s, 3H, NAc), 1.43–1.37 (2s, 6H, CMe$_2$), 0.89 (m, 2H, OCH$_2$CH$_2$Si), 0.00 (s, 9H, SiMe$_3$)

Methyl[2-(trimethylsilyl)ethyl 5-acetamido-4-O-benzoyl-8,9-O-isopropylidene-3,5,7-trideoxy-D-glycero-α-D-galacto-2-nonulopyranosid]onate (Compound 21)

Compound 20 (1.83 g, 2.66 mmol) was dissolved in toluene (92 ml), tributyltin hydride (3.6 ml) and 2,2'-azobisisobutyronitrile (0.110 g) were added and the mixture was heated to 100° C. and stirred at that temperature for one hour. After a completion of the reaction was confirmed by T.L.C. (dichloromethane:methanol=18:1), the reaction solution was concentrated under reduced pressure. The resultant syrup was subjected to column chromatography with an eluting solvent (ethyl acetate:hexane=1:3) to afford Compound 21 (1.36 g, 92.5%).

$C_{27}H_{41}NO_9Si$ (551.71) $[\alpha]_D = -25.54°$ (c=1.472, CHCl$_3$)

IR $\nu^{film}_{max}$cm$^{-1}$: 3700–3150 (NH), 3100–2900 (CH), 1720 (ester), 1660, 1550 (amide), 860, 840 (TMS ethyl), 710 (phenyl)

$^1$H NMR (CDCl$_3$) δ ppm 7.98–7.38 (m, 5H, Ph), 5.62 (d, 1H, $J_{5,NH}$=9.52 Hz, NH), 5.05 (ddd, 1H, $J_{3e,4}$=4.76 Hz, H-4), 4.22 (m, 1H, H-8), 4.14 (dd, 1H, $J_{8,9}$=5.87 Hz, $J_{9,9'}$=7.88 Hz, H-9), 4.13 (dd, 1H, H-9'), 4.05 (q, 1H, $J_{4,5}$=10.63 Hz, $J_{5,6}$=10.25 Hz, H-5), 3.84 (m, 1H, OCHCH$_2$Si), 3.82 (s, 3H, COOMe), 3.64 (dd, 1H, $J_{6,7}$=1.46 Hz, H-6), 3.46 (m, 1H, OCH' CH$_2$Si), 2.77 (dd, 1H, $J_{3a,3e}$=12.64 Hz, H-3e), 2.03 (t, 1H, H-3a), 1.85–1.74 (m, 2H, H-7, H-7'), 1.82 (s, 3H, NAc), 1.43–1.37 (2s, 6H, CMe$_2$), 0.89 (m, 2H, OCH$_2$C$\underline{H_2}$Si), 0.00 (s, 9H, SiMe$_3$)

Methyl[2-(trimethylsilyl)ethyl 5-ethyl 5-acetamido-4-O-benzoyl-3,5,7-trideoxy-D-glycero-α-D-galacto-2-nonulopyranosid]onate (Compound 22)

Compound 21 (1.89 g, 3.43 mmol) was dissolved in 80% acetic acid (25 ml) and the mixture was stirred at room temperature overnight. After a completion of the reaction was confirmed by T.L.C. (dichloromethane:methanol = 18:1), the reaction solution was concentrated under reduced pressure. The resultant syrup was subjected to column chromatography with an eluting solvent (ethyl acetate:hexane = 4:1) to afford Compound 22 (1.47 g, 84.0%).

C$_{24}$H$_{37}$NO$_9$Si (511.65) [α]$_D$= −36.55° (c=1.138, CHCl$_3$)

IR $\nu^{film}{}_{max}$cm$^{-1}$: 3700–3150 (NH, OH), 3100–2900 (CH), 1730 (ester), 1660, 1550 (amide), 860, 840 (TMS ethyl), 710 (phenyl)

$^1$H NMR (CDCl$_3$) δ ppm 8.05–7.27 (m, 5H, Ph), 6.40 (d, 1H, J$_{5,NH}$=9.52 Hz, NH), 5.05 (ddd, 1H, J$_{3e,4}$=4.94 Hz, H-4), 4.17 (q, 1H, J$_{4,5}$=10.17 Hz, H-5), 3.87 (m, 1H, OCHCH$_2$Si), 3.75 (s, 3H, COOMe), 3.46 (m, 1H, OC$\underline{H}'$C$\underline{H_2}$Si), 2.81 (dd, 1H, J$_{3a,3e}$=12.55 Hz, H-3e), 2.06 (t, 1H, H-3a), 1.88 (s, 3H, NAc), 1.84–1.64 (m, 2H, H-7, H-7'), 1.43–1.37 (2s, 6H, CMe$_2$), 0.87 (m, 2H, OC$\underline{H_2}$CH$_2$Si), 0.00 (s, 9H, SiMe$_3$)

Methyl[2-(trimethylsilyl)ethyl 5-acetamido-8,9-di-O-acetyl-4-O-benzoyl-3,5,7-trideoxy-D-glycero-α-D-galacto-2-nonulopyranosid]onate (Compound 23)

Compound 22 (1.43 g, 2.79 mmol) was dissolved in pyridine (30 ml), acetic anhydride (20 ml) was added and the mixture was stirred at room temperature overnight. After a completion of the reaction was confirmed by T.L.C. (dichloromethane:methanol = 18:1), methanol was added to decompose excessive reagent and the reaction solution was concentrated under reduced pressure. The resultant syrup was subjected to column chromatography with an eluting solvent (ethyl acetate:hexane = 2:3) to afford Compound 23 (1.63 g, 98.0%).

C$_{28}$H$_{41}$NO$_{11}$Si (595.72) [α]$_D$= −28.80° (c=1.374, CHCl$_3$)

IR $\nu^{film}{}_{max}$cm$^{-1}$: 3700–3200 (NH), 3100–2900 (CH), 1750 (ester), 1660, 1550 (amide), 860, 840 (TMS ethyl), 720 (phenyl)

$^1$H NMR (CDCl$_3$) δ ppm 7.98–7.38 (m, 5H, Ph), 5.60 (d, 1H, J$_{5,NH}$=7.51 Hz, NH), 5.35 (ddd, 1H, J$_{8,9}$=3.67 Hz, J$_{8,9'}$=5.86 Hz, H-8), 5.01 (ddd, 1H, J$_{3e,4}$=4.77 Hz, H-4), 4.32 (d, 1H, J$_{9,9'}$=11.90 Hz, H-9), 4.06 (q, 1H, J$_{4,5}$=J$_{5,6}$=10.26 Hz, H-5), 4.01 (dd, 1H, H-9'), 3.90 (m, 1H, OCHCH$_2$Si), 3.78 (s, 3H, COOMe), 3.71 (ddd, 1H, J$_{6,7}$=2.38 Hz, H-6), 3.37 (m, 1H, OC$\underline{H}'$ CH$_2$Si), 2.73 (dd, 1H, J$_{3a,3e}$=12.64 Hz, H-3e), 2.09–1.83(3s, 9H, 2Ac, NAc), 2.02–1.78(m, 2H, H-7, H-7'), 0.86(m, 2H, OCH$_2$C$\underline{H_2}$Si), 0.00(s, 9H, SiMe$_3$)

Methyl(5-acetamido-2,8,9-tri-O-acetyl-4-O-benzoyl-3,5,7-trideoxy-D-glycero-D-galacto-2-nonulopyranosid]onate (Compound 25)

Compound 23 (1.63 g, 2.74 mmol) was dissolved in dichloromethane (25 ml), the solution was cooled to −5° C., boron trifluoride diethyl ether (2.8 ml) was added dropwise and the mixture was stirred at that temperature for 9 hrs. After a completion of the reaction was confirmed by T.L.C. (dichloromethane:methanol = 18:1), the reaction solution was extracted with dichloromethane. The organic layer was washed with sodium bicarbonate and H$_2$O, dehydrated with anhydrous sodium sulfate, separated by filtration and concentrated under reduced pressure. The resultant syrup was dissolved in acetic anhydride (12.5 ml), cooled and pyridine (11 ml) was added dropwise and stirred at room temperature overnight. After a completion of the reaction was confirmed by T.L.C. (dichloromethane:methanol = 18:1), methanol was added to decopose excessive reagent and the reaction solution was concentrated under reduced pressure. The resultant syrup was subjected to column chromatography with an eluting solvent (ethyl acetate:hexane = 1:1) to afford Compound 25 (1.29 g, 87.8%).

C$_{25}$H$_{31}$NO$_{12}$ (537.52) [α]$_D$= −44.48° (c=0.980, CHCl$_3$)

IR $\nu^{film}{}_{max}$cm$^{-1}$: 3700–3150 (NH), 3100–2950 (CH), 1740 (ester), 1660, 1540 (amide), 710 (phenyl)

Methyl(methyl 5-acetamido-8,9-di-O-acetyl-4-O-benzoyl-3,5,7-trideoxy-2-thio-D-glycero-D-galacto-2-nonulopyranosid]onate (Compound 26)

Compound 25 (1.29 g, 2.40 mmol) was dissolved in dichloroethane (25 ml) and cooled to 0° C. TMS-SMe (1.4 ml) and TMS-OTf (0.7 ml) were added at 0° C. and the mixture was stirred at 50° C. for 5.5 hrs. After a completion of the reaction was confirmed by T.L.C. (dichloromethane:methanol = 18:1), the reaction solution was extracted with dichloromethane. The organic layer was washed with sodium carbonate and then H$_2$O, dehydrated with anhydrous sodium sulfate, filtered and concentrated under reduced pressure. The resultant syrup was subjected to column chromatography wtih an eluting solvent (ethyl acetate:hexane = 2:3) to afford Compound 26 (0.96 g, 76.2%).

C$_{24}$H$_{31}$NO$_{10}$S (525.57) [α]$_D$= −70.37° (c=1.080, CHCl$_3$)

IR $\nu^{film}{}_{max}$cm$^{-1}$: 3700–3150 (NH), 3100–2950 (CH), 1740 (ester), 1660, 1550 (amide), 710 (phenyl)

2-(Trimethylsilyl)ethyl O-(methyl 5-acetamido-8,9-di-O-acetyl-4-O-benzoyl-5,7-dideoxy-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 2A)

Compound 26 (490 mg, 0.93 mmol) and Compound 16 (360 mg, 0.48 mmol) was dissolved in acetonitrile (6 ml), Molecular Sieves 3A (1 g) was added and the mixture was stirred overnight. After cooling to −15° C., dimethyl(methylthio)sulfonium triflate (77%, 1.3 g) was added and the mixture was stirred at −15° C. for 2 days. After a completion of the reaction was confirmed by T.L.C. (dichloromethane:methanol = 20:1), the reaction solution was filtered through Celite and extracted with dichloromethane. The organic layer was washed with successive sodium carbonate and water, dehydrated with anhydrous sodum sulfate, filtered and concentrated under reduced pressure. The resultant syrup was subjected to column chromatography with an eluting solvent (dichloromethane:methanol = 100:1) to afford Compound 2A (200 mg, 34.2%).

C$_{61}$H$_{73}$NO$_{24}$Si (1,232.33) [α]$_D$= +1.89° (c=0.422, CHCl$_3$)

IR $\nu^{film}_{max}$cm$^{-1}$: 3700-3150 (NH, OH), 3100-2900 (CH), 1720 (ester), 1660, 1540 (amide), 850, 830 (TMS ethyl), 710 (phenyl)

$^1$H NMR (CDCl$_3$) δ ppm

Neu5Ac unit: 5.49 (m, 1H, H-8), 5.24 (ddd, 1H, J$_{3e,4}$=4.58 Hz, H-4), 3.92 (s, 3H, COOMe), 3.68 (m, 1H, H-6), 2.95 (dd, 1H, J$_{3a,3c}$=12.64 Hz, H-3e), 2.29 (t, 1H, H-3a), 2.16-1.97 (3s, 9H, 2OAc, NAc), 2.09-1.84 (m, 2H, H-7, H-7')

Lac unit: 8.19-7.35 (m, 20H, 4Ph), 5.37 (t, 1H, H-2), 4.88 (dd, 1H, J$_{gem}$=12.37 Hz, J$_{5,6}$=3.30 Hz, H-6), 4.77 (d, 1H, J$_{1,2}$=8.06 Hz, H-1), 4.69 (d, 1H, J$_{1',2'}$=7.33 Hz, H-1'), 4.41 (dd, 1H, H-6), 3.68 (m, 1H, OCHCH$_2$Si), 0.99 (m, 2H, OCH$_2$CH$_2$Si), 0.00 (s, 3H, SiMe$_3$)

2-(Trimethylsilyl)ethyl O-(methyl 5-acetamido-8,9-di-O-acetyl-4-O-benzoyl-3,5,7-trideoxy-D-glycero-α-D-galacto-2-nonulopyranosylonate)-(2→3)-O-(2,4-di-O-acetyl-6-O-benzoyl-β-D-galactopyranosyl)-(1→3)-3-O-acetyl-2,6-di-O-benzoyl-β-D-glucopyranoside (Compound 2B)

Compound 2A (200 mg, 0.16 mmol) was dissolved in pyridine (13 ml), acetic anhydride (10 ml) was added and the mixture was stirred at room temperature overnight. After a completion of the reaction was confirmed by T.L.C. (toluene:methanol=7:1), methanol was added to decompose excessive reagent and concentrated under reduced pressure. The resultant syrup was subjected to column chromatography with an eluting solvent (ethyl acetate:hexane=2:1) to afford Compound 2B (210 mg, 95.5%).

C$_{67}$H$_{79}$NO$_{27}$Si (1,358.44) [α]$_D$=−0.61° (c=1.291, CHCl$_3$)

IR $\nu^{film}_{max}$cm$^{-1}$: 3700-3200 (NH), 3100-2900 (CH), 1740 (ester), 1670, 1540 (amide), 860, 840 (TMS ethyl), 710 (phenyl)

$^1$H NMR (CDCl$_3$) δ ppm

Neu5Ac unit: 5.67 (m, 1H, H-8), 5.66 (d, 1H, J$_{5,NH}$=9.53 Hz, NH), 5.18 (m, 1H, H-4), 3.86 (s, 3H, COOMe), 3.49 (m, 1H, H-6), 2.85 (dd, 1H, J$_{3a,3e}$=12.27 Hz, J$_{3e,4}$=4.76 Hz, H-3e), 2.31-1.96 (6s, 18H, 5OAc, NAc), 2.05-1.89 (m, 2H, H-7, H-7')

Lac unit: 8.18-7.39 (m, 20H, 4Ph), 5.64 (t, 1H, J$_{2,3}$=9.35 Hz, H-3), 5.33 (t, 1H, H-2), 5.18 (d, 1H, J$_{3',4'}$=3.30 Hz, H-4'), 5.17 (m, 1H, H-2'), 5.02 (d, 1H, J$_{1',2'}$=8.06 Hz, H-1'), 4.80 (dd, 1H, H-3'), 4.78 (d, 1H, J$_{1,2}$=7.69 Hz, H-1), 4.56 (dd, 1H, J$_{gem}$=11.73 Hz, J$_{5,6}$=3.67 Hz, H-6), 3.67 (m, 1H, OCHCH$_2$Si), 0.98 (m, 2H, OCH$_2$CH$_2$Si), 0.00 (s, 3H, SiMe$_3$)

O-(Methyl 5-acetamido-8,9-di-O-acetyl-4-O-benzoyl-3,5,7-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 2C)

Compound 2B (210 mg, 0.15 mmol) was dissolved in dichloromethane (4 ml), boron trifluoride diethyl ether (0.24 ml) was added dropwise under ice-cooling and the mixture was stirred at 0° C. for 8.5 hrs. After a completion of the reaction was confirmed by T.L.C. (dichloromethane:methanol=18:1), the reaction solution was extracted with dichloromethane. The organic layer was washed with successive, sodium carbonate and H$_2$O, dehydrated with anhydrous sodium sulfate, filtered and concentrated under reduced pressure. The resultant syrup was subjected to column chromatography with an eluting solvent (dichloromethane:methanol=70:1) to afford Compound 2C (182 mg, 93.3%).

C$_{62}$H$_{67}$NO$_{27}$ (1,258.20) [α]$_D$=+27.53° (c=1.438, CHCl$_3$)

IR $\nu^{film}_{max}$cm$^{-1}$: 3700-3150 (NH, OH), 3100-2950 (CH), 1730 (ester), 1660, 1540 (amide), 710 (phenyl)

O-(Methyl 5-acetamido-8,9-di-O-acetyl-4-O-benzoyl-3,5,7-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 2D)

Compound 2C (182 mg, 0.14 mmol) was dissolved in dichloromethane (2.5 ml), trichloroacetonitrile (0.5 ml) and 1,5-diazabicyclo[5.4.0]-undec-7-ene (20 mg) were added under ice-cooling and the mixture was stirred at 0° C. for 2 hrs. After a completion of the reaction was confirmed by T.L.C. (dichloromethane:methanol=18:1), the reaction solution was concentrated under reduced pressure. The resultant syrup was subjected to column chromatography with an eluting solvent (dichloromethane:methanol=85:1) to afford Compound 2D (180 mg, 88.7%).

C$_{65}$H$_{67}$N$_2$O$_{27}$Cl$_3$ (1,402.59) [α]$_D$=+32.00° (c=0.950, CHCl$_3$)

IR $\nu^{film}_{max}$cm$^{-1}$: 3700-3150 (NH), 3100-2950 (CH), 1730 (ester), 1680, 1540 (amide), 710 (phenyl)

$^1$H NMR (CDCl$_3$) δ ppm

Neu5Ac unit: 5.54 (m, 1H, H-8), 5.51 (d, 1H, J$_{5,NH}$=8.98 Hz, NH), 5.09 (m, 1H, H-4), 3.92 (q, 1H, J$_{4,5}$=J$_{5,6}$=10.26 Hz, H-5), 3.75 (s, 3H, COOMe), 3.34 (m, 1H, H-6), 2.73 (dd, 1H, J$_{3a,3e}$=12.36 Hz, J$_{3e,4}$=4.67 1 Hz, H-3e), 2.18-1.83 (6s, 18H, 5OAc, NAc), 2.04-1.82 (m, 2H, H-7, H-7')

Lac unit: 8.54 (s, 1H, C=NH), 8.07-7.22 (m, 20H, 4Ph), 6.67(d, 1H, J$_{1,2}$=3.76 Hz, H-1), 5.86 (t, 1H, J$_{2,3}$=10.26 Hz, H-3), 5.28 (dd, 1H, H-2), 5.07 (m, 2H, H-2', H-4'), 4.95 (d, 1H, J$_{1',2'}$=8.24 Hz, H-1'), 4.69 (dd, 1H, J$_{3',4'}$=3.20 Hz, H-3')

O-(Methyl 5-acetamido-8,9-di-O-acetyl-4-O-benzoyl-3,5,7-trideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-benzoyl-4-octadecene-1,3-diol (Compound 2E)

Compound 2D (110 mg, 0.08 mmol) and Compound 17 (90 mg, 0.19 mmol) were dissolved in dichloromethane (3.5 ml), Molecular Sieves 4A type AW 300 (2.5 g) was added and the mixture was stirred at room temperature for 30 minutes. Then boron trifluoride diethyl ether (0.05 ml) was added dropwise under ice-cooling and the mixture was stirred at 0° C. for 2 hrs. After a completion of the reaction was confirmed by T.L.C. (dichloromethane:methanol=18:1), the reaction solution was filtered through Celite and extracted with dichloromethane. The organic layer was washed with successive sodium carbonate and water, dehydrated with anhydrous sodium sulfate, filtered and concentrated under reduced pressure. The resultant syrup was subjected to column chromatography with an eluting solvent (ethyl acetate: hexane=1:1) to afford Compound 2E (60 mg, 45.8%).

C$_{87}$H$_{104}$N$_4$O$_{29}$ (1,669.79) [α]$_D$=−8.33° (c=0.720, CHCl$_3$)

IR $\nu^{film}_{max}$ cm$^{-1}$: 3700-3150 (NH), 3100-2850 (CH), 2100 (N$_3$), 1730 (ester), 1660, 1540 (amide), 710 (phenyl)

$^1$H NMR (CDCl$_3$) δ ppm

Neu5Ac unit: 5.46 (m, 1H, H-8), 4.99 (m, 1H, H-4), 4.01 (q, 1H, J$_{5,6}$=10.32 Hz, H-5), 3.67 (s, 3H, COOMe), 3.29 (ddd, 1H, H-6), 2.65 (dd, 1H, J$_{3a,3e}$=12.64 Hz, J$_{3e,4}$=4.58 Hz, H-3e), 2.10-1.77 (6s, 18H, 5OAc, NAc), 1.87-1.63 (m, 2H, H-7, H-7')

Lac unit: 7.99-7.19 (m, 20H, 4Ph), 5.42 (t, 1H, J$_{2,3}$=9.90 Hz, H-3), 5.17 (dd, 1H, H-2), 4.99 (m, 2H, J$_{3', 4'}$=3.31 Hz, H-4'), 4.97 (t, 1H, J$_{2', 3'}$=10.06 Hz, H-2'), 4.83 (d, 1H, J$_{1', 2'}$=7.88 Hz, H-1'), 4.61 (d, 1H, J$_{1,2}$=7.97 Hz, H-1), 4.60 (dd, 1H, H-3'), 4.36 (dd, 1H, J$_{gem}$=11.54 Hz, H-6)

Sphingosine unit: 5.60 (dt, 1H, J$_{5,6}$=J$_{5,6'}$=6.59 Hz, H-5), 5.47 (dd, 1H, J$_{4,5}$=8.43 Hz, H-4), 1.18 (s, 22H, 11CH$_2$), 0.81 (t, 3H, CH$_3$)

O-(Methyl 5-acetamido-8,9-di-O-acetyl-4-O-benzoyl-3,5,7-trideoxy-D-glycero-α-D-galacto-2-nonulopyranos ylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-benzoyl-2-octadecanamide-4-octadecene-1,3-diol (Compound 2F)

Compound 2E (60 mg, 0.04 mmol) was dissolved in a mixed solvent of 5/1 pyridine/water (6 ml) and the solution was stirred at 0° C. for 6 days while blowing hydrogen sulfide gas. After a completion of the reaction was confirmed by T.L.C. (ethyl acetate), the reaction solution was evaporated under reduced pressure to dryness. The solid was dissolved in dichloromethane (4 ml), stearic acid (50 mg, 0.18 mmol) and WSC (50 mg) were added and the mixture was stirred at room temperature overnight. After a completion of the reaction was confirmed by T.L.C. (dichloromethane:methanol=18:1), the reaction solution was extracted with dichloromethane. The organic layer was washed with water, dehydrated with anhydrous sodium sulfate, filtered and concentrated under reduced pressure. The resultant syrup was subjected to column chromatography with an eluting solvent (dichloromethane:methanol=110:1) to afford Compound 2F (54 mg, 78.3%).

C$_{105}$H$_{140}$N$_2$O$_{30}$ (1.910.26) [α]$_D$=+8.33° (c=1.096, CHCl$_3$)

IR $\nu^{film}_{max}$ cm$^{-1}$: 3700-3150 (NH), 3100-2850 (CH), 1730 (ester), 1670, 1540 (amide), 710 (phenyl)

$^1$H NMR (CDCl$_3$) δ ppm

Neu5Ac unit: 5.66 (d, 1H, NH), 5.48 (m, 1H, H-8), 5.05 (m, 1H, H-4), 3.74 (s, 3H, COOMe), 3.36 (m, 1H, H-6), 2.72 (dd, 1H, J$_{3a,3e}$=12.28 Hz, J$_{3e,4}$=4.58 Hz, H-3e), 2.15-1.84 (6s, 18H, 5OAc, NAc), 1.95-1.76 (m, 2H, H-7, H-7')

Lac unit: 8.07-7.27 (m, 20H, 4Ph), 5.52 (t, 1H, J$_{2,3}$=9.71 Hz, H-3), 5.18 (dd, 1H, H-2), 5.06 (m, 2H, J$_{3', 4'}$=3.12 Hz, H-4'), 5.02 (t, 1H, J$_{2', 3'}$=9.90 Hz, H-2'), 4.87 (d, 1H, J$_{1', 2'}$=7.69 Hz, H-1'), 4.68 (dd, 1H, H-3'), 4.61 (d, 1H, J$_{1,2}$=7.70 Hz, H-1), 4.45 (dd, 1H, J$_{gem}$=12.09 Hz, H-6)

Cer unit: 5.77 (dt, 1H, J$_{5,6}$=J$_{5,6'}$=6.96 Hz, H-5), 1.26 (s, 50H, 25CH$_2$), 0.88 (t, 6H, 2CH$_3$)

O-(5-Acetamido-3,5,7-trideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-2-octadecanamide-4-octadecene-1,3-diol (Compound 2)

Compound 2F (54 mg, 0.03 mmol) was dissolved in methanol (2 ml), 28% sodium methylate solution (5 drops) was added and the mixture was stirred at room temperature for 18 hrs. Water (0.5 ml) was added and the mixture was stirred for further 6 hrs. After a completion of the reaction was confirmed by T.L.C. (butanol:ethanol:water=4:2:1), the reaction solution was neutralized with ion exchange resin IR-120 (H+), filtered and concentrated under reduced pressure. The resultant syrup was subjected to gel filtration with Sephadex LH-20 to afford Compound 2 (32 mg, quant.).

C$_{59}$H$_{108}$N$_2$O$_{20}$ (1,165.51) [α]$_D$=−9.23° (c=0.736, CHCl$_3$:MeOH=1:1)

$^1$H NMR (CDCl$_3$) δ ppm

Neu5Ac unit: 2.78 (broad, 1H, H-3e)

Lac unit: 4.43 (d, 1H, J$_{1', 2'}$=7.51 Hz, H-1'), 4.31 (d, 1H, J$_{1,2}$=7.51 Hz, H-1)

Cer unit: 5.69 (dt, 1H, J$_{5,6}$=J$_{5,6'}$=6.59 Hz, H-5), 5.45 (dd, 1H, J$_{4,5}$=15.20 Hz, H-4), 1.28 (s, 50H, 25CH$_2$), 0.89 (t, 6H, 2CH$_3$)

EXAMPLE 3

Methyl[2-(trimethylsilyl)ethyl 5-acetamido-4-O-acetyl-8,9-O-isopropylidene-3,5-dideoxy-D-glycero-α-D-galacto-2-nonulopyranosid]onate (Compound 27)

Compound 18 (3.50 g, 7.55 mmol) was dissolved in a mixed solvent of pyridine (50 ml) and dichloromethane (30 ml) and cooled to −35° C. Then acetyl chloride (1.8 ml) diluted with dichloromethane (18 ml) was added dropwise and the mixture was stirred as such for 5 hrs. After a completion of the reaction was confirmed by T.L.C. (dichloromethane:methanol=18:1), methanol was added to decompose excessive reagent, the mixture was stirred for further 30 minutes, concentrated under reduced pressure and extracted with dichloromethane. The organic layer was washed with successive HCl and H$_2$O, dehydrated with anhydrous sodium sulfate, filtered and concentrated under reduced pressure. The resultant syrup was subjected to column chromatography with an eluting solvent (ethyl acetate:hexane=2:3) to afford Compound 27 (3.43 g, 89.8%).

C$_{22}$H$_{39}$NO$_{10}$Si (505.64) [α]$_D$=−32.90° (c=1.848, CHCl$_3$)

IR $\nu^{film}_{max}$ cm$^{-1}$: 3700-3150 (NH,OH), 3100-2900 (CH), 1740 (ester), 1660, 1540 (amide), 850, 830 (TMS ethyl)

$^1$H NMR (CDCl$_3$) δ ppm 6.02 (d, 1H, J$_{5,NH}$=7.32 Hz, NH), 5.00 (ddd, 1H, J$_{3e,4}$=5.13 Hz, H-4), 4.34 (dd, 1H, J$_{9,9'}$=12.45 Hz, J$_{8,9}$=6.23 Hz, H-9), 4.08 (m, 2H, H-7, H-8), 3.94 (q, 1H, J$_{4,5}$=J$_{5,6}$=10.44 Hz, H-5), 3.92 (dd, 1H, J$_{8,9'}$=2.38 Hz, H-9'), 3.89 (m, 1H, OCH$_2$Si), 3.80 (s, 3H, COOMe), 3.51 (m, 1H, OCH' CH$_2$Si), 3.43 (dd, 1H, J$_{6,7}$=1.28 Hz, H-6), 2.63 (dd, 1H, J$_{3a,3e}$=12.73 Hz, H-3e), 2.09-1.97 (2s, 6H, OAc, NAc), 1.40-1.37 (2s, 6H, CMe$_2$), 0.89 (m, 2H, OCH$_2$CH$_2$Si), 0.00 (s, 9H, SiMe$_3$) cl Methyl[2-(trimethylsilyl)ethyl 5-acetamido-4-O-acetyl-3,5-dideoxy-D-glycero-α-D-galacto-2-nonulopyranosid]onate (Compound 28)

Compound 27 (3.35 g, 6.63 mmol) was dissolved in 80% acetic acid (25 ml) and the solution was allowed to stand at room temperature overnight. After a completion of the reaction was confirmed by T.L.C. (dichloromethane:methanol=10:1), the reaction solution was concentrated under reduced pressure. The resultant syrup was subjected to column chromatography with an eluting solvent (ethyl acetate) to afford Compound 28 (2.94 g, 95.5%).

$C_{19}H_{35}NO_{20}Si$ (4.65.57) $[\alpha]_D=-28.59°$ (c=1.042, $CHCl_3$)

IR $\nu^{film}_{max}$cm$^{-1}$: 3700–3150 (NH, OH), 3100–2900 (CH), 1740 (ester), 1660, 1560 (amide), 860, 840 (TMS ethyl)

$^1$H NMR ($CDCl_3$) δ ppm 6.45 (d, 1H, NH), 4.94 (ddd, 1H, $J_{3e,4}$=5.13 Hz, H-4), 3.96 (q, 1H, $J_{4,5}$=$J_{5,NH}$=$J_{5,6}$=10.44 Hz, H-5), 3.87 (s, 3H, COOMe), 3.42 (m, 1H, OCHCH$_2$Si), 2.69 (dd, 1H, $J_{3a,3e}$=12.97 Hz, H-3e), 2.10–2.00 (2s, 6H, OAc, NAc), 0.88 (m, 2H, OCH$_2$CH$_2$Si), 0.00 (s, 9H, SiMe$_3$)

Methyl[2trimethylsilyl)ethyl 5acetamido-4,9-di-O-acetyl-3,5-dideoxy-D-glycero-α-D-galacto-2-nonulopyranosid]onate (Compound 29)

Compound 28 (2.91 g, 6.25 mmol) was dissolved in a mixed solvent of pyridine (25 ml) and dichloromethane (30 ml) and the solution was cooled to −45° C. AcCl (1.5 ml) diluted with dichloromethane (16 ml) was added dropwise and the mixture was stirred as such for 30 minutes. After a completion of the reaction was confirmed by T.L.C. (dichloromethane:methanol=10:1), methanol was added to decompose excessive reagent and the mixture was stirred for further 30 minutes, concentrated under reduced pressure and extracted with dichloromethane. The organic layer was washed with successive HCl and H$_2$O, dehydrated with anhydrous sodium sulfate, filtered and concentrated under reduced pressure. The resultant syrup was subjected to column chromatography with an eluting solvent (dichloromethane:methanol=50:1) to afford Compound 29 (1.99 g, 62.8%).

$C_{21}H_{37}NO_{11}Si$ (507.61) $[\alpha]_D=-30.58°$ (c=1.020, $CHCl_3$)

IR $\nu^{film}_{max}$cm$^{-1}$: 3700–3150 (NH, OH), 3100–2900 (CH), 1740 (ester), 1660, 1550 (amide), 860, 840 (TMS, ethyl)

$^1$H NMR ($CDCl_3$) δ ppm 6.04 (d, 1H, $J_{5,NH}$=7.88 Hz, NH), 4.90 (ddd, 1H, $J_{3e,4}$=4.94 Hz, H-4), 4.47 (dd, 1H, $J_{8,9}$=2.02 Hz, $J_{9,9'}$=11.36 Hz, H-9), 4.20 (dd, 1H, $J_{8,9'}$=6.60 Hz, H-9'), 4.10 (m, 1H, H-8), 3.91 (m, 1H, OCHCH$_2$Si), 3.85 (s, 3H, COOMe), 3.47 (dd, 1H, $J_{5,6}$=10.62 Hz, $J_{6,7}$=2.56 Hz, H-6), 3.39 (m, 1H, OCH' CH$_2$Si), 2.68 (dd, 1H, $J_{3a,3e}$=13.00 Hz, H-3e), 2.11–1.99 (3s, 9H, 2OAc, NAc), 0.88 (m, 2H, OCH$_2$CH$_2$Si), 0.00 (s, 9H, SiMe$_3$)

Methyl[2-(trimethylsilyl)ethyl 5-acetamido-4,9-di-O-acetyl-3,5-dideoxy-8-O-[phenoxy(thiocarbonyl)]-D-glycero-α-D-galacto-2-nonulopyranosid]onate (Compound 30)

Compound 29 (1.99 g, 3.92 mmol) was dissolved in a mixed solvent of pyridine (35 ml) and dichloromethane (35 ml), phenylchlorothiono formate (1.4 ml) was added and the mixture was stirred at room temperature for 3.5 hrs. After a completion of the reaction was confirmed by T.L.C. (dichloromethane:methanol=18:1), methanol was added to decompose excessive reagent. Then the reaction solution was concentrated under reduced pressure and extracted with dichloromethane. The organic layer was washed with successive HCl and H$_2$O, dehydrated with anhydrous sodium sulfate, filtered and concentrated under reduced pressure. The resultant syrup was subjected to column chromatography with an eluting solvent (ethyl acetate:hexane=2:3) to afford Compound 30 (1.76 g, 71.5%).

$C_{27}H_{41}NO_9Si$ (551.71) $[\alpha]_D=+7.16°$ (c=1.060, $CHCl_3$)

IR $\nu^{film}_{max}$cm$^{-1}$: 3700–3150 (NH, OH), 3100–2900 (CH), 1750 (ester), 1660, 1550 (amide), 860, 840 (TMS ethyl)

$^1$H NMR ($CDCl_3$) δ ppm 7.48–7.28 (m, 5H, Ph), 6.08 (d, 1H, NH), 5.81 (m, 1H, H-8), 4.99 (ddd, 1H, $J_{3e,4}$=4.77 Hz, H-4), 4.91 (dd, 1H, $J_{8,9}$=2.38 Hz, $J_{9,9'}$=12.64 Hz, H-9), 4.49 (dd, 1H, $J_{8,9'}$=3.48 Hz, H-9'), 4.16 (d, 1H, $J_{7,7\text{-}OH}$=7.14 Hz, 7-OH), 4.16 (m, 1H, OCHCH$_2$Si), 4.04 (1, 1H, $J_{4,5}$=$J_{5,NH}$=$J_{5,6}$=10.44 Hz, H-5), 3.88 (s, 3H, COOMe), 3.86 (dd, 1H, $J_{6,7}$=1.65 Hz, H-6), 3.32 (m, 1H, OCH' CH$_2$Si), 2.67 (dd, 1H, $J_{3a,3e}$=12.82 Hz, H-3e), 2.15–2.96 (3s, 9H, 2OAc, NAc), 0.88 (m, 2H, OCH$_2$CH$_2$Si), 0.00 (s, 9H, SiMe$_3$)

Methyl[2-(trimethylsilyl)ethyl 5-acetamido-4,9-di-O-acetyl-3,5,8-trideoxy-D-glycero-α-D-galacto-2-nonulopyranosid]onate (Compound 31)

Compound 30 (1.76 g, 2.80 mmol) was dissolved in toluene (80 ml), tributyltin hydride (5.8 ml) and 2,2'-azobisisobutyronitrile (0.155 g) were added and the mixture was heated to 100° C. with the attached cooling tube and stirred at that temperature for 2.5 hrs. After a completion of the reaction was confirmed by T.L.C. (dichloromethane;methanol=18:1), the reaction solution was concentrated under reduced pressure. The resultant syrup was subjected to column chromatography with an eluting solvent (ethyl acetate:hexane=4:5) to afford Compound 31 (1.20 g, 87.0%).

$C_{21}H_{37}NO_{10}Si$ (491.61) $[\alpha]_D=-31.46°$ (c=1.354, $CHCl_3$)

IR $\nu^{film}_{max}$cm$^{-1}$: 3700–3150 (NH, OH), 3100–2900 (CH), 1740 (ester), 1660, 1540 (amide), 860, 840 (TMS ethyl)

$^1$H NMR ($CDCl_3$) δ ppm 6.03 (d, 1H, $J_{5,NH}$=8.06, NH), 4.93 (ddd, 1H, $J_{3e,4}$=4.77 Hz, H-4), 4.40 (d, 1H, $J_{7,7\text{-}OH}$=4.58, 7-OH), 4.35–4.18(m, 2H, H-9, H-9'), 3.93 (q, 1H, $J_{4,5}$=10.44 Hz, $J_{5,6}$=10.26 Hz, H-5), 3.81 (s, 3H, COOMe), 3.67 (m, 1H, H-7), 3.44 (m, 1H, OCHCH$_2$Si), 2.62 (dd, 1H, $J_{3a,3e}$=12.64 Hz, H-3e), 2.09–1.99 (3s, 9H, 2Ac, NAc), 2.00–1.85 (m, 2H, H-8, H-8'), 0.89 (m, 2H, OCH$_2$CH$_2$Si), 0.00 (s, 9H, SiMe$_3$)

Methyl[2-(trimethylsilyl)ethyl 5-acetamido-4,7,9-tri-O-acetyl-3,5,8-trideoxy-D-glycero-α-D-galacto-2-nonulopyranosid]onate (Compound 32)

Compound 31 (1.80 g, 3.90 mmol) was dissolved in pyridine (25 ml), acetic anhydride (20 ml) was added and the mixture was stirred at room temperature overnight. After a completion of the reaction was confirmed by T.L.C. (dichloromethane:methanol=18:1), methanol was added to decompose excessive reagent and the reaction solution was concentrated under reduced pressure. The resultant syrup was subjected to column chromatography with an eluting solvent (ethyl acetate:hexane=1:1) to afford Compound 32 (1.78 g, 91.3%).

$C_{23}H_{39}NO_{11}Si$ (533.65) $[\alpha]_D=-24.01°$ (c=0.916, $CHCl_3$)

IR $\nu^{film}_{max}$cm$^{-1}$: 3700–3150 (NH), 3100–2900 (CH), 1740 (ester), 1660, 1540 (amide), 860, 840 (TMS ethyl)

¹H NMR (CDCl₃) δ ppm 5.32 (d, 1H, $J_{5,NH}$=9.89 Hz, NH), 5.08 (ddd, 1H, $J_{7,8}$=4.76 Hz, H-7), 4.85 (ddd, 1H, $J_{3e,4}$=4.77 Hz, $J_{4,5}$=10.26 Hz, H-4), 4.27–4.03 (m, 2H, H-9, H-9'), 4.11 (q, 1H, H-5), 3.88 (m, 1H, OCHCH₂Si), 3.81(s, 3H, COOMe), 3.78(dd, 1H, $J_{6,7}$=2.01 Hz, H-6), 3.45 (m, 1H, OCH' CH₂Si), 2.59(dd, 1H, $J_{3a,3e}$=12.64 Hz, H-3e), 2.08–2.02(3s, 9H, 2OAc, NAc), 2.06–1.89(m, 2H, H-8, H-8'), 0.88(m, 2H, OCH₂CH₂Si), 0.00(s, 9H, SiMe₃)

Methyl(5-acetamido-2,4,7,9-tetra-O-acetyl-3,5,8-trideoxy-D-glycero-D-galacto-2-nonulopyranosid)onate (Compound 34)

Compound 32 (1.78 g, 3.34 mmol) was dissolved in dichloromethane (25 ml), the solution was cooled to 0° C., boron trifluoride diethyl ether (5.3 ml) was added dropwise and the mixture was stirred at that temperature for 12.5 hrs. After a completion of the reactoin was confirmed by T.L.C. (dichloromethane:methanol=10:1), methanol was added to decompose excessive reagent and the reaction solution was concentrated under reduced pressure. The resultant syrup was subjected to column chromatography with an eluting solvent (ethyl acetate: hexane=1:1) to afford Compound 34 (1.34 g, 84.3%).

$C_{20}H_{29}NO_{12}$ (475.45) [α]$_D$− =40.90° (c=0.880, CHCl₃)

IR $\nu^{film}_{max}$cm⁻¹: 3700–3150 (NH), 3100–2950 (CH), 1740 (ester), 1660, 1540 (amide)

Methyl(methyl 5-acetamido-4,7,9-tri-O-acetyl-3,5,8-tridexoy-2-thio-D-glycero-D-galacto-2-nonulopyranosid) onate (Compound 35)

Compound 34 (1.29 g, 2.71 mmol) was dissolved in dichloroethane (25 ml) and cooled to 0° C. TMS-SMe (2.3 ml) and TMS-OTf (0.8 ml) were added and the mixture was stirred at 40° C. for 2 hrs. After a completion of the reaction was confirmed by T.L.C. (dichloromethane:methanol=18:1), the reaction solution was extracted with dichloromethane. The organic layer was washed with successive sodium carbonate and water, dehydrated with anhydrous sodium sulfate, filtered and concentrated under reduced pressure. The resultant syrup was subjected to column chromatography with an eluting solvent (ethyl acetate:hexane=5:4) to afford Compound 35 (1.25 g).

$C_{19}H_{29}NO_{10}S$(463.50) [α]$_D$= −56.70° (c=0.850, CHCl₃)

IR $\nu^{film}_{max}$cm⁻¹: 3700–3150 (NH), 3100–2950 (CH), 1740 (ester), 1660, 1540 (amide)

2-Trimethylsilyl)ethyl O-(methyl 5acetamido-4,7,9-tri-O-acetyl-3,5,8-trideoxy-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 3A)

Compounds 35 (806 mg, 1.74 mmol) and Compound 16 (656 mg, 0.87 mmol) were dissolved in acetonitrile (8 ml), Molecular Sieves 3A (1.5 g) was added and the mixture was stirred overnight. After cooling to −15° C., dimethyl(methylthio)sulfonium triflate (77%, 2.3 g) was added and the mixture was stirred at −15° C. for 2 days. After a completion of the reaction was confirmed by T.L.C. (dichloromethane:methanol=25:1), the reaction solution was filtered through Celite and extracted with dichloromethane. The organic layer was washed with successive sodium carbonate and water, dehydrated with anhydrous sodium sulfate, filtered and concentrated under reduced pressure. The resultant syrup was subjected to column chromatography with an eluting solvent (toluene:methanol=30:1) to afford Compound 3A (360 mg, 35.4%).

$C_{56}H_{71}NO_{24}Si$ (1,170.26) [α]$_D$= −0.36° (c=1.660, CHCl₃)

IR $\nu^{film}_{max}$cm⁻¹: 3700–3150 (NH, OH), 3100–2900 (CH), 1730 (ester), 1670, 1540 (amide), 860, 840 (TMS ethyl), 710 (phenyl)

¹H NMR (CDCl₃) δ ppm

Neu5Ac unit: 5.69 (d, 1H, $J_{5,NH}$=8.97 Hz, NH), 5.18–5.07 (m, 2H, H-4, H-7), 3.92 (s, 3H, COOMe), 3.57 (m, 1H, H-6), 2.85 (dd, 1H, $J_{3a,3e}$=13.09 Hz, $J_{3e,4}$=4.67 Hz, H-3e), 2.22–2.00 (4s, 12H, 3O Ac, NAc), 2.06–1.92 (m, 2H, H-8, H-8')

Lac unit: 8.20–7.07 (m, 15H, 3Ph), 5.37 (t, 1H, $J_{2,3}$=9.53 Hz, H-2), 4.85 (dd, 1H, H-6), 4.76(d, 1H, $J_{1,2}$=8.15 Hz, H-1), 4.56(d, 1H, $J_{1',2'}$=7.88 Hz, H-1'), 4.51 (dd, 1H, H-6), 3.67 (m, 1H, OCHCH₂Si), 0.99 (m, 2H, OCH₂CH₂Si), 0.00 (s, 9H, SiMe₃)

2-(Trimethylsilyl)ethyl O-methyl 5-acetamido-4,7,9-tri-O-acetyl-3,5,8-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 3B)

Compound 3A (360 mg, 0.31 mmol) was dissolved in pyridine (15 ml), acetic anhydride (12 ml) was added and the mixture was stirred at room temperature overnight. After a completion of the reaction was confirmed by T.L.C. (toluene:methanol=7:1), methanol was added to decompose excessive reagent and concentrated under reduced pressure. The resultant syrup was subject to column chromatography with an eluting solvent (ethyl acetate:hexane=2:1) to afford Compound 3B (333 mg, 83.5%).

$C_{62}H_{77}NO_{27}Si$ (1,296.37) [α]$_D$= +1.36° (c=1.906, CHCl₃)

IR $\nu^{film}_{max}$cm⁻¹: 3700–3200 (NH), 3100–2900 (CH), 1740 (ester), 1690, 1540 (amide), 860, 840 (TMS ethyl), 720 (phenyl)

¹H NMR (CDCl₃) δ ppm

Neu5Ac unit: 5.19 (m, b 1H, H-7), 4.86 (d, 1H, NH), 4.16 (q, 1H, $J_{4,5}$=$J_{5,NH}$=$J_{5,6}$=10.54 Hz, H-5), 3.88 (s, 3H, COOMe), 3.47 (dd, 1H, $J_{6,7}$=2.10 Hz, H-6), 2.68 (dd, 1H, $J_{3a,3e}$=12.64 Hz, $J_{3e,4}$=4.86 Hz, H-3e), 2.32–1.97 (7s, 21H, 6OAc, NAc), 2.17–1.96 (m, 2H, H-8, H-8'), 1.84 (t, 1H, H-3a)

Lac unit: 8.16–7.39 (m, 15H, 3Ph), 5.59 (t, 1H, $J_{2,3}$=9.44 Hz, H-3), 5.33'(dd, 1H, H-2), 5.26 (d, 1H, $J_{3',4'}$=3.29 Hz, H-4'), 5.17 (dd, 1H, $J_{2',3'}$=10.07 Hz, H-2'), 4.83 (d, 1H, $J_{1',2'}$=8.06 Hz, H-1'), 4.78 (d, 1H, $J_{1,2}$=7.88 Hz, H-1), 4.68 (dd, 1H, H-3'), 4.53 (dd, 1H, $J_{5,6}$=5.50 Hz, H-6), 3.66 (m, 1H, OCHCH₂Si), 0.98 (m, 2H, OCH₂CH₂Si), 0.00 (s, 9H, SiMe₃)

O-(Methyl 5-acetamido-4,7,9-tri-O-acetyl-3,5,8-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 3C)

Compound 3B (333 mg, 0.26 mmol) was dissolved in dichloromethane (4.5 ml), boron trifluoride diethyl ether (0.36 ml) was added dropwise under ice-cooling and the mixture was stirred at 0° C. for 8.5 hrs. After a completion of the reaction was confirmed by T.L.C. (dichloromethane:methanol=18:1), the reaction solution was extracted with dichloromethane. The organic layer was washed with successive sodium carbonate and water, dehydrated with anhydrous sodium sulfate, filtered and concentrated under reduced pressure. The resultant syrup was subjected to column chromatography with an eluting solvent (dichloromethane:methanol=60:1) to afford Compound 3C (294 mg, 95.8%).

$C_{57}H_{65}NO_{27}$ (1,196.13) $[\alpha]_D = +34.53°$ (c=0.944, $CHCl_3$)

IR $\nu^{film}_{max} cm^{-1}$: 3700-3150 (NH, OH), 3100-2950 (CH), 1750 (ester), 1670, 1540 (amide), 710 (phenyl)

O-(Methyl 5-acetamido-4,7,9-tri-O-acetyl-3,5,8-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 3D)

Compound 3C (294 mg, 0.25 mmol) was dissolved in dichloromethane (3.7 ml), trichloroacetonitrile (1.0 ml) and 1,8-diazabicyclo[5.4.0]-undec-7-ene (40 mg) were added under ice-cooling and the mixture was stirred at 0° C. for 2 hrs. After a completion of the reaction ws confirmed by T.L.C. (dichloromethane:methanol=18:1), the reaction solution was concentrated under reduced pressuer. The resultant syrup was subjected to column chromatography with an eluting solvent (dichloromethane:methanol=85:1) to afford Compound 3D (293 mg, 89.1%).

$C_{60}H_{65}N_2O_{27}Cl_3$ (1,340.52) $[\alpha]_D = +37.36°$ (c=1.686, $CHCl_3$)

IR $\nu^{film}_{max} cm^{-1}$: 3700-3200 (NH), 3100-3000 (CH), 1740 (ester), 1680 1540 (amide), 710 (phenyl)

$^1H$ NMR ($CDCl_3$) δ ppm

Neu5Ac unit: 5.08 (m, 1H, H-7), 4.04 (q, 1H, $J_{4,5}=J_{5,NH}=J_{5,6}=10.35$ Hz, H-5), 3.77 (s, 3H, COOMe), 3.35 (dd, 1H, $J_{6,7}=2.10$ Hz, H-6), 2.57 (dd, 1H, $J_{3a,3e}=12.64$ Hz, $J_{3e,4}=4.77$ Hz, H-3e), 2.22-1.85 (7s, 21H, 6OAc, NAc), 2.14-1.94 (m, 2H, H-8, H-8'), 1.72 (t, 1H, H-3a)

Lac unit: 8.58 (s, 1H, C=NH), 8.13-7.28 (m, 15H, 3Ph), 6.67 (d, 1H, $J_{1,2}=3.76$ Hz, H-1), 5.85 (t, 1H, $J_{2,3}=9.99$ Hz, H-3), 5.29 (dd, 1H, H-2), 5.17 (d, 1H, $J_{3',4'}=3.30$ Hz, H-4'), 5.09 (dd, 1H, $J_{2',3'}=9.89$Hz, H-2'), 4.78 (d, 1H, $J_{1',2'}=8.06$ Hz, H-1'), 4.59 (dd, 1H, H-3'), 4.49 (dd, 1H, $J_{5,6}=4.95$ Hz, H-6)

O-(Methyl 5-acetamido-4,7,9-tri-O-acetyl-3,5,8-trideoxy-D-glycero-α-D-galacto-2-nonulopyranosylonate)-(2→3)-O-2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-benzoyl-4-octadecene-1,3-diol (Compound 3E)

Compound 3D (183 g, 0.14 mmol) and Compound 17 (145 mg, 0.34 mmol) were dissolved in dichloromethane (5 ml), Molecular Sieves 4A type AW 300 (3.8 g) was added and the mixture was stirred at room temperature for 30 minutes. Then boron trifluoride diethyl ether (0.09 ml) was added dropwise under ice-cooling and the mixture was stirred at 0° C. for 2 hours. After a completion of the reaction was confirmed by T.L.C. (dichloromethane:methanol=18:1), the reaction solution was filtered through Celite and extracted with dichloromethane. The organic layer was washed with succesive sodium carbonate and water, dehydrated with anhydrous sodium sulfate, filtered and concentrated under reduced pressure. The resultant syrup was subjected to column chromatography with an eluting solvent (ethyl acetate:hexane=1:1) to afford Compound 3E (165 mg, 75.3%).

$C_{82}H_{102}N_4O_{29}$ (1,669.79) $[\alpha]_D = -9.53°$ (c=1.280, $CHCl_3$)

IR $\nu^{film}_{max} cm^{-1}$: 3700-3200 (NH), 3100-2850 (CH), 2100 ($N_3$), 1720 (ester), 1670, 1540 (amide), 710 (phenyl)

$^1H$ NMR ($CDCl_3$) δppm

Neu5Ac unit: 5.22 (d, 1H, NH), 4.94 (ddd, 1H, $J_{3e,4}=4.58$ Hz, H-4), 4.00 (q, 1H, $J_{4,5}=J_{5,NH}=J_{5,6}=10.44$ Hz, H-5), 3.77 (s, 3H, COOMe), 3.35 (dd, 1H, $J_{6,7}=2.02$ Hz, H-6), 2.56 (dd, 1H, $J_{3a,3e}=12.64$ Hz, H-3e), 2.19-1.85 (7s, 21H, 6OAc, NAc), 2.15-1.90 (m, 2H, H-8, H-8'), 1.72 (t, 1H, H-3a)

Lac unit: 8.09-7.27 (m, 15H, 3Ph), 5.48 (t, 1H, $J_{2,3}=9.16$ Hz, H-3), 5.26 (dd, 1H, H-2), 5.15 (d, 1H, $J_{3',4'}=3.30$ Hz, H-4'), 5.04 (dd, 1H, $J_{2',3'}=9.87$ Hz, H-2'), 4.72 (d, 1H, $J_{1',2'}=9.68$ Hz, H-1'), 4.69 (d, 1H, $J_{1,2}=7.69$ Hz, H-1), 4.58 (dd, 1H, H-3'), 4.41 (dd, 1H, $J_{5,6}=5.68$ Hz, H-6)

Sphingosine unit: 5.69 (m, 1H, $J_{5,6'}=J_{5,6'}=6.60$ Hz, H-5), 5.54 (dd, 1H, $J_{4,5}=8.25$ Hz, H-4), 1.25 (s, 22H, $11CH_2$), 0.88 (t, 3H, $CH_3$)

O-Methyl 5-acetamido-4,7,9-tri-O-acetyl-3,5,8-trideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-benzoyl-2-octadecanamide-4-octadecene-1,3-diol (Compound 3F)

Compound 3E (165 mg, 0.10 mmol) was dissolved in a mixed solvent of 5/1 pyridine/water (12 ml) and the solution was stirred at 0° C. for 4 days while blowing hydrogen sulfide gas. After a completion of the reaction was confirmed by T.L.C. (ethyl acetate), the reaction solution was evaporated under reduced pressure to dryness. The solid was dissolved in dichloromethane (9 ml), stearic acid (100 mg, 0.35 mmol) and WSC (110 mg) were added and the mixture was stirred at room temperature overnight. After a completion of the reaction was confirmed by T.L.C. (dichloromethane:methanol=18:1), the reaction solution was extracted with dichloromethane. The organic layer was washed with water, dehydrated with anhydrous sodium sulfate, filtered and concentrated under reduced pressure. The resultant syrup was subjected to column chromatography with an eluting solvent (dichloromethane:methanol=80:1) to afford Compound 3F (149 mg, 78.4%).

$C_{100}H_{138}N_2O_{30}$ (1,848.19) $[\alpha]_D = +5.33°$ (c=1.236, $CHCl_3$)

IR $\nu^{film}_{max} cm^{-1}$: 3700-3150 (NH), 3100-2850 (CH), 1740 (ester), 1660, 1530 (amide), 710 (phenyl)

$^1N$ NMR ($CDCl_3$) δ ppm

Neu5Ac unit: 5.64 (d, 1H, NH), 4.93 (ddd, 1H, $J_{3e,4}=4.67$ Hz, H-4), 4.07 (q, 1H, $J_{4,5}=J_{5,NH}=J_{5,6}=10.07$ Hz, H-5), 3.77 (s, 3H, COOMe), 3.36 (dd, 1H, $J_{6,7}=2.10$ Hz, H-6), 2.55 (dd, 1H, $J_{3a,3e}=12.91$ Hz, H-3-e), 2.16-1.85 (7s, 21H, 6OAc, NAc), 2.11-1.85 (m, 2H, H-8, H-8')

Lac unit: 8.03-7.25 (m, 20H, 4Ph), 5.47 (t, 1H, $J_{2,3}=9.71$ Hz, H-3), 5.19 (dd, 1H, H-2), 5.14 (d, 1H, $J_{3',4'}=3.48$ Hz, H-4'), 5.02 (dd, 1H, $J_{2',3'}=10.35$ Hz, H-2'), 4.68 (d, 1H, $J_{1',2'}=8.06$ Hz, H-1'), 4.60 (d, 1H, $J_{1,2}=8.55$ Hz, H-1), 4.55 (dd, 1H, H-3'), 4.37 (dd, 1H, $J_{gem}=10.85$ Hz, $J_{5,6}=6.69$ Hz, H-6), 4.34 (dd, 1H, H-6)

Cer unit: 5.78 (td, 1H, $J_{5,6}=J_{5,6'}=6.69$ Hz, H-5), 1.26 (s, 50H, 25CH$_2$), 0.88 (t, 6H, 2CH$_3$)

O-(5-Acetamido-3,5,8-trideoxy-D-glycero-α-D-galacto-2-nonulopyranosylonic acid)-2→3)-O-(β-D-galactopyranosyl)-1→4)-O-(β-D-glucopyranosyl)-(1→1)-(2S,3R,4E)-2-octadecanamide-4-octadecene-1,3-diol (Compound 3)

Compound 3F (149 mg, 0.08 mmol) was dissolved in methanol (3.5 ml), 28% sodium methylate solution (5 drops) was added and the mixture was stirred at room temperature for 10 hrs. Water (0.5 ml) was added and the mixture was stirred for further 13 hrs. After a completion of the reaction was confirmed by T.L.C. (butanol:ethanol:water=4:2:1), the reaction solution was neutralized with ion exchange resin Amberlite IR-120 (H$^+$), filtered and concentrated under reduced pressure. The resultant syrup was subjected to gel filtration with Sephadex LH-20 to afford Compound 3 (90 mg, quant.).

C$_{59}$H$_{108}$N$_2$O$_{20}$ (1,165.51) [α]$_D$= −1.22° (c=1.800, CHCl$_3$:MeOH=1:1)

$^1$H NMR (CDCl$_3$) δ ppm

Neu5Ac unit: 2.71 (broad, 1H, $J_{3a,3e}$=12.91 Hz, H-3e), 1.99 (s, 3H, NAc)

Lac unit: 4.42 (d, 1H, $J_{1',2'}$=7.33 Hz, H-1'), 4.30 (d, 1H, $J_{1,2}$=7.70 Hz, H-1)

Cer unit: 5.69 (td, 1H, $J_{5,6}=J_{5,6'}$=6.41 Hz, H-5), 5.45 (dd, 1H, H-4), 1.27 (s, 50H, 25CH$_2$), 0.89 (t, 6H, 2CH$_3$)

EXAMPLE 4

Methyl[2-(trimethylsilyl)ethyl 5-acetamido-9-O-t-butyldimethylsilyl-3,5-dideoxy-D-glycero-α-D-galacto-2-nonulopyranosid]onate (Compound 36)

Compound 9 (8.20 g, 19.36 mmol) was dissolved in pyridine (40 ml) and cooled to 0° C. Then t-butyldimethylsilylchloride (7.0 g) was added and the mixture was stirred at 0° C. for 2 hrs. After a completion of the reaction was confirmed by T.L.C. (dichloromethane:methanol=10:1), methanol was added, the mixture was stirred for 1 hr and concentrated under reduced pressure. The resultant syrup was subjected to column chromatography with an eluting solvent (ethyl acetate:hexane=4:1) to afford Compound 36 (9.42 g, 90.5%).

C$_{23}$H$_{47}$NO$_9$S$_1$ (537.80) [α]$_D$= −10.63° (c=1.448, CHCl$_3$)

IR ν$^{film}_{max}$cm$^{-1}$: 3700–3150 (NH, OH), 3150–2800 (CH), 1740 (ester), 1640, 1560 (amide), 860, 840 (TMS)

$^1$H NMR (CDCl$_3$) 3.82 (s, 3H, COOMe), 2.73 (dd, 1H, $J_{3a,3e}$=13.01 Hz, $J_{3e,4}$=4.30 Hz, H-3e), 2.01 (s, 3H, NAc), 0.90–0.85 (m, 11H, CH$_2$CH$_2$Si, t-BuSi), 0.00 (s, 9H, Me$_3$Si)

Methyl[2-(trimethylsilyl)ethyl 5-acetamido-4,8-di-O-benzoyl-9-O-t-butyldimethylsilyl-3,5-dideoxy-D-glycero-α-D-galacto-2-nonulopyranosid]onate (Compound 37)

Compound 36 (9.00 g, 16.73 mmol) was dissolved in a mixed solvent (dichloromethane:pyridine=4:1) (125 ml) and the solution was cooled to −5° C. Benzoyl chloride (10 ml) diluted with dichloromethane (20 ml) was added and the mixture was stirred at −5° C. for 1 hr. After a completion of the reaction was confirmed by T.L.C. (dichloromethane:methanol=30:1), methanol was added and the mixture was concentrated under reduced pressure. The resultant syrup was extracted with dichloromethane. The organic layer was washed with successive HCl and H$_2$O, dehydrated with anhydrous sodium sulfate, separated by filtration and concentrated under reduced pressure. The resultant syrup was subjected to column chromatography with an eluting solvent (ethyl acetate:hexane=2:3) to afford Compound 37 (9.97 g, 79.9%).

C$_{37}$H$_{55}$NO$_{11}$Si$_2$ (746.01) [α]$_D$= −33.00° (c=0.806, CHCl$_3$)

IR ν$^{film}_{max}$cm$^{-1}$: 3700–3150 (NH), 3150–2800 (CH), 1730 (ester), 1640, 1560 (amide), 860, 840 (TMS), 710 (phenyl)

$^1$H NMR (CDCl$_3$) 8.06–7.25 (m, 10H, 20Bz), 6.31 (d, 1H, $J_{5,NH}$=8.06 Hz, NH), 5.41 (m, 1H, H-8), 5.24 (ddd, 1H, $J_{3a,4}$=12.09 Hz, $J_{3e,4}$=4.76 Hz, $J_{4,5}$=10.63 Hz, H-4), 4.18 (q, 1H, $J_{5,6}$=10.63 Hz, H-5), 3.74 (dd, 1H, $J_{6,7}$=1.47 Hz, H-6), 3.39 (m, 1H, CHCH$_2$Si), 3.15 (s, 3H, COOMe), 2.67 (dd, 1H, $J_{3a,3e}=\overline{12.46}$ Hz, H-3e), 2.09 (t, 1H, H-3a), 1.92 (s, 3H, NAc), 0.84 (m, 11H, OCH$_2$CH$_2$Si, t-BuSi), 0.33 (s, 6H, Me$_2$Si), 0.00 (s, 9H, Me$_3$Si)

Methyl[2(trimethylsilyl)ethyl 5-acetamido-4,8-di-O-benzoyl-3,5-dideoxy-D-glycero-α-D-galacto-2-nonulopyranosid]onate (Compound 38)

Compound 37 (9.50 g, 12.73 mmol) was dissolved in 80% aqueous acetic acid solution (120 ml) and the solutoin was stirred at 40° C. for 4 hrs. After a completion of the reaction was confirmed by T.L.C. (dichloromethane:methanol=18:1), the reaction solution was concentrated under reduced pressure. The resultant syrup was subjected to column chromatography with an eluting solvent (ethyl acetate:hexane=3:2) to afford Compound 38 (7.98 g, 99.3%).

C$_{31}$H$_{41}$NO$_{11}$Si (631.75) [α]$_D$= −41.72° (c=0.604, CHCl$_3$)

IR ν$^{film}_{max}$cm$^{-1}$: 3700–3160(NH), 3160–2800(CH), 1730(ester), 1660, 1550(amide), 860, 840(TMS), 710(phenyl)

$^1$H NMR (CDCl$_3$, CD$_3$OC) 8.06–7.25(m, 10H, 20Bz), 5.38(m, 1H, H-8), 5.15(ddd, 1H, $J_{3a,4}$=12.64 Hz, $J_{3e,4}$=4.76 Hz, $J_{4,5}$=10.44 Hz, H-4), 4.15(t, 1H, $J_{5,6}$=10.44 Hz, H-5), 3.73(dd, 1H, $J_{6,7}$=1.56 Hz, H-6), 3.36(m, 1H, CHCH$_2$Si), 3.27(s, 3H, COOMe), 2.69(dd, 1H, $J_{3a,3e}=\overline{12.64}$ Hz, H-3e), 2.00(t, 1H, H-3a), 1.90(s, 3H, NAc), 0.85(m, 2H, OCH$_2$CH$_2$Si), 0.00(s, 9H, Me$_3$Si)

Methyl[2-(trimethylsilyl)ethyl 5-acetamido-4,8-di-O-benzoyl-9-chloro-3,5,9-trideoxy-D-glycero-α-D-galacto-2-nonulopyranosid]onate (Compound 39)

Compound 38 (5.05 g, 7.99 mmol) was dissolved in dimethylformamide (50 ml) and the mixture was cooled to 0° C. Triphenylphosphine (6.0 g) and carbon tetrachloride (50 ml) were added and the mixture was stirred at room temperature for 3 hrs. After a completoin of the reaction was confirmed by T.L.C. (dichloromethane:methanol=30:1), methanol was added and the reaction solution was concentrated under reduced pressure. The resultant syrup was subjected to column chromatography with an eluting solvent (ethyl acetate:hexane=1:4) to afford Compound 39 (4.12 g, 81.0%).

C$_{30}$H$_{38}$NO$_{10}$ClSi (636.17) [α]$_D$= −68.11° (c=0.784, CHCl$_3$)

IR ν$^{film}_{max}$cm$^{-1}$: 3700–3160 (NH), 3160–2800 (CH), 1730 (ester), 1660, 1550 (amide), 860, 840 (TMS)

$^1$H NMR (CDCl$_3$) 8.04–7.22 (m, 10H, 20Bz), 6.18 (d, 1H, $J_{5,NH}$=7.87 Hz, NH), 5.58 (m, 1H, H-8), 5.17 (ddd, 1H, J$_{3e,4}$=4.76 Hz, J$_{4,5}$=10.44 Hz, H-4), 3.70 (dd, 1H, J$_{5,6}$=10.44 Hz, J$_{6,7}$=1.65 Hz, H-6), 3.38 (m, 1H, CHCH$_2$Si), 3.25 (s, 3H, COOMe), 2.67 (dd, 1H, J$_{3a,3e}$=12.64 Hz, H-3e), 2.05 (t, 1H, H-3a), 1.91 (s, 3H, NAc), 0.84 (m, 2H, OCH$_2$CH$_2$Si), 0.00 (s, 9H, Me$_3$Si)

Methyl[2-(trimethylsilyl)ethyl 5-acetamido-4,8-di-O-benzoyl-3,5,9-trideoxy-D-glycero-α-D-galacto-2-nonulopyranosid]onate (Compound 40)

Compound 39 (0.76 g, 1.19 mmol) was dissolved in toluene (20 ml), tributyltin hydride (1.0 ml) and 2,2'-azobisisobutyronitrile (10 mg) were added and the mixture was stirred at 100° C. for one hour. After a completion of the reaction was confirmed by T.L.C. (dichloromethane:methanol=30:1), the reaction solution was concentrated under reduced pressure. The resultant syrup was subjected to column chromatography with an eluting solvent (ethyl acetate:hexane=1:4) to afford Compound 40 (0.48 g, 65.3%).

C$_{31}$H$_{41}$NO$_{10}$Si (615.75) [α]$_D$= +7.64° (c=0.602, CHCl$_3$)

IR ν$^{film}_{max}$cm$^{-1}$: 3700–3150 (NH), 3150–2800 (CH), 1730 (ester), 1670, 1550 (amide), 860, 840 (TMS)

$^1$H NMR (CDCl$_3$, CD$_3$OD) 8.02–7.28 (m, 10H, 20Bz), 5.38 (m, 1H, J$_{7,8}$=8.06 Hz, J$_{8,9}$=6.23 Hz, H-8), 5.15 (ddd, 1H, J$_{3e,4}$=4.77 Hz, J$_{4,5}$=10.44 Hz, H-4), 4.17 (t, 1H, J$_{5,6}$=10.44 Hz, H-5), 3.95 (m, 1H, CHCH$_2$Si), 3.75 (dd, 1H, J$_{6,7}$=1.65 Hz, H-6), 3.65 (dd, 1H, H-7), 3.39 (m, 1H, CH' CH$_2$Si), 3.30 (s, 3H, COOMe), 2.70 (dd, 1H, J$_{3a,3e}$=12.64 Hz, H-3e), 1.98 (t, 1H, H-3a), 1.91 (s, 3H, NAc), 1.47 (d, 3H, CH$_3$), 0.88–0.81 (m, 2H, OCH$_2$CH$_2$Si), 0.00 (s, 9H, Me$_3$Si)

Methyl[2-(trimethylsilyl)ethyl 5-acetamido-4,7,8-tri-O-acetyl-3,5,9-trideoxy-D-glycero-α-D-galacto-2-nonulopyranosid]onate (Compound 41)

Compound 40 (2.10 g, 3.41 mmol) was dissolved in methanol (20 ml), 28% sodium methylate solution (3 ml) was added and the mixture was stirred at room temperature for 30 hrs. After a completion of the reaction was confirmed by T.L.C., the reaction solution was neutralized with an ion exchange resin IR-120 (H$^+$) and concentrated under reduced pressure to dryness. The solid was dissolved in pyridine (20 ml), acetic anhydride (16 ml) was added and the mixture was stirred overnight. After a completion of the reaction was confirmed by T.L.C. (dichloromethane:methanol=18:1), methanol was added and the reaction solution was concentrated under reduced pressure. The resultant syrup was extracted with dichloromethane. The dichloromethane layer was washed with HCl and H$_2$O, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=2:2) to afford Compound 41 (1.55 g, 85.2%).

C$_{23}$H$_{39}$NO$_{11}$Si(533.65) [α]$_D$=1−13.54° (c=0.812, CHCl$_3$)

IR ν$^{film}_{max}$cm$^{-1}$: 3700–3170(NH), 3170–2800(CH), 1740(ester), 1670, 1550(amide), 860, 840(TMS)

$^1$H NMR (CDCl$_3$) 5.31(d, 1H, J$_{5,NH}$=9.52 Hz, NH), 5.19(m, 1H, J$_{7,8}$=7.87 Hz, J$_{8,Me}$=6.05 Hz, H-8), 5.13(dd, 1H, J$_{6,7}$=1.83 Hz, H-7), 4.80(ddd, 1H, J$_{3e,4}$=4.58 Hz, J$_{4,5}$=9.71 Hz, H-4), 4.08(q, 1H, J$_{5,6}$=10.63 Hz, H-5), 4.02(dd, 1H, H-6), 3.86(m, 1H, CHCH$_2$Si), 3.76(s, 3H, COOMe), 3.32(m, 1H, CH' CH$_2$Si), 2.56(dd, 1H, J$_{3a,3e}$=12.64 Hz, H-3e), 2.12–1.86(4s, 12H, 3OAc, NAc), 1.18 (d, 3H, CH$_3$), 0.92–0.79(m, 2H, OCH$_2$CH$_2$Si), 0.00(s, 9H, Me$_3$Si)

Methyl(5-acetamido-2,4,7,8-tetra-O-acetyl-3,5,9-trideoxy-D-glycero-D-galacto-2-nonulopyranosid)onate (Compound 42)

Compound 41 (1.51 g, 2.83 mmol) was dissolved in dichloromethane (30 ml), the solution was cooled to 0° C., boron trifluoride diethyl ether (0.62 ml) was added and the mixture was stirred at 0° C. for 3 hrs. After a completion of the reaction was confirmed by T.L.C. (dichloromethane:methanol=18:1), the reaction solution was extracted with dichloromethane. The dichloromethane layer was washed with sodium carbonate and water, dehydrated with anhydrous sodium sulfate, separated by filtration and washed with dichloromethane. The combined filtrate and washings were concentrated under reduced pressure to dryness. The solid was dissolved in pyridine (10 ml), acetic anhydride (7 ml) was added and the mixture was stirred at room temperature overnight. After a completion of the reaction was confirmed by T.L.C. (dichloromethane:methanol=18:1), methanol was added and the reaction solution was concentrated under reduced pressure. The resultant syrup was extracted with dichloromethane. The dichloromethane layer was washed with HCl and H$_2$O, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=2:3) to afford Compound 42 (1.22 g, 90.7%).

C$_{20}$H$_{29}$NO$_{12}$ (475.45) [α]$_D$=−41.49° (c=1.094, CHCl$_3$)

IR ν$^{film}_{max}$cm$^{-1}$: 3700–3160 (NH), 3160–2800 (CH), 1740 (ester), 1660, 1550 (amide)

$^1$H NMR(CDCl$_3$): α 5.57 (d, 1H, J$_{5,NH}$=10.26 Hz, NH), 5.20 (m, 1H, J$_{6,7}$=2.38 Hz, J$_{7,8}$=6.78 Hz, H-7), 5.05 (m, 2H, H-4,8), 4.57 (dd, 1H, J$_{5,6}$-10.63 Hz, H-6), 4.18 (q, 1H, H-5), 3.75 (s, 3H, COOMe), 2.61 (dd, 1H, J$_{3a,3e}$=13.00 Hz, J$_{3e,4}$=4.95 Hz, H-3e), 2.15–1.89 (5s, 15H, 4OAc, NAc), 1.20 (d, 3H, J$_{8,Me}$=6.23 Hz, CH$_3$)

$^1$H NMR(CDCl$_3$): β 5.56 (d, 1H, NH), 5.23 (m, 1H, H-8), 5.21 (m, 1H, J$_{6,7}$=2.20 Hz, J$_{7,8}$=4.95 Hz, H-7), 4.94 (dd, 1H, J$_{3e,4}$=4.94 Hz, H-4), 4.17 (q, 1H, J$_{4,5}$=J$_{5,6}$=J$_{5,NH}$=10.44 Hz, H-5), 4.18 (dd, 1H, H-6), 3.79 (s, 3H, COOMe), 2.53 (dd, 1H, J$_{3a,3e}$=13.38 Hz, H-3e), 2.16–1.89 (5s, 15H, 4OAc NAc), 1.25 (d, 3H, J$_{8,Me}$=6.41 Hz, CH$_3$)

Methyl(5-acetamido-4,7,8-tri-O-acetyl-2-S-acetyl-3,5,9-trideoxy-2-thio-D-glycero-α-D-galacto-2-nonulopyranosid)onate (Compound 44)

Compound 42 (1.51 g, 3.18 mmol) was dissolved in dichloromethane (30 ml) and cooled to −20° C. Hydrogen chloride gas was bubbled into the solution for 10 minutes, a flask was sealed and allowed to stand in the dark one day. After a completion of the reaction was confirmed by T.L.C. (dichloromethane:methanol=18:1), the reaction solution was concentrated under reduced pressure below 30° C. The resultant syrup was lyophilized to obtain an atypical intermediate of Compound 43. Compound 30 was dissolved in dichloromethane (15 ml) and acetone (10 ml), Drierite ® (2 g) was added and the mixture was stirred at room temperature for one hour. Potassium thioacetate (1.36 g, 11.92 mmol) was added and the mixture was stirred at room temperature for 3 hrs. After a completion of the reaction was confirmed by T.L.C. (dichloromethane:methanol=18:1), the reaction product was filtered through Celite and washed with dichloromethane. The combined filtrate and washings were concentrated under reduced pressure. The resultant syrup was subjected to column chromatography with an eluting solvent (ethyl acetate:hexane=1:1) to afford Compound 44 (1.22 g, 78.2%).

$C_{20}H_{29}NO_{11}S$ (491.51) $[\alpha]_D = +34.88°$ (c=0.986, $CHCl_3$) IR $\nu^{film}{}_{max}cm^{-1}$: 3700–3150 (NH), 3150–2800 (CH, 1750 (ester), 1650. 1540 (amide) 1540 (amide)

$^1H$ NMR ($CDCl_3$): 5.54 (d, 1H, $J_{5,NH}$=10.25 Hz, NH), 5.19 (dd, 1H, $J_{6,7}$=2.20 Hz, $J_{7,8}$=6.96 Hz, H-7), 5.07 (m, 1H, H-8), 4.93 (ddd, 1H, $J_{3e,4}$=4.76 Hz, $J_{4,5}$=10.26 Hz, H-4), 4.53 (dd, 1H, $J_{5,6}$=10.63 Hz, H-6), 4.12 (q, 1H, H-5 ), 3.79 (s, 3H, COOMe), 2.68 (dd, 1H, $J_{3a,3e}$=12.82 Hz, H-3e), 2.28–1.88 (5s, 15H, 3OAc NAc SAc), 1.20 (d, 3H, $J_{8,Me}$=6.23 Hz, $CH_3$)

Methyl(methyl 5-acetamido-4,7,8-tri-O-acetyl-3,5,9-trideoxy-2-thio-D-glycero-α-D-galacto-2-nonulopyranosid)onate (Compound 45)

Compound 44 (0.98 g, 1.99 mmol) was dissolved in methanol (20 ml), metallic sodium (47 mg) dissolved in methanol (4 ml) at −40° C. was added dropwise and the mixture was stirred for 5 minutes. Then the stirred mixture was concentrated under reduced pressure at a water temperature and well dried. The solid was dissolved in dimethylformamide (12 ml), methyl iodide (0.2 ml) was added and the mixture was stirred at room temperature for 3 hrs. After a completion of the reaction was confirmed by T.L.C. (dichloromethane:methanol=5:1), pyridine (15 ml) and acetic anhydride (10 ml) were added and the mixture was stirred at room temperature overnight. After a completion of the reaction was confirmed by T.L.C. (dichloromethane:methanol=18:1), the reaction solution was concentrated under reduced pressure. The resultant syrup was extracted with dichloromethane and the dichloromethane layer was washed with HCl and $H_2O$, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=1:1) to afford Compound 45 (0.82 g, 88.7%).

$CH_{19}H_{29}NO_{10}S$ (463.50) $[\alpha]_D = -23.48°$ (c=1.056, $CHCl_3$)

IR $\nu^{film}{}_{max}cm^{-1}$: 3700–3160 (NH), 3160–2800 (CH), 1740 (ester), 1670, 1550 (amide) $^1H$ NMR($CDCl_3$) 5.38 (d, 1H, NH), 5.23 (m, 1H, H-8), 5.15 (dd, 1H, $J_{6,7}$=2.20 Hz, $J_{7,8}$=8.43 Hz, H-7), 4.86 (ddd, 1H, $J_{3e,4}$=4.76 Hz, H-4), 4.12 (q, 1H, $J_{4,5}$=$J_{5,6}$=$J_{5,NH}$=10.44 Hz, H-5), 3.80 (s, 3H, COOMe), 3.79 (dd, 1H, H-6), 2.72 (dd, 1H, $J_{3a,3e}$=12.64 Hz, H-3e), 2.15–1.88 (5s, 15H, 3OAc NAc SMe), 1.20 (d, 3H, $J_{8,Me}$=6.05 Hz, $CH_3$)

2-(Trimethylsilyl)ethyl O-(methyl 5-acetamido-4,7,8-tri-O-acetyl-3,5,9-trideoxy-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 4A)

Compound 45 (1.10 g, 2.37 mmol) and Compound 16 (0.90 g, 1.20 mmol) were dissolved in acetonitrile (10 ml), Molecular Sieves 3A (3.0 g) was added and the mixture was stirred overnight. After cooling to −15° C., dimethyl(methylthio)sulfonium triflate (50%, 3.0 g) was added and the mixture was stirred at −15° C. for 2 days. After a completion of the reaction was confirmed by T.L.C. (dichloromethane:methanol=18:1), the reaction solution was filtered through Celite and the combined filtrate and washings were extracted with dichloromethane. The dichloromethane layer was washed with sodium carbonate and water, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate:hexane=3:2) to afford Compound 4A (0.60 g, 43.0%).

$C_{56}H_{71}NO_{24}Si$ (1170.26)
$[\alpha]_D = +8.28°$ (c=0.700, $CHCl_3$)

IR $\nu^{film}{}_{max}cm^{-1}$: 3700–3130 (NH), 3130–2800 (CH), 1730 (ester), 1680, 1530 (amide), 850, 830 ($Me_3Si$), 700(phenyl) 270 MHz $^1H$-NMR ($CDCl_3$)

Lac unit: δ 8.20–7.40 (m, 15H, 3BzO), 5.36 (dd, 1H, $J_{1,2}$=8.06 Hz, $J_{2,3}$=9.53 Hz, H-2), 4.87 (dd, 1H, $J_{gem}$=11.91 Hz, $J_{5,6}$=2.93 Hz, H-6), 4.76 (d, 1H, H-1), 4.68 (d, 1H, $J_{1',2'}$=8.06 Hz, H-1), 4.62 (dd, 1H, H-6), 3.68 (ddd, 1H, $CHCH_2Si$), 0.97 (m, 2H, $CH_2CH_2Si$), 0.00 (s, 9H, $Me_3Si$)

Neu5Ac unit: 5.22 (dd, 1H, $J_{6,7}$=1.74 Hz, $J_{7,8}$=9.25 Hz, H-7), 3.90 (s, 3H, COOMe), 2.80 (dd, 1H, $J_{3a,3e}$=13.01 Hz, $J_{3e,4}$=4.58 Hz, H-3e), 2.26–2.01 (4s, 12H, 3AcO, AcN), 1.14 (d, $J_{8,Me}$=6.22 Hz, $CH_3$)

2-(Trimethylsilyl)ethyl O-(methyl 5-acetamido-4,7,8-tri-O-acetyl-3,5,9-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 4B)

Compound 4A (0.45 g, 0.38 mmol) was dissolved in pyridine (10 ml), acetic anhydride (7 ml) was added and the mixture was stirred at room temperature overnight. After a completion of the reaction was confirmed by T.L.C. (dichloromethane:methanol=18:1), methanol was added to decompose excessive reagent and concentrated under reduced pressure. The resultant syrup was subjected to column chromatography with an eluting solvent (dichloromethane:methanol=100:1) to afford Compound 4B (0.42 g, 84.3%).

$C_{62}H_{77}NO_{27}Si$ (1296.37)
$[\alpha]_D = +1.62°$ (c=0.614, $CHCl_3$)

IR $\nu^{film}{}_{max}cm^{-1}$: 3700–3160 (NH), 3160–2800 (CH), 1730 (ester), 1670, 1550 (amide), 860, 840 ($Me_3Si$), 710 (phenyl) 270 MHz $^1H$-NMR ($CDCl_3$)

Lac unit: δ 8.20–7.39 (m, 15H, 3BzO), 5.58 (t, 1H, $J_{2,3}$=$J_{3,4}$=9.53 Hz, H-3), 5.34 (dd, 1H, $J_{1,2}$=8.06 Hz, H-2), 5.11 (d, 1H, H-4'), 4.97 (d, 1H, H-1), 4.78 (d, 1H, $J_{1',2'}$=8.06 Hz, H-1), 4.67 (dd, 1H, $J_{2',3'}$=10.26 Hz, $J_{3',4'}$=3.29 Hz, H-3'), 3.68 (ddd, 1H, $CHCH_2Si$), 0.98 (m, 2H, $CH_2CH_2Si$), 0.00 (s, 9H, $Me_3Si$)

Neu5Ac unit: 5.47 (m, 1H, H-8), 5.32 (dd, 1H, $J_{6,7}$=1.83 Hz, $J_{7,8}$=9.89 Hz, H-7), 3.95(s, 3H, COOMe), 2.68(dd, 1H, $J_{3a,3e}$=12.64 Hz, $J_{3e,4}$=4.40 Hz, H-3e), 2.32–1.74(7s, 21H, 6AcO, AcN), 1.23(d, 3H, $J_{8,Me}$=6.59 Hz, $CH_3$)

O-(Methyl 5-acetamido-4,7,8-tri-O-acetyl-3,5,9-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 4C)

Compound 4B (0.39 g, 0.30 mmol) was dissolved in dichloromethane (8 ml), boron trifluoride diethyl ether (0.3 ml) was added dropwise under ice-cooling and the mixture was stirred at 0° C. for 6 hrs. After a completion of the reaction was confirmed by T.L.C. (dichloromethane:methanol=18:1), the reaction solution was extracted with dichloromethane. The dichloromethane layer was washed with successive sodium carbonate and water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=60:1) to afford Compound 4C (0.30 g, 83.6%).

$C_{57}H_{65}NO)_{27}(1196.13)$ $[\alpha]_D = +30.32°$ (c=0.930, CDCl$_3$)

IR $\nu^{KBr}_{max}$cm$^{-}$: 3720–3160(OH, NH), 3160–2800(CH), 1750(ester), 1680, 1560(amide), 720(phenyl)

O-(Methyl 5-acetamido-4,7,8-tri-O-acetyl-3,5,9-trideoxy-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 4D)

Compound 4C (0.24 g, 0.20 mmol) was dissolved in dichloromethane (3 ml), trichloroacetonitrile (0.6 ml) and 1,8-diazabicyclo[5.4.0]-undec-ene (30 mg) were added and the mixture was stirred at 0° C. for 2 hrs. After a completion of the reaction was confirmed by T.L.C. (dichloromethane:methanol=18:1), the reaction solution was concentrated under reduced pressure. The resultant syrup was subjected to column chromatography with an eluting solvent (dichloromethane:methanol=80:1) to afford Compound 4D (0.22 g, 81.8%).

$C_{59}H_{65}N_2O_{27}Cl_3$ (1340.52)

$[\alpha]_D = +31.61°$ (c=1.060, CHCl$_3$)

IR $\nu^{film}_{max}$cm$^{-1}$: 3700–3150 (OH, NH), 3150–2800 (CH), 1740 (ester), 1680, 1540 (amide), 710 (phenyl)

270 MHz, 1H-NMR (CDCl$_3$)

Lac unit: δ 8.54–7.27 (m, 15H, 3BzO), 6.66 (d, 1H, $J_{1,2}$=3.67 Hz, H-1), 5.83 (t, 1H, $J_{2,3}=J_{3,4}$=9.71 Hz, H-3), 5.27 (dd, 1H, H-2), 5.05 (dd, 1H, $J_{1',2'}$=8.06 Hz, $J_{2',3'}$=10.26 Hz, H-2'), 4.90 (d, 1H, H-1'), 4.88 (dd, 1H, H-4'), 4.56 (dd, 1H, H-3')

Neu5Ac unit: 5.38 (m, 1H, H-8), 5.13 (m, 1H, $J_{6,7}$=2.93 Hz, $J_{7,8}$=9.89 Hz, H-7), 3.72 (s, 3H, COOMe), 3.58 (dd, 1H, H-6), 2.56 (dd, 1H, $J_{3a,3e}$=12.46 Hz, $J_{3e,4}$=4.40 Hz, H-3e), 2.20–1.83 (7s, 21H, 6AcO, AcN), 1.66 (t, 1H, H-3a), 1.08 (d, 3H, $J_{8,Me}$=6.23 Hz, CH$_3$)

O-(Methyl 5-acetamido-4,7,8-tri-O-acetyl-3,5,9-trideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-benzoyl-4-octadecene-1,3-diol (Compound 4E)

Compound 4D (0.10 g, 0.07 mmol) and Compound 17 (0.07 g, 0.16 mmol) were dissolved in dichloromethane (3 ml), Molecular Sieves 4A type AW 300 (2 g) was added and the mixture was stirred at room temperature for 30 minutes. Then boron trifluoride diethyl ether (0.04 ml) was added dropwise under ice-cooling and the mixture was stirred at 0° C. for 4 hrs. After a completion of the reaction was confirmed by T.L.C. (dichloromethane:methanol=18:1), the reaction was filtered through Celite and the combined filtrate and washings were extracted with dichloromethane. The dichloromethane layer was washed with successive sodium carbonate and water, dehydrated with anhydrous sodium sulfate, separated by filtration and washed with dichloromethane. The filtrate and washings were combined. The resultant syrup was subjected to column chromatography with an eluting solvent (dichloromethane:methanol=80:1) to afford Compound 4E (0.11 g, 92.4%).

$C_{82}H_{102}N_4O_{29}$ (1607.72)

$[\alpha]_D = -8.59°$ (c=1.094, CHCl$_3$)

IR $\nu^{film}_{max}$cm$^{-1}$: 3700–3140 (NH), 3140–2800 (CH), 2100 (N$_3$), 1730 (ester), 1650, 1530 (amide), 700 (phenyl)

270 MHz $^1$H NMR (CDCl$_3$)

Lac unit: δ 8.07–7.26 (m, 20H, 4BzO), 5.47 (t, 1H, $J_{2,3}$=9.53 Hz, H-3), 5.25 (dd, 1H, $J_{1,2}$=7.87 Hz, H-2), 5.00 (dd, 1H, $J_{1',2'}$=7.88 Hz, $J_{2',3'}$=10.08 Hz, H-2'), 4.99 (d, 1H, H-4'), 4.86 (d, 1H, H-1'), 4.68 (d, 1H, H-1)

Neu5Ac unit: 5.15 (dd, 1H, $J_{6,7}$=2.93 Hz, H-7), 3,71 (s, 3H, COOMe), 3.58 (dd, 1H, $J_{5,6}$=10.62 Hz, H-6), 2.55 (dd, 1H, $J_{3a,3e}$=12.27 Hz, $J_{3e,4}$=4.40 Hz, H-3e), 2.19–1.87 (7s, 21H, 6AcO, AcN), 1.10 (d, 3H, $J_{8,Me}$=6.23 Hz, CH$_3$)

Sphingosine unit: 5.65 (m, 1H, H-5), 1.24 (s, 22H, 11CH$_2$), 0.87 (t, 3H, CH$_3$)

O-Methyl 5-acetamido-4,7,8-tri-O-acetyl-3,5,9-trideoxy-D-glycero-α-D-galacto-2-nonulopyranosylonate)-)2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-benzoyl-2-octadecanamide-4-octadecene-1,3-diol (Compound 4F)

Compound 4E (110 mg, 0.06 mmol) was dissolved in a mixed solvent of 5/1 pyridine/water (12 ml) and the solution was stirred at room temperature for 36 hrs. while blowing hydrogen sulfide gas. After a completion of the reaction was confirmed by T.L.C. (ethyl acetate), the reaction solution was evaporated under reduced pressure to dryness. The solid was dissolved in dichloromethane (6 ml), stearic acid (58 mg, 0.20 mmol) and WSC (58 mg) were added and the mixture was stirred at room temperature overnight. After a completion of the reaction was confirmed by T.L.C. (dichloromethane:methanol=18:1), the reaction solution was extracted with dichloromethane. The dichloromethane layer was washed with water, dehydrated with anhydrous sodium sulfate, separated by filtration, and washed with dichlroomethane. The combined filtrate and washings were concentrated under reduced pressure. The resultant syrup was subjected to column chromatography with an eluting solvent (dichloromethane:methanol=80:1) to afford Compound 4F (97 mg, 76.9%).

$C_{100}H_{138}N_2O_{30}$ (1848.19)

$[\alpha]_D = +4.98°$ (c=1.084, CHCl$_3$)

IR $\nu^{film}_{max}$CM$^{-1}$: 3700-3140 (NH), 3140-2800 (CH), 1750 (ester), 166 0, 1530 (amide), 710 (phenyl) 270 MHz$^1$ H-NMR (CDCl$_3$)

Lac unit: δ8.07-7.26 (m, 20H, 4BzO), 5.43 (t, 1H, $J_{2,3}$=9.89 Hz, H-3), 5.19 (dd, 1H, $J_{1,2}$=7.69 Hz, H-2), 5.06 (dd, 1H, $J_{1',2'}$=7.70 Hz, H-2'), 4.82 (d, 1H, H-1'), 4.60 (d, 1H, H-1), 4.55 (dd, 1H, $J_{2',3'}$=9.89 Hz, $J_{3',4'}$=3.30 Hz, H-3')

Neu5Ac unit: 5.63 (d, 1H, NH), 5.14 (dd, 1H, $J_{6,7}$=2.93 Hz, H-7), 3.7 1 (s, 3H, COOMe), 3.58 (dd, 1H, $J_{5,6}$=10.62 Hz, H-6), 2.58 (dd, 1H, $J_{3a,3e}$=12.46 Hz, $J_{3e,4}$=4.40 Hz, H-3e), 2.18-1.83 (7s, 21H, 6AcO, AcN), 1.65 (t, 1H, H-3a), 1.11 (d, 3H, $J_{8,Me}$=6.23 Hz, CH$_3$)

Cer unit: 5.76 (td, 1H, $J_{5,6}$=$J_{5,6'}$=6.60 Hz, H-5), 1.26 (s, 50H, 25C H$_2$), 0.87 (t, 6H, 2CH$_3$)

O-(5-Acetamido-3,5,9-trideoxy-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-2-octadecanamide-4-octadecene-1,3-diol (Compound 4)

Compound 4F (91 mg, 0.049 mmol) was dissolved in methanol (3 ml), 28% sodium methylate solution (5 drops) was added and the mixture was stirred at room temperature for 6 hrs. Water (0.5 ml) was added and the mixture was stirred for further 24 hrs. After a completion of the reaction was confirmed by T.L.C. (butanol:ethanol:water=4:2:1), the reaction solution was neutralized with ion exchange resin IR-120 (H+), filtered and concentrated under reduced pressure. The resultant syrup was subjected to gel filtration with Sephadex LH-20 to afford Compound 4 (52 mg, 91.1%).

$C_{59}H_{108}N_2O_{20}$ (1165.51) [α]$_D$= -0.49° (C=1.212, MeOH:CH$_2$Cl$_2$=1:1)

IR $\nu^{KBr}_{max}$cm$^{-1}$: 3800-2800 (OH, NH), 2950, 2870 (Me, methylene), 1720 (C=O), 1660, 1540 (amide) 270 MHz $^1$H-NMR (CDCl$_3$)

Lac unit: δ4.42 (d, 1H, $J_{1',2'}$=7.69 Hz, H-1'), 4.31 (d, 1H, $J_{1,2}$=7.70 Hz, H-1)

Neu5Ac unit: 2.85 (broad, 1H, H-3e) Cer unit: 5.68 (td, 1H, $J_{5,6}$=$J_{5,6'}$=6.78 Hz, H-5), 4.43 (dd, 1H, H-4), 1.27 (s, 50H, 25CH$_2$), 0.89 (t, 6H, 2CH$_3$)

EXAMPLE 5

Methyl(methyl 5-acetamido-3,5-dideoxy-8,9-O-isopropylidene-2-thio-D-glycero-α-D-galacto-2-nonulopyranosid)onate (Compound 47)

Compound 46 (3.0 g, 7.1 mmol) was dissolved in dimethylformamide (25 ml), 2,2-dimethoxypropane (5.2 ml) and Drierite ® (3.0 g) were added, and the mixture was stirred at room temperature for 3 hrs. The p-toluenesulfonic acid was added for adjustment to pH 3 and the mixture was stirred as such for 20 minutes. After a completion of the reaction was confirmed by T.L.C. (dichloromethane:methanol=10:1), the reaction solution was neutralized with sodium bicarbonate, filtered through Celite and the filtrate was concentrated under reduced pressure. The resultant syrup was subjected to column chromatography with an eluting solvent (ethyl acetate:hexane=2:1) to afford Compound 47 (2.69 g, 63.4%).

$C_{16}H_{27}NO_8S$ (393.5) $[\alpha]_D$= +12.44° (c 0.948, CHCl$_3$)

IR $\nu^{film}_{max}$cm$^{-1}$:3700-3150 (OH, NH), 3150-2800 (CH), 1740 (ester), 1650, 1550 (amide), 820 (isopropylidene) 270 MHz $^1$H-NMR(CDCl$_3$) δ4.29 (q, 1H, $J_{7,8}$=$J_{8,9}$=$J_{8,9'}$=6.23 Hz, H-8), 4.07 (m, 2H, $J_{9,9'}$=6.60 Hz, H-9,9'), 3.49(s, 3H, COOMe), 3.27(dd, 1H, $J_{5,6}$=10.44 Hz, $J_{6,7}$=1.38 Hz, H-6), 2.79(dd, 1H, $J_{3a,3e}$=12.82 Hz, $J_{3e,4}$=4.67 Hz, H-3 e), 2.18, 2.02(2s, 6H, NAc and SMe), 1.80(t, 1H, H-3a), 1.40, 1.37(2s, 6H, C-Me$_2$)

Methyl(methyl 5-acetamido-3,5-dideoxy-8,9-O-isopropylidene-4-O-methyl-2-thio-D-glycero-α-D-galacto-2-nonulopyranosid)onate (Compound 48)

Compound 47 (0.10 g, 0.24 mmol) was dissolved in methanol (5 ml) and the solution was cooled at 0° C. Methyl iodide (0.36 g, 2.53 mmol) and silver oxide (0.30 g, 1.29 mmol) were added and the mixture was stirred at room temperature for 6 hrs. After a completion of the reaction was confirmed by T.L.C. (dichloromethane:methanol=10:1), the reaction solution was filtered through Celite and concentrated under reduced pressure. The resultant syrup was subjected to column chromatography with an eluting solvent (dichloromethane:methanol=70:1) to afford Compound 48 (0.80 g, 77.2%).

$C_{17}H_{29}NO_8S$ (407.48) $[\alpha]_D$=+19.04° (c 1.250, CHCl$_3$)

IR $\nu^{film}_{max}$cm$^{-1}$: 3700-3180 (NH), 3180-2800 (CH), 1740 (ester), 1650, 1550 (amide), 850 (isopropylidene)

$^1$H-NMR(CDCl$_3$)4.30(dd, 1H, $J_{gem}$=6.60 Hz, H-9), 4.09(dd, 1H, H-9'), 4.08 (q, 1H, H-5), 3.86(dd, 1H, $J_{6,7}$=2.57 Hz, H-7), 3.81(s, 3H, COOMe), 3.40(m, 1H, $J_{3e,4}$=4.39 Hz, $J_{4,5}$=10.62 Hz, H-4), 3.35(s, 3H, OMe), 3.26(dd, 1H, H-6), 2.73(dd, 1H, $J_{3a,3e}$=12.64 Hz, H-3e), 2.19, 2.01(2s, 6H, NAc, SMe), 1.72(t, 1H, H-3a), 1.37(2s, 6H, 2CH$_3$)

Methyl(methyl 5-acetamido-7,8,9-tri-O-acetyl-3,5-dideoxy-4-O-methyl-2-thio-D-glycero-α-D-galacto-2-nonulopyranosid]onate (Compound 49)

Compound 48 (2.0 g, 4.9 mmol) was dissolved in 80% acetic acid (80 ml) and the solution was allowed to stand at room temperature for 20 hrs. After a completion of the reaction was confirmed by T.L.C. (dichloromethane:methanol=10:1), the reaction solution was evaporated under reduced pressure to dryness. The resultant syrup was dissolved in pyridine (50 ml), acetic anhydride (40 ml) was added and the mixture was stirred at room temperature for 12 hrs. After a completion of the reaction was confirmed by T.L.C. (dichloromethane:methanol=30:1), methanol was added and the mixture was concentrated under reduced pressure. The resultant syrup was subjected to column chromatogrpahy with an eluting solvent (ethyl acetate:hexane=2:3) to afford Compound 49 (2.2 g, 90.9%).

$C_{20}H_{31}NO_{11}S$ (493.53) $[\alpha]_D$= +55.90° (c 1.474, CHCl$_3$)

IR $\nu^{film}_{max}$cm$^{-1}$:3700-3170 (NH), 3170-2800 (CH), 1750 (ester), 1660, 1550 (amide)

$^1$H-NMR(CDCl$_3$)5.60(d, 1H, $J_{5,NH}$=8.61 Hz, NH), 5.39(m, 1H, $J_{8,9}$=2.38 Hz, $J_{8,9'}$=4.95 Hz, H-8), 5.31(dd, 1H, $J_{6,7}$=1.65 Hz, $J_{7,8}$=8.51 Hz, H-4), 4.33(dd, 1H, $J_{gem}$=12.45 Hz, H-9), 4.16(dd, 1H, H-9'), 4.02(dd, 1H, $J_{5,6}$=10.62 Hz, H-6), 3.81(s, 3H, COOMe), 3.62(m, 1H, $J_{4,5}$=10.25 Hz, H-4), 3.48(q, 1H, H-5), 3.34(s, 3H, OMe), 2.88(dd, 1H, $J_{3e,4}$=4.40 Hz, H-3e), 2.16-2.04(5s, 15H, 3OAc, NAc, SMe), 1.67(t, 1H, $J_{3a,3e}=12.64$ Hz, H-3a)

2-(Trimethylsilyl)ethyl-O-(methyl 5-acetamido-7,8,9-tri-O-acetyl-3,5-dideoxy-4-O-methyl-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 5A)

Compound 49 (1.20 g, 2.43 mmol) and Compound 16 (0.90 g, 1.19 mmol) were dissolved in acetonitrile (12 ml), Molecular Sieves 3A (4.0 g) was added and the mixture was stirred overnight. After cooling to $-15°$ C., dimethyl(methylthio)sulfonium triflate (50%, 3.5 g) was added and the mixture was stirred at $-15°$ C. for 2 days. After a completion of the reaction was confirmed by T.L.C. (dichloromethane:metahnol=18:1), the reaction solution was filtered through Celite and the combined filtrate and washings were extracted with dichloromethane. The dichloromethane layer was washed with sodium carbonate and water, dehydrated with anhydrous sodium sulfate, separated by filtration and washed with dichloromethane. The filtrate and washings were combined. The resultant syrup was subjected to column chromatography with an eluting solvent (ethyl acetate:hexane=3:1) to afford Compound 5A (0.54 g, 37.8%).

$C_{57}H_{73}NO_{25}Si$ (1200.28) $[α]_D=+12.58°$ (c 0.906, $CHCl_3$)

IR $ν^{film}_{max}cm^{-1}$:3800–3170 (NH), 3170–2800 (CH), 1740 (ester), 1680, 1560 (amide), 880, 860 ($Me_3Si$), 720 (phenyl) 270 MHz $^1$H-NMR($CDCl_3$)

Lac unit: δ8.20–7.38(m, 15H, 3BzO), 5.38(dd, 1H, $J_{1,2}=8.06$ Hz, $J_{2,3}=9.53$ Hz, H-2), 4.88(dd, 1H, $J_{gem}=11.9$ Hz, $J_{5,6}=2.93$ Hz, H-6), 4.76(d, 1H, H-1), 4.70(d, 1H, $J_{1',2'}=7.88$ Hz, H-1), 4.63(dd, 1H, $J_{5,6}=5.68$ Hz, H-6), 3.70(ddd, 1H, $\underline{CH}CH_2Si$), 0.98(m, 2H, $CH_2\underline{CH_2}Si$), 0.00(s, 9H, $Me_3Si$)

Neu5Ac unit :5.80(d, 1H, $J_{5,NH}=7.88$ Hz, NH), 5.43(m, 1H, H-8), 5.06(dd, 1H, H-7), 3.90(s, 3H, COOMe), 3.45(s, 3H, $CH_3$), 2.93(dd, 1H, $J_{3a,3e}=13.19$ Hz, $J_{3e,4}=4.22$ Hz, H-3e), 1.86(t, 1H, H-3a), 2.26–2.08(4s, 12H, 3AcO,Acn)

2-(Trimethylsilyl)ethyl O-(methyl 5-acetamido-7,8,9-tri-O-acetyl-3,5-dideoxy-4-O-methyl-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 5B)

Compound 5A (0.50 g, 0.42 mmol) was dissolved in pyridine (9 ml), acetic anhydride (6 ml) was added and the mixture was stirred at room temperature overnight. After a completion of the reaction was confirmed by T.L.C. (dichloromethane:methanol=18:1), methanol was added to decompose exessive reagent and concentrated under reduced pressure. The resultant syrup was subjected to column chromatogrpahy with an eluting solvent (dichloromethane:methanol=200:3) to afford Compound 5B (0.48 g, 87.2%).

$C_{63}H_{79}NO_{28}Si$ (1326.40) $[α]_D=+20.38°$ (c 0.726, $CHCl_3$)

IR $ν^{film}_{max}cm^{-1}$:3700–3160 (NH), 3160–2800 (CH), 1740 (ester), 1660, 1540 (amide), 860, 840 ($Me_3Si$), 710 (phenyl) 270 MHz $^1$H-NMR($CDCl_3$)

Lac unit :δ8.19–7.38(m, 15H, 3BzO), 5.59(t, 1H, $J_{2,3}=J_{3,4}=9.53$ Hz, H-3), 5.33(dd, 1H, $J_{1,2}=7.70$ Hz, H-2), 5.15(dd, 1H, $J_{1',2'}=8.06$ Hz, $J_{2',3'}=10.26$ Hz, H-2'), 5.12(dd, 1H, H-4'), 5.00(d, 1H, H-1), 4.78(d, 1H, H-1), 4.71(dd, 1H, $J_{3',4'}=3.30$ Hz, H-3'), 3.68(ddd, 1H, $\underline{CH}CH_2Si$), 0.98(m, 2H, $CH_2\underline{CH_2}Si$), 0.00(s, 9H, $Me_3Si$)

Neu5Ac unit :5.69(m, 1H, $J_{7,8}=9.16$ Hz, H-8), 5.45(dd, 1H, $J_{6,7}=2.57$ Hz, H-7), 3.82(s, 3H, COOMe), 3.68(m, 1H, H-4), 3.40(s, 3H, OMe), 2.86(dd, 1H, $J_{3a,3e}=12.46$ Hz, $J_{2e,4}=4.03$ Hz, H-3e), 2.29–2.04(7s, 21H, 6OAc, NAc), 1.47(t, H-3a)

O-(Methyl 5-acetamido-7,8,9-tri-O-acetyl-3,5-dideoxy-4-O-methyl-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 5C)

Compound 5B (0.44 g, 0.33 mmol) was disolved in dichloromethane (10 ml), boron trifluoride diethyl ether (0.5 ml) was added dropwise under ice-cooling and the mixture was stirred at 0° C. for 4 hrs. After a completion of the reaction was confirmed by T.L.C. (dichloromethane:methanol=18:1), the reaction solution was extracted with dichloromethane. The dichloromethane layer was washed with successive sodium carbonate and water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=45:1) to afford Compound 5C (0.36 g, 88.5%).

$C_{58}N_{67}NO_{28}$ (1226.16) $[α]_D=+61.01°$ (c 0.118, $CHCl_3$)

IR $ν^{film}_{max}cm^{-1}$:3700–3160 (OH, NH), 3160–2800 (CH), 1740 (ester), 1660, 1540 (amide), 710 (phenyl)

O-(Methyl 5-acetamido-7,8,9-tri-O-acetyl-3,5-dideoxy-4-O-methyl-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 5D)

Compound 5C (0.30 g, 0.24 mmol) was dissolved in dichloromethane (3 ml), trichloroacetonitrile (0.9 ml) and 1,8-diazabicyclo[5.4.0]-undec-7-ene (35 mg) were added and the mixture was stirred at 0° C. for 2 hrs. After a completion of the reaction was confirmed by T.L.C. (dichloromethane:methanol=18:1), the reaction solution was concentrated under reduced pressure. The resultant syrup was subjected to column chromatography with an eluting solvent (dichloromethane:methanol=60:1) to afford Compound 5D (0.27 g, 80.6%).

$C_{60}H_{67}N_2O_{28}Cl_3$ (1370.54) $[α]_D=54.57°$ (c 1.092, $CHCl_3$)

IR $ν^{film}_{max}cm^{-1}$: 3700–3170 (NH), 3170–2800 (CH), 1740 (ester), 1670, 1550 (amide), 710 (phenyl) 270 MHz $^1$H-NMR($CDCl_3$)

Lac unit:δ8.55(s, 1H, C=NH), 8.12–7.27(m, 15H, 3BzO), 6.66(d, 1H, $J_{1,2}=3.66$ Hz, H-1), 5.85(t, 1H, $J_{2,3}=J_{3,4}=9.71$ Hz, H-3), 5.28(dd, 1H, $J_{1,2}=3.85$ Hz, H-2), 5.07(dd, 1H, $J_{1',2'}=7.88$ Hz, $J_{2',3'}=10.26$ Hz, H-2'), 5.03(dd, 1H, H-4'), 4.93(d, 1H, H-1'), 4.60(dd, 1H, $J_{3',4'}=3.30$ Hz, H-3')

Neu5Ac unit :5.54(m, 1H, $J_{7,8}=8.97$ Hz, H-8), 5.33(dd, 1H, $J_{6,7}=2.39$ Hz, H-7), 5.25(d, $J_{5,NH}=7.88$ Hz, NH), 3.70(s, 3H, COOMe), 3.56(m, 1H, H-4) 3.28(s, 3H, OMe), 2.74(dd, 1H, $J_{3a,3e}=12.82$ Hz, $J_{3e,4}=4.58$ Hz, H-3e), 2. 16-1.92(7s, 21H, 6AcO, AcN), 1.70(t, 1H, $J_{3a,3e}=12.36$ Hz, H-3a)

O-(Methyl 5-acetamido-7,8,9-tri-O-acetyl-3,5-dideoxy-4-O-methyl-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1) -(2S,3R,4E)-2azido-3-benzoyl-4-octadecene-1,3-diol (Compound 5E)

Compound 5D (0.12 g, 0.09 mmol) and Compound 17 (0.08 g, 0.19 mmol) were dissolved in dichloromethane (3.5 ml), Molecular Sieves 4A type AW 300 (2.5 g) was added and the mixture was stirred at room temperature for 30 minutes. Then boron trifluoride diethyl ethy (0.05 ml) was added dropwise under ice-cooling and the mixture was stirred at 0° C. for 5 hrs. After a completion of the reaction was confirmed by T.L.C. (dichloromethane:methanol=18:1), the reaction solution was filtered through Celite and the combined filtrate and washings were extracted with dichloromethane. The dichloromethane layer was washed with successive sodium carbonate and water, dehydrated with anhydrous sodium sulfate, separated by filtration and washed with dichloromethane. The filtrate was washings were combined. The resultant syrup was subjected to column chromatography with an eluting solvent (dichloromethane:methanol=70:1) to afford Compound 5E (0.10 g, 70.0%).

$C_{83}H_{104}N_4O_{30}$ (1637.75) $[\alpha]_D=+10.01°$ (c 1.298, CHCl$_3$)

IR $\nu^{film}_{max}$cm$^{-1}$: 3700-3160 (NH), 3160-2800 (CH), 2100 (N$_3$), 1740 ( ester), 1680, 1550 (amide), 710 (phenyl)

270 MHz $^1$-NMR(CDCl$_3$)

Lac unit : δ8.06-7.27(m, 20H, 4BzO), 5.49(t, 1H, $J_{2,3}=9.89$ Hz, H-3), 5.25(dd, 1H, $J_{1,2}=7.33$ Hz, H-2), 5.04(dd, 1H, H-2'), 5.01(dd, 1H, H-4'), 4.93(d, 1H, $J_{1',2'}=7.69$ Hz, H-1'), 4.66(d, 1H, H-1), 4.40(dd, 1H, J $_{2',3'}=10.26$ Hz, $J_{3',4'}=3.30$ Hz, H-3')

Neu5Ac unit :5.61(m, 1H, H-8), 3.69(s, 3H, COOMe), 3.54(m, 1H, H-4), 3.28(s, 3H, OMe), 2.73(dd, 1H, $J_{3a,3e}=12.45$ Hz, $J_{3e,4}=3.67$ Hz, H-3e), 2. 24-1.98(7s, 24H, 6AcO, AcN)

Sphingosine unit :5.66(m, 1H,$J_{5,6}=J_{5,6'}=6.96$ Hz, H-5), 1.24(s, 22H , 11CH$_2$), 0.87(t, 3H, CH$_3$)

O-(Methyl 5-acetamido-7,8,9-tri-O-acetyl-3,5-dideoxy-4-O-methyl -D-glycero-α-D-galacto-2-nonulopyranosylonate)-(2→3)-O-(2, 4-di-O-acetyl-6-O-benzoyl-β-D-galactopyranosyl)-(1→4)-O-(3O-acetyl-2,6-di-O-benzoyl-β-D-glucopyranosyl)-(1→1)-(2S,3R,4E)-3-benzoyl-2-octadecanamide-4-octadecene-1,3-diol (Compound 5F)

Compound 5E (100 mg, 0.06 mmol) was dissolved in a mixed solvent of 5/1 pyridine/water (12 ml) and the solution was stirred at room temperature for 25 hrs. while blowing hydrogen sulfide gas. After a completion of the reaction was confirmed by T.L.C. (ethyl acetate), the reaction solution was evaporated under reduced pressure to dryness. The solid was dissolved in dichloromethane (6 ml), stearic acid (58 mg, 0.20 mmol) and WSC (58 mg) were added and the mixture was stirred at room temperature overnight. After a completion of the reaction was confirmed by T.L.C. (dichloromethane:-methanol=18:1), the reaction solution was extracted with dichloromethane. The dichloromethane layer was washed with water, dehydrated with anhydrous sodium sulfate, separated by filtration, and washed with dichloromethane. The combined filtrate and washings were concentrated unde reduced pressure. The resultant syrup was subjected to column chromatography with an eluting solvent (dichloromethane:methanol=75:1) to afford Compound 5F (93 mg, 81.3%).

$C_{101}H_{140}N_2O_{31}$ (1878.22) $[\alpha]_D=+181.19°$ (c 1.170, CHCl$_3$)

IR $\nu^{film}_{max}$cm$^{-1}$: 3700-3150 (NH), 3150-2800 (CH), 1740 (ester), 1660, 1530 (amide), 710 (phenyl) 270 MHz $^1$H-NMR(CDCl$_3$)

Lac unit : δ8.06-7.25(m, 20H, 4BzO), 5.47(t, 1H, $J_{2,3}=9.89$ Hz, H-3), 5.19(dd, 1H, H-2), 5.00(dd, 1H, $J_{2',3'}=9.89$ Hz, H-2'), 5.00(dd, 1H, H -4'), 4.84(d, 1H, $J_{1',2'}=8.06$ Hz, H-1'), 4.61(d, 1H, $J_{1,2}=8.06$ Hz, H-1), 4.59(dd, 1H, $J_{3',4'}=3.30$ Hz, H-3')

Neu5Ac unit :5.53(m, 1H, H-8), 5.35(dd, 1H, $J_{6,7}=2.57$ Hz, $J_{7,8}=9.16$ H z, H-7), 3.70(s, 3H, COOMe), 3.56(m, 1H, H-4), 3.29(s, 3H, OMe), 2.73(dd, 1H, $J_{3a,3e}=12.64$ Hz, $J_{3e,4}=4.21$ Hz, H-3e), 2.13-1.93 (7s, 21H, 6AcO, Ac N)

Cer unit :5.76(td, 1H, $J_{5,6}=J_{5,6'}=6.96$ Hz, H-5), 1.26(s, 50H, 25CH$_2$), 0.87(t, 6H, 2CH$_3$)

O-(5-Acetamido-3,5-dideoxy-4-O-methyl-D-glycero-α-D-galacto-2 -nonulopyranosylonic acid)-(2→3)-O-(β-D-galactopyranosyl)-(1→4)-O -(β-D-glucopyranosyl)-(1→1)-(2S,3R,4E)-2-octadecanamide-4-octadecene-1,3-diol (Compound 5)

Compound 5F (85 mg, 0.045 mmol) was dissolved in methanol (3ml), 28% sodium methylate solution (5 drops) was added and the mixture was stirred at room temperature for 22 hrs. Water (0.5 ml) was added and the mixture was stirred for further 20 hrs. After a completion of the reaction was confirmed by T.L.C. (butanol:ethanol:water=4:2:1), the reaction solution was neutralized with ion exchange resin IR-120 (H$^+$) and concentrated under reduced pressure. The resultant syrup was subjected to gel filtration with Sephadex LH-20 to afford Compound 5 (51 mg, 94.8%).

$C_{60}H_{110}N_2O_{21}$ (1195.53) $[\alpha]_D=+2.99°$ (c 0.958, methanol:dichlorometehane=1:1)

IR $\nu^{KBr}_{max}$cm$^{-1}$: 3700-2800 (OH, NH), 2920, 2850 (Me,methylene), 1730 (C=O), 1630, 1540 (amide) 270 MHz $^1$H-NMR(CDCl$_3$)

Lac unit : δ4.43(d, 1H, $J_{1',2'}=8.06$ Hz, H-1'), 4.10(d, 1H, $J_{1,2}=8.06$ Hz, H-1)

Neu5Ac unit :3.40(s, 3H, OMe), 2.99(broad, 1H, H-3e), 2.00(s, 3H, A cN)

Cer unit :5.69(td, 1H, $J_{5,6}=J_{5,6'}=6.60$ Hz, H-5), 4.19(dd, 1H, H-4), 1.28(s, 50H, 25CH$_2$), 0.89(t, 6H, 2CH$_3$)

EXAMPLE 6

Methyl(methyl 5-acetamido-9O-t-butyldimethylsilyl-3,5-dideoxy-2-thio-D-glycero-α-D-galacto-2-nonulopyranosid)onate (Compound 50)

Compound 46 (2.06 g, 5.83 mmol) was dissolved in pyridine (40 ml) and the solution was cooled to 0° C. Then t-bityldimethylsilyl chloride (1.7 g, 1.13 mmol) was added and the mixture was stirred at 0° C. for 2 hrs. After a completion of the reaction was confirmed by T.L.C. (dichloromerhane:methanol=10:1), methanol was added and the mixture was stirred for one hour and concentrated under reduced pressure. The resultant syrup was subjected to column chromatography with an eluting solvent (ethyl acetate:hexane=4:1) to afford Compound 50 (2.54 g, 93.2%).

C$_{19}$H$_{37}$NO$_8$SSi (467.65) [α]$_D$=24.20° (c 0.818, CHCl$_3$)

IR ν$^{film}{}_{max}$cm$^{-1}$: 3700–3160 (NH, OH), 3160–2800 (CH), 1730 (ester), 1650, 1540 (amide), 840, 820 (Si)

$^1$H-NMR(CDCl$_3$)3.75(s, 3H, COOMe), 3.22(dd, 1H, J$_{5,6}$=10.25 Hz, H-6), 2.71 (dd, 1H, J$_{3a,3e}$=13.01 Hz, J$_{3e,4}$=4.58 Hz, H-3e), 2.01, 1.92(2s, 6H, NAc SM e), 0.82(s, 9H, t-BuSi), 0.00(s, 6H, Me$_2$Si)

Methyl)methyl 5-acetamido-4,8-di-O-benzoyl-9O-t-butyldimethylsilyl-3,5-dideoxy-2-thio-D-glycero-α-D-galacto-2-nonulopyranosid)onate (Compound 51)

Compound 50 (0.10 g, 0.21 mmol) was dissolved in a mixed solvent of 3/1 dichloromethane/pyridine (4 ml) and the solution was cooled to −5° C. Benzoyl chloride (0.15 ml, 1.29 mmol) diluted with dichloromethane (1 ml) was added and the mixture was stirred at −5° C. for 1.5 hrs. After a completion of the reaction was confirmed by T.L.C. (dichloromethane:methanol=30:1), methanol was added and the reaction solution was concentrated under reduced pressure. The resultant syrup was extracted with dichloromethane, the organic layer was washed with HCl and water, dehydrated with anhydrous sodium sulfate, separated by filtration and concentrated under reduced pressure. The resultant syrup was subjected to column chromatography with an eluting solvent (ethyl acetate:hexane=1:3) to afford Compound 51 (0.11 g, 76.1%).

C$_{33}$H$_{45}$NO$_{10}$SSi (675.87) [α]$_D$=−11.64° (c 0.704, CHCl$_3$)

IR ν$^{film}{}_{max}$cm$^{-1}$: 3700–3160 (NH), 3160–2800 (CH), 1720 (ester), 1630, 1550 (amide), 830, 810 (Si), 710 (phenyl)

$^1$H-NMR(CDCl$_3$)8.13–7.47(m, 10H, 2OBz), 6.29(d, 1H, J$_{5,NH}$=7.87 Hz, NH), 5.46(m, 1H, H-8), 5.28(ddd, 1H, J$_{3e,4}$=4.58 Hz, H-4), 4.83(d, 1H, OH-7), 4.18(q, 1H, J$_{4,5}$=J$_{5,6}$=J$_5$, $_{NH}$=10.26 Hz, H-5), 4.18–4.05(m, 3H, H-7.9.9'), 3.51(dd, 1H, H-6), 3.28(s, 3H, COOMe), 2.90(dd, 1H, J$_{3a,3e}$=12.54 Hz, H-3e), 2.25, 1.92(2s, 6H, NAc, SMe), 0.89(s, 9H, t-BuSi), 0.00(s, 6H, Me$_2$Si)

Methyl(methyl 5-acetamido-4,8-di-O-benzoyl-3,5-dideoxy-2-thio-D-glycero-α-D-galacto-2-nonulopyranosid)onate (Compound 52)

Compound 51 (72 mg, 0.10 mmol) was dissovled in an aqueous solution of 80% acetic acid (3 ml) and the solution was stirred at 40° C. for 2 hrs. After a completion of the reaction was confirmed by T.L.C. (dichloromethane:methanol=18:1), the reaction solution was concentrated under reduced pressure. The resultant syrup was subjected to column chromatography with an eluting solvent (ethyl acetate :hexane=2:1) to afford Compound 52 (51 mg, 85.3%).

C$_{27}$H$_{31}$NO$_{10}$S (561.60) [α]$_D$=−3.04° (c 0.656, CHCl$_3$)

IR ν$^{film}{}_{max}$cm$^-$: 3700–3150 (NH), 3150–2800 (CH), 1720 (ester), 1650, 1540 (amide), 710 (phenyl)

$^1$H-NMR(CDCl$_3$, CD$_3$OD) 8.10–7.32(m, 10H, 2OBz), 5.41(m, 1H, J$_{7,8}$=8.97 Hz, H-8), 5.19(ddd, 1H, J$_{3e,4}$=4.58 Hz, H-4), 4.27(t, 1H, J$_{4,5}$=J$_{5,6}$=10.44 Hz, H-5), 4.12–3.89(m, 3H, H-7.9.9'), 3.55(dd, 1H, H-6), 3.32(s, 3H, COOMe), 2.89(dd, 1H, J$_{3a,3e}$=12.45 Hz, H-3e), 2.18, 1.90(2s, 6H, SMe, NAc), 2.08 (t, 1H, H-3a)

Methyl(methyl 5-acetamido-4,8-di-O-benzoyl-3,5-dideoxy-9O-methyl-2-thio-D-glycero-α-D-galacto-2-nonulopyranosid)onate (Compound 53)

Compound 52 (1.50 g, 2.67 mmol) was dissolved in dichloromethane (60 ml) and the solution was cooled to 0° C. DTBMP (1.5 g, 7.30 mmol) and trimethyloxonium tetrafluoroborate (1.0 g, 6.76 mmol) were added and the mixture was stirred at 0° C. for 30 minutes. After a completion of the reaction was confirmed by T.L.C. (dichloromethane:methanol=30:1), methanol was added and the reaction solution was concentrated under reduced pressure. The resultant syrup was subjected to column chromatography with an eluting solvent (ethyl acetate:hexane=1:4) to afford Compound 53 (1.47 g, 95.6%).

C$_{28}$H$_{33}$NO$_{10}$S (575.63) [α]$_D$=+5.91° (c 1.150, CHCl$_3$)

IR ν$^{film}{}_{max}$cm$^{-1}$: 3700–3160 (CH), 1730 (ester), 1650, 1550 (amide), 710 (phenyl)

$^1$H-NMR(CDCl$_3$)8.08–7.39(m, 10H, 2Bz), 6.20(d, 1H, J$_{5,NH}$=7.87 Hz, NH), 5.49(m, 1H, H-8), 5.21(ddd, 1H, J$_{3e,4}$=4.76 Hz, J$_{4,5}$=10.62 Hz, H-4), 4.80(d, 1H, OH-7), 4.19(q, 1H, H-5), 3.91–3.81(m, 2H, H-9,9'), 3.47(dd, 1H, J$_{5,6}$=10.44 Hz, J$_{6,7}$=1.56 Hz, H-6), 3.34, 3.23(2s, 6H, COOMe, OMe), 2.84(dd, 1H, J$_{3a,3e}$=12.64 Hz, H-3e), 2.17, 1.91(2s, 6H, NAc, SMe)

Methyl(methyl 5-acetamido-7-O-acetyl-4,8-di-O-benzoyl-3,5-dideoxy-9-O-methyl-2-thio-D-glycero-α-D-galacto-2-nonulopyranosid)onate (Compound 54)

Compound 53 (1.42 g, 2.47 mmol) was dissolved in pyridine (15 ml), acetic anhydride (12 ml) was added and the solution was stirred at room temperature overnight. After a completion of the reaction was confirmed by T.L.C. (dichloromethane:methanol=30:1), methanol was added and the reaction solution was concentrated under reduced pressure. The resultant syrup was extracted with dichloromethane, the dichloromethane layer was washed with HCl and water, dehydrated with anhydrous sodium sulfate, separated by filtration and washed with dichloromethane. The combined filtrate and washings were concentrated under reduced pressure. The resultant syrup was subjected to column chromatography with an eluting solvent (ethyl acetate :hexane=2:3) to afford Compound 54 (1.48 g, 97.4%).

C$_{30}$H$_{35}$NO$_{11}$S (617.70) [α]$_D$=+69.31° (c 0.906, CHCl$_3$)

IR ν$^{film}{}_{max}$cm$^{-1}$: 3700–3150 (NH), 3150–2800 (CH), 1730 (ester), 1670, 1540 (amide), 710 (phenyl)

$^1$H-NMR(CDCl$_3$)8.08–7.35(m, 10H, 2Bz), 5.66(m, 1H, J$_{7,8}$=6.98 Hz, J$_{8,9}$=3.41 Hz, J$_{8,9'}$=5.76 Hz, H-8), 5.54(dd, 1H, J$_{6,7}$=2.33 Hz, H-7), 5.47(d, 1H, J$_{5,NH}$=10.06 Hz, NH), 5.12(ddd, 1H, J$_{4,5}$=10.44 Hz, H-4), 4.35(q, 1H, H-5), 4.00(dd, 1H, J$_{5,6}$=10.67 Hz, H-6), 3.85(dd, 1H, J$_{gem}$=11.00 Hz, H-9), 3.56(dd , 1H, H-9'), 3.54, 3.33(2s, 6H, COOMe, OMe), 2.93(dd, 1H, J$_{3a,3e}$=12.56 H Z, J$_{3e,4}$=4.66 Hz, H-3e), 2.20, 2.19, 1.76(3s, 9H, 0Ac, NAc, SMe)

2-(Trimethylsilyl)ethyl O-(methyl 5-acetamido-7-O-acetyl-4,8-di-O-benzoyl-3,5-dideoxy-9-O-methyl-D-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 6A)

Compound 54 (1.00 g, 1.62 mmol) and Compound 16 (0.62 g, 0.82 mmol) were dissolved in acetonitrile (12 ml), Molecular Sieves 3A (2.5 g) was added and the mixture was stirred overnight. After cooling to −15° C. dimethyl(methylthio)sulfonium triflate (60%, 3.0 g) was added and the mixture was stirred at −15° C. for 2 days. After a completion of the reaction was confirmed by T.L.C. (dichloromethane:methanol=20:1), the reaction solution was filtered through Celite and the combined filtrate and washings were extracted with dichloromethane. The dichloromethane layer was washed with sodium carbonate and water, dehydrated with anhydrous sodium sulfate, separated by filtration and washed with dichloromethane. The filtrate and washings were combined. The resultant syrup was subjected to column chromatography with an eluting solvent (ethyl acetate:hexane=5:4) to afford Compound 6A (0.43 g, 39.8%).

$C_{67}H_{77}NO_{25}Si$ (1324.46) $[\alpha]_D = +27.83°$ (c 0.934, $CHCl_3$)

IR $\nu^{film}_{max}cm^{-1}$: 3700–3160(NH, OH), 3160–2800 (CH), 1730 (ester ), 1670, 1530 (amide), 860, 840 ($Me_3Si$), 710(phenyl) 270 MHz $^1H$-NMR($CDCl_3$)

Lac unit: δ8.21–7.37(m, 25H, 5BzO), 5.37(dd, 1H, $J_{1,2}=8.06$ Hz, $J_{2,3}=9.52$ Hz, H-2), 4.87(dd, 1H, $J_{gem}=11.72$ Hz, $J_{5,6}=3.11$ Hz, H-6), 4.77(d, 1H, H-1), 4.76(d, 1H, $J_{1',2'}=7.69$ Hz, H-1'), 4.62(dd, 1H, $J_{5,6}=5.68$ Hz, H-6), 0.98(m, 2H, $CH_2CH_2Si$), 0.00(s, 9H, $Me_3Si$)

Neu5Ac unit :5.74–5.65(m, 2H, H-4,8), 5.17(dd, 1H, H-7), 3.39, 3.35 (2s, 6H, COOMe, OMe), 2.87(dd, 1H, $J_{3a,3e}=12.82$ Hz, $J_{3e,4}=4.21$ Hz, H-3e), 2.31, 1.92(2s, 6H, AcO, AcN)

2-(Trimethylsilyl)ethyl O-(methyl 5-acetamido-7-O-acetyl-4,8-di-O-benzoyl-3,5-dideoxy-9-O-methyl-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound 6B)

Compound 6A (0.38 g, 0.29 mmol) was dissolved in pyridine (14 ml), acetic anhydride (11 ml) was added and the mixture was stirred at room temperature overnight. After a completion of the reaction was confirmed by T.L.C. (dichloromethane:methanol=20:1), methanol was added to decompose excessive reagent and concentrated under reduced pressure. The resultant syrup was subjected to column chromatography with an eluting solvent (dichloromethane:methanol=100:1) to afford Compound 6B (0.40 g, 96.2%.

$C_{73}H_{83}NO_{28}Si$ (1450.57) $[\alpha]_D = +37.36°$ (c 0.562, $CHCl_3$)

IR $\nu^{film}_{max}cm^{-1}$: 3700–3150 (NH), 3150–2800 (CH), 1740 (ester), 1680, 1530 (amide), 860, 840 ($Me_3Si$), 710 (phenyl) 270 MHz $^1H$-NMR($CDCl_3$)

Lac unit: δ8.16–7.29(m, 25H, 5BzO), 5.60(t, 1H, $J_{2,3}=J_{3,4}=9.52$ Hz, H-3), 5.37(dd, 1H, $J_{1,2}=8.06$ Hz, H-2), 5.20(dd, 1H, $J_{2',3'}=9.52$ Hz, H-2'), 5.10(d, 1H, $J_{1',2'}=7.88$ Hz, H-1'), 5.08(d, 1H, H-4'), 4.80(d, 1H, H-1), 0.97(m, 2H, $CH_2CH_2Si$), 0.00(s, 9H, $Me_3Si$)

Neu5Ac unit: 5.86(m, 1H, H-8), 5.73(dd, 1H, $J_{6,7}=2.57$ Hz, H-7), 3.42, 3.39(2s, 6H, COOMe, OMe), 2.83(dd, 1H, $J_{3a,3e}=12.36$ Hz, $J_{3e,4}=4.48$ Hz, H-3e), 2.45–1.87(5s, 15H, 4AcO, AcN)

O-(Methyl 5-acetamido-7-O-acetyl-4,8-di-O-benzyl-3,5-dideoxy-9-O-methyl-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 6C)

Compound 6B (0.39 g, 0.39 mmol) was dissolved in dichloromethane (10 ml), boron trifluoride diethyl ether (0.5 ml) was added dropwise under ice-cooling and the mixture was stirred at 0° C. for 5 hrs. After a completion of the reaction was confirmed by T.L.C. (dichloromethane:methanol=20:1), the reaction solution was extracted with dichloromethane. The dichloromethane layer was washed with successive sodium carbonate and water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=60:1) to afford Compound 6C (0.34 g, 9.37%).

$C_{88}H_{71}NO_{28}$ (1350.33) $[\alpha]_D = +67.93°$ (c 1.466, $CHCl_3$)

IR $\nu^{film}_{max}cm^{-1}$: 3700–3140 (OH, NH), 3140–2800 (CH), 1740 (ester ), 1670, 1530 (amide), 710 (phenyl)

O-(Methyl 5-acetamido-7-O-acetyl-4,8-di-O-benzoyl-3,5-dideoxy-9-O-methyl-2-thio-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 6D)

Compound 6C (0.34 g, 0.25 mmol) was dissolved in dichloromethane (4 ml), trichloroacetonitrile (1.0 ml) and 1,8-diazabicyclo[5.4.0]-undec-7-ene (40 mg) were added and the mixture was stirred at 0° C. for 2 hrs. After a completion of the reaction was confirmed by T.L.C. (dichloromethane:methanol=20:1), the reaction solution was concentrated under reduced pressure. The resultant syrup was subjected to column chromatography with an eluting solvent (dichloromethane:methanol=90:1) to afford Compound 6D (0.33 g, 87.8%).

$C_{70}H_{71}N_2O_{28}Cl_3$ (1494.72) $[\alpha]_D = +72.30°$ (c 0.686. $CHCl_3$)

IR $\nu^{film}_{max}cm^{-1}$: 3700–3160 (NH), 3160–2800 (CH), 1750 (ester), 1680, 1540 (amide), 710 (phenyl) 270 MHz $^1H$-NMR ($CDCl_3$)

Lac unit :δ8.56(s, 1H, C=NH), 8.11–7.08(m, 25H, 5OBz), 6.68(d, 1H, $J_{1,2}=3.67$ Hz, H-1), 5.86(t, 1H, $J_{2,3}=J_{3,4}=9.53$ Hz, H-3), 5.32(dd, 1H, $J_{2,3}=10.26$ Hz, H-2), 5.02(dd, 1H, $J_{1',2'}=7.88$ Hz, $J_{2',3'}=9.71$ Hz, H-2'), 5.02(d, 1H, H-1'), 4.97(dd, 1H, H-4'), 4.78(dd, 1H, $J_{3',4'}=3.12$ Hz, H-3')

Neu5Ac unit :5.73(m, 1H, H-8), 5.62(dd, 1H, $J_{6,7}=2.75$ Hz, $J_{7,8}=9.71$ Hz, H-7), 3.72(dd, 1H, H-6), 3.32, 3.26(2s, 6H, COOMe, OMe), 2.72(dd, 1H, $J_{3a,3e}=12.64$ Hz, $J_{3c,4}=4.58$ Hz, H-3e), 2.32–1.75(5s, 15H, 4AcO, AcN) O-(Methyl 5-acetaido-7-O-acetyl-4,8-di-O-benzoyl-3,5-dideoxy-9O-methyl-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D- glucopyranosyl)-(1→1)-(2S,3R,4E)-2-azido-3-benzoyl-4-octadecene-1,3-diol (Compound 6E)

Compound 6D (0.20 g, 0.13 mmol) and Compound 17 (0.10 g, 0.23 mmol) were dissolved in dichloromethane (4 ml), Molecular Sieves 4A type AW 300 (2.5 g) was added and the mixture was stirred at room temperature for 30 minutes. Then boron trifluoride diethyl ether (0.07 ml) was added dropwise under ice-cooling and the mixture was stirred at 0° C. for 5 hrs. After a completion of the reaction was confirmed by T.L.C. (dichloromethane:methanol=20:1), the reaction solution was filtered through Celite and the combined filtrate and washings were extracted with dichloromethane. The dichloromethane layer was washed with successive sodium carbonate and water, dehydrated with anhydrous sodium sulfate, separated by filtration and washed with dichloromethane. The filtrate and washings were combined. The resultant syrup was subjected to column chromatography with an eluting solvent (dichloromethane:methanol=120:1) to afford Compound 6E (0.19 g, 80.6%).

$C_{93}H_{108}N_4O_{30}$ (1761.92) $[\alpha]_D = +23.60°$ (c 1.966, $CHCl_3$)

IR $\nu^{film}_{max}cm^{-1}$: 3700–3140 (NH), 3140–2800 (CH), 2100 ($N_3$), 1730 (ester), 1680, 1530 (amide), 710 (phenyl) 270 MHz $^1$H-NMR($CDCl_3$)

Lac unit: $\delta$8.06–7.17 (m, 30H, 6BzO), 5.52(t, 1H, H-3), 5.29(dd, 1H, $J_{1,2}$=7.88 Hz, $J_{2,3}$=9.34 Hz, H-2), 5.13(dd, 1H, H-2'), 4.99(d, 1H, $J_{1',2'}$=7.70 Hz, H-1'), 4.96(d, 1H, H-4'), 4.77(dd, 1H, $J_{2',3'}$=9.52 Hz, $J_{3',4'}$=3.30 Hz, H-3'), 4.71(d, 1H, H-1)

Neu5Ac unit: 5.74(m, 1H, H-8), 5.62(dd, 1H, $J_{6,7}$=2.83 Hz, $J_{7,8}$=9.42 Hz, H-7), 3.42(dd, 1H, $J_{8,9}$=3.67 Hz, $J_{gem}$=3.67 Hz, H-9), 3.30, 3.27(2s, 6H, COOMe, OMe), 2.72(dd, 1H, $J_{3a,3e}$=12.46 Hz, $J_{3e,4}$=4.40 Hz, H-3e), 2.32–1.75(5s, 15H, 4AcO, AcN)

Sphingosine unit: 1.25(s, 22H, 11$CH_2$), 0.88(t, 3H, $CH_3$)

O-(Methyl 5-acetamido-7-Oacetyl-4,8-di-O-benzoyl-3,5-dideoxy-9-O-methyl-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S, 3R,4E)-3-benzoyl-2-octadecanamid-4-octadecene-1,3-diol (Compound 6F)

Compound 6E (150 mg, 0.08 mmol) was dissolved in a mixed solvent of 5/1 pyridine/water (18 ml) and the solution was stirred at room temperature for 48 hrs. while blowing hydrogen sulfide gas. After a completion of the reaction was confirmed by T.L.C. (dichloromethane:methano=18:1), the reaction solution was extracted with dichloromethane. The dichloromethane layer was washed with water, dehydrated with anhydrous sodium sulfate, separated by filtration, and washed with dichloromethane. The combined filtrate and washings were concentrated under reduced pressure. The resultant syrup was subjected to column chromatogrpahy with an eluting solvent (dichloromethane:methanol=110:1) to afford Compound 6F (142 mg, 83.5%).

$C_{111}H_{144}N_2O_{31}$ (2002.39) $[\alpha]_D = 34.03°$ (c 2.844, $CHCl_3$)

IR $\nu^{film}_{max}cm^{-1}$: 3700–3150 (NH), 3150–2800 (CH), 1730 (ester), 1670, 1530 (amide), 710 (phenyl) 270 MHz $^1$H-NMR($CDCl_3$)

Lac unit: $\delta$8.07–7.17(m, 30H, 6BzO), 5.50(t, 1H, $J_{2,3}$=$J_{3,4}$=9.71 Hz, H-3), 5.22(dd, 1H, H-2), 5.07(dd, 1H, $J_{1',2'}$=7.87 Hz, H-2), 4.97(d, 1H, H-1), 4.96(d, 1H, H-4'), 4.77(dd, 1H, $J_{2',3'}$=10.26 Hz, $J_{3',4'}$=3.30 Hz, H-3), 4.63(d, 1H, $J_{1,2}$=7.88 Hz, H-1)

Neu5Ac unit: 5.78(m, 1H, H-8), 5.63(dd, 1H, $J_{6,7}$=2.93 Hz, $J_{7,8}$=9.89 Hz, H-7), 4.30(q, 1H, $J_{4,5}$=$J_{5,6}$=$J_{5,NH}$=10.44 Hz, H-5), 3.71(dd, 1H, H-6), 3.45(dd, 1H, $J_{8,9}$=3.48 Hz, $J_{gem}$=11.18 Hz, H-9), 3.30, 3.27(2s, 6H, COOMe, OMe), 2.72(dd, 1H, $J_{3a,3e}$=12.27 Hz, $J_{3e,4}$=4.40Hz, H-3e), 2.30–1.75(5s, 15H, 4AcO, AcN)

Cer unit: 1.26(s, 50H, 25$CH_2$), 0.87(t, 6H, 2$CH_3$)

O-(5-Acetamido-3,5-dideoxy-9-O-methyl-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-2-octadecanamid-4-octadecene-1,3-diol (Compound 6)

Compound 6F (140 mg, 0.07 mmol) was dissolved in methanol (3.5 ml), 28% sodium methylate solution (5 drops) was added and the mixture was stirred at room temperature for 12 hours. Water (0.5 ml) was added and the mixture was stirred for further 6 hrs. After a completion of the reaction was confirmed by T.L.C. (butanol:ethanol:water=4:2:1), the reaction solution was neutralized with ion exchange resin IR-120 (H+) and concentrated under reduced pressure. The resultant syrup was subjected to gel filtration with Sephadex LH-20 to afford Compound 6 (73 mg, 87.2%).

$C_{60}H_{110}N_2O_{21}$ (1195.57) $[\alpha]_D = -0.49°$ (c 1.212, methanol:dichloromethane=1:1)

IR $\nu^{KBr}_{max}cm^{-1}$: 3700–2800 (OH, NH), 2940, 2850 (Me, methylene), 1730 (C=O), 1640, 1550 (amide) 270 MHz $^1$H-NMR($CDCl_3$)

Lac unit: $\delta$4.42(d, 1H, H-1'), 4.30 (d, 1H, $J_{1,2}$=7.32 Hz, H-1)

Neu5Ac unit: 3.41(s, 3H, OMe), 2.79(broad, 1H, H-3e), 2.03(s, 3H, NAc)

Cer unit: 5.68(td, 1H, $J_{5,6}$=$J_{5,6}$=6.60 Hz, H-5), 4.43(dd, 1H, $J_{4,5}$=7.32 Hz, H-4), 1.27(s, 50H, 25$CH_2$), 0.89(t, 6H, 2$CH_3$)

EXAMPLE 7

Methyl(methyl 5-acetamido-4,7-di-O-acetyl-3,5-dideoxy-8,9-O-isopropylidene-2-thio-D-glycero-α-D-galacto-2-nonulopyranosid)onate (Compound 55)

Compound 47 (2.5 g, 6.35 mmol) was dissolved in pyridine (20 ml), acetic anhydride (10 ml) was added and the mixture was stirred at room temperature overnight. After a completion of the reaction was confirmed by T.L.C. (dichloromethane:methanol=18:1), methanol was added to decompose excessive reagent and the reaction solution was concentrated under reduced pressure. The resultant syrup was subjected to column chromatography with an eluting solvent (ethyl acetate:hexane=1:1) to afford Compound 55 (3.0 g, 96.7%).

$C_{20}H_{31}NO_{10}S$ (477.3) $[\alpha]_D = 9.00°$ (c 1.110, $CHCl_3$)

IR $\nu^{film}_{max}cm^{-1}$: 3700–3170 (NH), 3170–2800 (CH), 1740 (ester), 1670, 1550 (amide), 850 (isopropylidene) 270 MHz $^1$H-NMR($CDCl_3$) $\delta$5.50(d, 1H, $J_{5,NH}$=9.90 Hz, NH), 5.39(dd, 1H, $J_{6,7}$=2.02 Hz, $J_{7,8}$=3.67 Hz, H-7), 4.96(ddd, 1H, $J_{3e,4}$=4.95 Hz, $J_{4,5}$=10.44 Hz, H-4), 4.37(ddd, 1H, H-8), 4.06(m, 3H, H-5,9,9'), 3.85(s, 3H, COOMe), 2.78 (dd, 1H, $J_{3a,3e}$=12.73 Hz, H-3e), 2.17–1.88(4s, 12H, SMe, 2OAc, NAc), 1.35, 1.34(2s, 6H, C-Me$_2$)

Methyl(methyl 5-acetamido-4,7-di-O-acetyl-3,5-dideoxy-2-thio-D-glycro-α-D-galacto-2-nonulopyranosid)onate (Compound 56)

Compound 55 (3.0 g, 6.29 mmol) was mixed with an aqueous solution of 80% acetic acid (30 ml) and the mixture was allowed to stand at room temperature for 2 days. After a completion of the reaction was confirmed by T.L.C. (dichloromethane:methanol=10:1), the reaction solution was concentrated under reduced pressure. The resultant syrup was subjected to column chromatography with an eluting solvent (ethyl acetate:hexane=4:1) to afford Compound 56 (2.0 g, 90.5%).

$C_{17}H_{27}NO_{10}S$ (437.2) $[α]_D$=+34.22° (c 0.818, CHCl$_3$)

IR $ν^{film}{}_{max}$cm$^{-1}$: 3700–3160 (OH, NH), 3160–2800 (CH), 1740 (ester), 1660, 1550 (amide)

270 MHz $^1$H-NMR(CDCl$_3$) δ6.15 (d, 1H, NH), 5.08 (dd, 1H, $J_{6,7}$=2.38 Hz, $J_{7,8}$=9.34 Hz, H-7), 4.87 (ddd, 1H, $J_{3a,4}$=11.36 Hz, $J_{3e,4}$=4.76 Hz, H-4), 4.25 (ddd, 1H, $J_{NH,5}J_{5,6}J_{4,5}$=10.26 Hz, H-5), 3.78 (dd, 1H, H-6), 3.71 (s, 3H, COOMe), 2.82 (dd, 1H, $J_{3a,3c}$=12.82 Hz, H-3e), 2.16–2.05 (3s, 12H, SMe, 2 OAc, NAc)

Methyl(methyl 5-acetamido-4,7-di-O-acetyl-3,5-dideoxy-8,9-di-O-methanesulfonyl-2-thio-D-glycero-α-D-galacto-2-nonulopyranosid)onate (Compound 57)

Compound 56 (6.0 g, 1.37 mmol) was dissolved in pyridine (50 ml), methanesulfonyl chloride (3.7 ml) was added and the mixture was stirred for 6 hrs. After a completion of the reaction was confirmed by T.L.C. (dichloromethane:methanol=18:1), methanol was added and the reaction solution was concentrated under reduced pressure. The resultant syrup was extracted with dichloromethane. The dichloromethane layer was washed with 2N-HCl and water, dehydrated with anhydrous sodium sulfate, separated by filtration and washed with dichloromethane. The filtrate and washings were combined. The resultant syrup was subjected to column chromatography with an eluting solvent (ethyl acetate:hexane=3:2) to afford Compound 57 (6.7 g, 82.3%).

$C_{19}H_{31}NO_{14}S_3$ (593.4) $[α]_D$=+30.88° (c 0.926, CHCl$_3$)

IR $ν^{film}{}_{max}$cm$^{-1}$: 3700–3170 (NH), 3170–2800 (CH), 1740 (ester), 1660, 1550 (amide), 1360, 1180 (SO$_2$) 270 MHz $^1$H-NMR(CDCL$_3$) ν5.80(d, 1H, NH), 5.48(dd, 1H, $J_{6,7}$=2.20 Hz, H-7), 5.23(ddd, 1H,, $J_{7,8}$=5.49 Hz, $J_{8,9}$=8.06 Hz, H-8), 4.93(ddd, 1H, $J_{3e,4}$=4.76 Hz, H-4), 4.80(dd, 1H, $J_{9,9'}$=11.72 Hz, H-9), 4.39(dd, 1H, H-9'), 4.06(q, 1H, $J_{4,5}$=$J_{5,NH}$=$J_{5,6}$=10.26 Hz, H-5), 3.88(dd, 1H, H-6), 3.71(s, 3H, COOMe), 3.19, 3.11(2s, 6H, 2Ms), 2.78(dd, 1H, $J_{3a,3c}$=12.82 Hz, H-3e), 2.19–2.04(4s, 12H, SMe, 2OAc, NAc)

Methyl(methyl 5-acetamido-4,7,8,9-tetra-O-acetyl-3,5-dideoxy-2-thio-L-glycero-α-D-galacto-2-nonulopyranosid)onate (Compound 58)

Compound 57 (5.0 g, 1.01 mmol) was dissolved in dimethylformamide (50 ml), cesium acetate (10 g) and 18-crown-6 (4 g) were added and the mixture was stirred at 120° C. for one day. The reaction solution was filtered through Celite and the filtrate was evaporated under reduced pressure to dryness. The solid was dissolved in dimethylformamide (50 ml), methyl p-toluenesulfonate (10 g) was added and the mixture was stirred at room temperature for one day. Then pyridine (50 ml) and acetic anhydride (30 ml) were added and the mixture was stirred at room temperature overnight. After a completion of the reaction was confirmed by T.L.C. (dichloromethane:methanol=18:1), methanol was added and the reaction solution was concentrated under reduced pressure. The resultant syrup was extracted with dichloromethane. The dichloromethane layer was washed with 2N-HCl and water, dehydrated with anhydrous sodium sulfate, separated by filtration and washed with dichloroemthane. the filtrate and washings were combined. The resultant syrup was subjected to column chromatography with an eluting solvent (ethyl acetate:hexane=3:2) to afford Compound 58 (4.8 g, 91.1%).

$C_{21}H_{31}O_{14}NS$ (553.3) $[α]_D$=+0.61° (c 0.97, CHCl$_3$)

IR $ν^{film}{}_{max}$cm$^{-1}$:3700–3160 (NH) 3160–2800 (CH), 1740 (ester), 1660, 1540 (amide)

270MHz $^1$H-NMR(CDCl$_3$) δ5.50–5.38(m, 2H, H-8, NH), 5.33)dd, 1H, $J_{6,7}$=2.2 OHz, $J_{7,8}$=8.97 Hz, H-7), 4.93(ddd, 1H, $J_{3c,4}$=4.77 Hz, $J_{4,5}$=10.44 Hz, H-4), 4.60(m, 2H, H-9.9'), 4.06(q, 1H, $J_{5,NH}$=$J_{5,6}$=10.44 Hz, H-5), 3.86(dd, 1H, H-6), 3.84(s, 3H, COOMe), 2.78(dd, 1H, $J_{3a,3c}$=12.64 Hz, H-3e), 2.19–1.88 (6s, 18H, SMe, 4OAc, NAc) 2-(Trimethylsilyl)ethyl O-(methyl 5-acetamido-4,7,8,9-tetra-O-acetyl-3,5-diodeoxy-L-glycero-α-D-galacto-2-nonulopyranosylonate)-(2→3)-O-(6-O-benzoyl-β-D-galactopyranosyl)-(1→4)-2,6-di-O-benzoyl-β-D-glucopyranoside (Compound 7A)

Compound 58 (0.50 g, 0.90 mmol) and Compound 16 (0.35 g, 0.46 mmol) wer dissolved in acetonitrile (6 ml), Molecular Sieves 3A (3.0 g) was added and the mixture was stirred overnight. After cooling to −15° C., dimethyl(methylthio)sulfonium triflate(50%, 1.5 g) was added and the mixture was stirred at −15° C. for 2 days. After a completion ofthe reaction was confirmedby T.L.C. (dichloromethane:methanol=18:1), the reaction solution was filtered through Celite and the combined filtrate and washings were extracted with dichloroemthane. The dichloromethane layer was washed with sodium carbonate and water, dehydratedwith anhydrous sodium sulfate, separated by filtration and washed with dichloromethane. The filtrate and washings were combined. The resultant syrup was subjected to column chromatography with an eluting solvent (ethyl acetate:hexane=2:1) to afford Compound 7A (0.21 g, 36.9%).

$C_{64}H_{79}NO_{29}Si$ (1228.3) $[α]_D$=−11.41° c 1.060, CHCl$_3$)

IR $ν^{film}{}_{max}$cm$^{-1}$:3700–3160 (NH), 3160–2800 (CH), 1740 (ester), 1680, 1530 (amide), 860, 840 (Me$_3$Si), 710 (phenyl) 270 MHz $^1$H-NMR(CDCl$_3$)

Lac unit:β8.20–7.47(m, 15H, 3BzO), 5.33(dd, 1H, $J_{1,2}$=8.06 Hz, $J_{2,3}$=9.52 Hz, H−2), 4.85(dd, 1H, $J_{gem}$=11.91 Hz, $J_{5,6}$=2.93 Hz, H-6),4.76(d, 1H, H-1), 4.69(d, 1H, $J_{1',2'}$=7.88 Hz, H-1'), 3.68(ddd, 1H, CHCH$_2$Si), 0.98 (m,2H, CH$_2$CH$_2$Si), 0.00(s, 9H, Me$_3$Si)

Neu5Ac unit:5.57(m, 1H, H-8), 5.33(dd, 1H, $J_{6,7}$=3.11 Hz, H-7), 5.13 (ddd, 1H, $J_{3,5}$=10.44 Hz, H-4), 3.97(s, 3H, COOMe), 2.82(dd, 1H, $J_{3a,3c}$=12.64 Hz, $J_{3c,4}$=4.76 Hz, H-3e), 2.22–1.97(5s, 15 H, 4AcO, AcN)

2-(Trimethylsilyl)ethyl O-(methyl 5-acetamido-4,7,8,9-tetra-O-acetyl-3,5-diodeoxy-L-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-D-glucopyranoside (Compound 7B)

Compound 7A (0,13 g, 0.11 mmol) was dissolved in pyridine (10 ml), acetic anhydride (5 ml) was added and the mixture was stirred at room temperature overnight. After a completion of the reaction was confirmed by T.L.C. (dichloromethane:methanol=18:1), methanol was added to decompose excessive reagent and concentrated under reduced pressure. The resultant syrup was subjected to column chromatography with an eluting solvent (dichloromethane:methanol=80:1) to afford Compound 7B (0.13 g, 90.7%).

$C_{64}H_{79}NO_{29}Si$ (1354.4) $[\alpha]_D = -11.41°$ (c 1.016, $CHCl_3$)

IR $\nu^{film}_{max}cm^{-1}$:3700-3160 (NH), 3160-2800 (CH), 1740 (ester), 1680, 1530 (amide), 860, 840 ($Me_3Si$), 710 (phenyl) 270 MHz $^1H$-NMR($CDCl_3$)

Lac unit:δ8.20-7.47(m, 15H, 3BzO), 5.60(t, 1H, $J_{2,3}=J_{3,4}=9.71$ Hz, H-3), 5.34(dd, 1H, $J_{1,2}=7.88$ Hz, H-2), 5.321H, H-4'), 5.211H, J $_{1',2'}=8.06$ Hz, $J_{2',3'}=9.98$ Hz, H-2'), 5.07(d, 1H, H-1'), 4.81(d, 1H, H-1), 3.68 (ddd, 1H, $CHCH_2Si$), 0.98 (m, 2H, $CH_2CH_2Si$), 0.00 (s, 9H, $Me_3Si$)

Neu5Ac unit:5.77(m, 1H, H-8), 5.32(dd, 1H, $J_{7,8}=9.71$ Hz, H−7), 3.95 (s, 3H, COOMe), 3.74(dd, 1H, H-6), 2.74(dd, 1H, $J_{3a,3c}=12.64$ Hz, $J_{3c,4}=4.76$ Hz, H−33), 2.39-1.97(8s, 24H, 7AcO, AcN)

O-(Methyl 5-acetamido-4,7,8,9-tetra-O-acetyl-3,5-dideoxy-L-glycero-α-D-galacto-2-nonulopyranosylonate)-(2→3)-O-(2,4-di-o-acetyl-6-O-benzoyl-β-D-galactopyranosyl)-(1→4)-3-O-acetyl-2,6-di-O-benzoyl-D-glucopyranoside (Compound 7C)

Compound 7B (0.38 g, 0.28 mmol) was dissolved in dichloromethane (8 ml), boron trifluoride diethyl ether (0.3 ml) was added dropwise underice-cooling and the mixture was stirred at 0° C. for 6 hrs. After a completion of the reaction was confirmed by T.L.C. (dichloromethane:methanol =18:1), the reaction solution was extracted with dichloromethane. The dichloromethane layer was washed with successive sodium carbonate and water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=60:1) to afford Compound 7C (0.33 g, 93.8%).

$C_{59}H_{67}NO_{29}$(1254.2) $[\alpha]_D = +28.75°$ (c 1.064, $CHCl_3$)

IR $\nu^{KBr}_{max}cm^{-1}$:3700-3160(OH, NH), 3160-2800 (CH), 1750 (ester), 1670, 1540 (amide), 710 (phenyl)

O-(Methyl 5-acetamido-4,7,8,9-tetra-O-acetyl-3,5-dideoxy-L-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyltrichloroacetimidate (Compound 7D)

Compound 7C (0.30 g, 0.24 mmol) was dissolved in dichloromethane (3 ml), trichloroacetonitrile (0.9 ml) and 1,8-diazabicyclo[5.4.0]-undec-7-ene (35 mg) were added and the mixture wasstirred at 0° C. for 2 hrs. After a completion of the eaction was confirmed by T.L.C. (dichloromethane:methanol=18:1), the reaction solution was concentrated under reduced pressure. The resultant syrup was subjected to column chromatography with an eluting solvent (dichloromethane:methanol=75:1) to afford Compound 7D (0.32 g, 95.7%).

$C_{61}H_{67}N_2O_{29}Cl_3$ (1398.6) $[\alpha]_D = +24.19°$ (c 0.992, $CHCl_3$)

IR $\nu^{film}_{max}cm^{-1}$:3700-3140 (OH, NH), 3140-2800 (CH), 1750 (ester ), 1680, 1540(amide), 710 (phenyl) 270 MHz $^1H$-NMR($CDCl_3$)

Lsc unit:δ8.55(s, 1H, C=NH), 8.11-7.31(m, 15H, 3BzO), 6.64(d, 1H, $J_{1,2}=3.85$ Hz, H-1), 5.83(t, 1H, $J_{2,3}=J_{3,4}=9.70$ Hz, H−3), 5.26(dd, 1H, $J_{1,2}=3.85$ Hz, H-2), 5.19(d, 1H, H-4'), 5.10(dd, 1H, $J_{1',2'}=8.06$ Hz, $J_{2',3'}=9.89$ Hz, H-2'), 4.98(d, 1H, H-1')

Neu5Ac unit:5.61(m, 1H, $J_{8,9}=6.23$ Hz, H-8), 5.18(dd, 1H, $J_{7,8}=7.88$ Hz, H-7), 3.80(s, 3H, COOMe), 3.59(dd, 1H, $J_{5,6}=10.44$ Hz, $J_{6,7}=2.38$ Hz, H-6 ), 2.60(dd, 1H, $J_{3e,4}=5.86$ Hz, H-3e), 2.22-1.82(8s, 24H, 7AcO, AcN), 1.70(t, 1H, $J_{3a,3e}=12.36$ Hz, H−3a)

O-(Methyl 5-acetamido-4,7,8,9-tetra-O-acetyl-3,5dideoxy-L-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-benzoyl-4-octadecene-1,3-diol (Compound 7E)

Compound 7D (0.21 g, 0.15 mmol) and Compound 17 (0.15 g, 0.34 mmol) were dissolved indichloromethane (5 ml), Molecular Sieves 4A type AW 300 (3 g) was added and the mixture was stirred at room temperature for 30 minutes. then boron trifluoride diethyl ether (0.04 ml) was added dropwise under ice-cooling and the mixture was stirred at 0° C. for 4 hrs. After a completion of the reaction was confirmed by T.L.C. (dichloromethane:methanol=18:1), the reaction solution was filtered through Celite and the combined filtrate and washings were extracted with dichloromethane. The dichloromethane layer was washed with successive sodium carbonate and water, dehydrated with anhydrous sodium sulfate, separated by filtration and washed with dichloromethane. The filtrate and washings were combined. The resultant syrup was subjected to column chromatography with an eluting solvent (ethyl acetate: hexane =3 : 2) to afford Compound 7E 80.0%).

$C_{84}H_{104}N_4O_{31}$ (1665.8) $[\alpha]_D = -19.61°$ (c 1.05, $CHCl_3$)

IR $\nu^{film}_{max}cm^{-1}$:3700-3140 (NH), 3140-2800 (CH), 2100 ($N_3$), 1740 (ester), 1680, 1530 (amide), 700 (phenyl) 270 MHz $^1H$-NMR($CDCl_3$)

Lac unit: δ8.05-7.27(m, 20H, 4BzO), 5.40(t, 1HJ, H-3), 5.23(dd, 1H, $J_{1,2}=8.06Hz$, H-2), 5.16(d, 1H, H-4'), 5.08(dd, 1H, $J_{1',2'}b=8.06Hz$, $J_{2',3'}=10.71Hz$, H-2'), 4.93 (d, 1H, H-1'), 4.66(d, 1H, H-1)

Neu5Ac unit: 5.61(m, 1H, H-8), 5.17(dd, 1H, $J_{6,7}=2.20Hz$, H-7), 3.80 (s, 3H, COOMe), 3.58(dd, 1H, H-6), 2.60(dd, 1H, $J_{3a,3e}=12.82Hz$, $J_{3e,4}=4.94Hz$, H-3e), 2.21-1.73(8S, 24H, 7AcO, AcN)

Sphingosine unit:5.55(m, 1H, H-5), 5.51(dd, 1H, H-4), 1.24(s, 22H, $11CH_2$), 0.87(t, 3H, $CH_3$)

O-(Methyl
5-acetamido-4,7,8,9-tetra-O-acetyl-3,5-dideoxy-L-
glycero-α-D-galacto-2-nonulopyranosylonate)-(2→3)-
O-(2,4-di-O-acetyl-6-O-benzoyl-β-D-galac-
topyranosyl)-(1→4)-O-(3-O-acetyl-2,6-di-O-benzoyl-β-
D-glucopyranosyl)-(1→1)-
(2S,3R,4E)-3-benzoyl-2-octadecanamid-4-octadecene-
1,3-diol (Compound 7F)

Compound 7E (100 mg, 0.06 mmol) was dissolved in a mixed solvent of 5/1 pyridine/water (12 ml) and the solution was stirred at room temperature for 30 hrs. while blowing hydrogen sulfide gas. After a completion of the reaction was confirmed by T.L.C. (ethyl acetate), the reaction solution was evaporated under reduced pressure to dryness. The solid was dissolved in dichloromethane (6 ml), stearic acid 58 mg, 0.20 mmol) and WSC (58 mg) were added and the mixture was stirred at room temperature overnight. After a completion of the reaction was confirmed by T.L.C. (dichloromethane:-methanol=18:1), the reaction solution was extracted with dichloromethane. The dichloromethane layer was washed with water, dehydrated with anhydrous sodium sulfate, separated by filtration, and washed with dichloromethane. The combined filtrate and washings were concentrated under reduced pressure. The resultant syrup was subjected to column chromatography with an eluting solvent (dichloromethane:methanol=75:1) to afford Compound 7F (90 mg, 78.7%).

$C_{102}H_{140}N_2O_{32}$ (1906.2) $[\alpha]_D = -3.00°$ (c 0.80, CHCl$_3$)

IR $\nu^{film}{}_{max}$cm$^{-1}$:3700–3140 (NH), 3140–2800 (CH), 1740 (ester), 1680, 1530 (amide), 710 (Ph)

270MHz $^1$H-NMR(CDCl$_3$)

Lac unit: δ8.04–7.26(m, 20H, 4BzO), 5.37(t, 1H, H-3), 5.17(dd, 1H, $J_{2,3}$=10.63Hz, H-2), 5.16(d, 1H, H-4'), 5.06(dd, 1H, $J_{1',2'}$=7.70Hz, $J_{2',3'}$=10.25Hz, H-2'), 4.91(d, 1H, H-1'), 4.59(d, 1H, $J_{1,2}$=7.70Hz, H-1)

Neu5Ac unit: 5.60(m, 1H, H-8), 3.80(s, 3H, COOMe), 2.59(dd, 1H, $J_{3a,3e}$=12.61Hz, $J_{3e,4}$=4.48Hz, H-3), 2.21–1.84(8S, 24H, 7AcO, AcN)

Cer unit: 5.75(td, 1H, $J_{5,6'}$=6.84Hz, H-5), 1.26(s, 50H, 25CH$_2$), 0.87(t,6H, 2CH$_3$)

O-(5-Acetamido-3,5-dideoxy-L-glycero-α-D-galacto-2-nonulopyranosylonic
acid)-(2→3)-O-(β-D-galactopyranosyl)-(1→4)-O-(β-D-
glucopyranosyl)-(1→1)-(2S,3R,4E)-2-ocatadecanamid-
4-octadecene-1,3-diol (Compound 7)

Compound 7F (90 mg, 0.047 mmol) was dissolved in methanol (3 ml), 28% sodium methylate solution (5 drops) was added and the mixture was stirred at room temperature for 10 hrs. Water (0.5 ml) was added and the mixture was stirred for further 4 hrs. After a completion of the reaction was confirmed by T.L.C. (butanol:ethanol:water=4:2:1), the reaction solution was neutralized with ion exchange resin IR-120 (H$^+$) and concentrated under reduced pressure. The resultant syrup was subjected to gel filtration with Sephadex LH-20 to afford Compound 7 (54 mg, quant.).

$C_{59}H_{108}N_2O_{21}$ (1181.5) $[\alpha]_D = -0.71°$ (c 0.834, methanol:dichloromethane=1:1)

IR $\nu^{KBr}{}_{max}$cm$^{-1}$:3800–2800 (OH, NH), 2950, 2870 (Me, methylene), 1730 (C=O), 1650, 1560 (amide) 270 MHz $^1$H-NMR(CDCl$_3$)

Lac unit: δ4.25(d, 1H, $J_{1',2'}$=7.88 Hz, H-1'), 4.17(d, 1H, $J_{1,2}$=7.88 Hz, H-1)

Neu5Ac unit: 3.08(broad, 1H, H-3e), 1.86(s, 3H, AcN)

Cer unit: 5.55(td, 1H, $J_{5,6}$=$J_{5,6'}$=6.59 Hz, H-5), 4.36(dd, 1H, H-4), 1.24(s, 50H, 25CH$_2$), 0.86(t, 6H, 2CH$_3$)

EXAMPLE 8

2-(Trimethylsilyl)ethyl O-(5-acetamido-1,4,7,8,9-penta-O-acetyl-3,5-dideoxy-D-glycero-α-D-galacto-2-
nonulopyranosyl)-(2→3)-O-(2,4,6-tri-O-acetyl-β-D-
galactopyranosyl)-(1→4)-2,3,6-tri-O-acetyl-β-D-
glucopyranoside (Compound 60)

Compound 59, i.e., 2-(trimethylsilyl)ethyl O-(methyl 5-acetamido4,7,8,9-tetra-O-acetyl-3,5-dideoxy-D-glycero-α-D-galacto-2-nonulopyranosyl)-(2→3)-O-(6-O-benzoyl-β-D-galactopyranosyl)-(1→4)-2,6-di-O-benzoyl-β-D-glucopyranoside (0.25 g, 0.20 mmol) was dissolved in methanol (25 ml), sodium boron hydride (750 mg, 19.83 mmol) was added and the mixture was stirred at room temperature for 5 hrs. After a completion of the reaction wsa confirmed by T.L.C. (butanol:ethanol:water=4:2:1), acetic acid was added to decompose excessive reagent and the reaction solution was evaporated under reduced pressure to dryness. The solid was dissolved in pyridine (20 ml), acetic anhydride (15 ml) was added and the mixture was stirred at room temperature for 15 hrs. After a completion of the reaction was confirmed by T.L.C. (dichloromethane: methanol=18:1), the reaction solution was extracted with dichloromethane. The dichloromethane layer was washed with HCl and water, dehydrated with anhydrous sodium sulfate, separated by filtration and washed with dichloromethane. The combined filtrate and washings were concentrated under reduced pressure. The resultant syrup was subjected to column chromatography with an eluting solvent (dichloromethane:methanol=80:1) to afford Compound 60 (0.20 g, 83.1%).

$C_{50}H_{75}NO_{29}Si$ (1182.22)

$[\alpha]_D = +7.77°$ (c 0.926, CHCl$_3$)

IR $\nu^{film}{}_{max}$cm$^{-1}$: 3800–3160 (NH), 3160–2800 (CH), 1750 (ester), 1670, 1540 (amide), 860, 840 (Me$_3$Si)

270 MHz $^1$H-NMR(CDCl$_3$)

Lac unit: δ 5.31(dd, 1H, H-4'), 5.17(t, 1H, $J_{2,3}$=$J_{3,4}$=9.53 HZ, H-3), 5.00(dd, 1H, $J_{1',2'}$=7.70 Hz, $J_{2',3'}$=9.53 Hz, H-2'), 4.87(dd, 1H, $J_{1,2}$=8.06 Hz, H-2), 4.57(d, 1H, H-1'), 4.47(d, 1H, H-1), 4.45(dd, 1H, H-3'), 3.57(ddd, 1H, C$\underline{H}$CH$_2$Si), 0.90(m, 2H, CH$_2$C$\underline{H}_2$Si), 0.00(s, 9H, Me$_3$S$\underline{i}$)

Neu5Ac unit: 5.37(dd, 1H, $J_{6,7}$=2.20 Hz, H-7), 5.19(m, 1H, H-8), 3.86 (dd, 1H, $J_{5,6}$=10.63 Hz, H-6), 2.20–1.86(12s, 36H, 11OAc, NAc)

O-(5-Acetamido-1,4,7,8,9-penta-O-acetyl-3,5-dideoxy-
D-glycero-α-D-galacto-2-nonulopyranosyl)-(2→3)-O-
(2,4,6-tri-O-acetyl-β-D-galactopyranosyl)-(1→4)-2,3,6-
tri-O-acetyl-D-glucopyranoside (Compound 61)

Compound 60 (0.18 g, 0.15 mmol) was dissolved in dichloromethane (5 ml), boron trifluoride diethyl ether (0.2 ml) was added dropwise under ice-cooling and the mixture was stirred at 0° C. for 6 hrs. After a completion of the reaction was confirmed by T.L.C. (dichloromethane:methanol=15:1), the reaction solution was extracted with dichloromethane. The dichloromethane layer was washed with successive sodium sulfate, separated by filtration and washed with dichloromethane. The combined filtrate and washings were concentrated under reduced pressure. The resultant syrup was subjected to column chromatography with an eluting solvent (dichloromethane:methanol=40:1) to afford Compound 61 (0.12 g, 72.9%).

C$_{45}$H$_{63}$NO$_{29}$ (1081.98)

[α]$_D$=+50.81° (c 1.972, CHCl$_3$)

IR ν$^{film}_{max}$cm$^{-1}$: 3700–3160 (OH, NH), 3160–2800 (CH), 1730 (ester), 1650, 1530 (amide)

O-(5-Acetamido-1,4,7,8,9-penta-O-acetyl-3,5-dideoxy-D-glycero-α-D-galacto-2-nonulopyranosyl)-(2→3)-O-(2,4,6-tri-O-acetyl-β-D-galactopyranosyl)-(1→4)-2,3,6-tri-O-acetyl-α-D-glucopyranosyltrichloroacetimidate (Compound 62)

Compound 61 (90.0 mg, 0.08 mmol) was dissolved in dichloromethane (1.5 ml), trichloroacetonitrile (0.3 ml) and 1,8-diazabicyclo[5.4.0]-undec-7-ene (10 mg) were added and the mixture was stirred at 0° C. for 2 hrs. After a completion of the reaction was confirmed by T.L.C. (dichloromethane:methanol=15:1) the reaction solution was concentrated under reduced pressure. The resultant syrup was subjected to column chromatography with an eluting solvent (dichloromethane:methanol=55:1) to afford Compound 62 (83.0 mg, 81.2%).

C$_{47}$H$_{63}$N$_2$O$_{29}$Cl$_3$ (1226.37)

[α]$_D$=+54.96° (c 1.288, CHCl$_3$)

IR ν$^{film}_{max}$cm$^{-1}$: 3700–3170 (NH), 3170–2800 (CH), 1730 (ester), 1660, 1520 (amide)

270 MHz $^1$H-NMR(CDCl$_3$)

Lac unit: δ 8.66(s, 1H, C=NH), 6.48(d, 1H, J$_{1,2}$=3.66 Hz, H-1), 5.55(t, 1H, J$_{2,3}$=J$_{3,4}$=9.52 Hz, H-3), 5.32(dd, 1H, H-4'), 5.03(dd, 1H, J$_{1',2'}$=8.06 Hz, J$_{2',3'}$=10.25 Hz, H-2'), 4.90(dd, 1H, H-2), 4.60(d, 1H, H-1')

Neu5Ac unit: 5.62(d, 1H, J$_{5,NH}$=9.90 Hz, NH), 5.38(dd, 1H, H-7), 5.25 (m, 1H, H-8), 2.21–1.87(12s, 36H, 11AcO, AcN)

O-(5-Acetamido-1,4,7,8,9-penta-O-acetyl-3,5-dideoxy-D-glycero-α-D-galacto-2-nonulopyranosyl)-(2→3)-O-(2,4,6-tri-O-acetyl-β-D-galactopyranosyl)-(1→4)-O-(2,3,6-tri-O-acetyl-β-D-glucopyranosyl)-(1→1)-(2S,3R,4E)-2-azido-3-benzoyl-4-octadecene-1,3-diol (Compound 63)

Compound 62 (32.5 mg, 0.03 mmol) and Compound 17 (23.0 mg, 0.05 mmol) were dissolved in dichloromethane (2 ml), Molecular Sieves 4A type AW 300 (2 g) was added and the mixture was stirred at room temperature for 30 minutes. Then boron trifluoride diethyl ether (0.04 ml) was added dropwise under ice-cooling and the mixture was stirred at 0° C. for 4 hrs. After a completion of the reaction was confirmed by T.L.C. (dichloromethane:methanol=18:1), the reaction solution was filtered through Celite and the combined filtrate and washings were extracted with dichloromethane. The dichloromethane layer was washed with successive sodium carbonate and water, dehydrated with anhydrous sodium sulfate, separated by filtration and washed with dichloromethane. The filtrate and washings were combined. The resultant syrup was subjected to column chromatography with an eluting solvent (dichloromethane:methanol=60:1) to afford Compound 63 (25.4 g, 64.2%).

C$_{70}$H$_{100}$N$_4$O$_{31}$ (1493.57)

[α]$_D$=+11.11° (c 0.225, CHCl$_3$)

IR ν$^{film}_{max}$cm$^{-1}$: 3700–3140 (NH), 3140–2800 (CH), 2100 (N$_3$), 1730 (ester), 1670, 1520 (amide), 710 (phenyl)

270 MHz $^1$H-NMR(CDCl$_3$)

Lac unit; δ 5.31(dd, 1H, H-4'), 5.18(t, 1H, J$_{2,3}$=J$_{3,4}$=9.16 Hz, H-3), 5.00(dd, 1H, J$_{1',2'}$=8.06 Hz, J$_{2',3'}$=9.90 Hz, H-2'), 4.92(dd, 1H, J$_{1,2}$=7.70 Hz, H-2), 4.58(d, 1H, H-1'), 4.51(d, 1H, H-1), 4.45(dd, 1H, H-3')

Neu5Ac unit: 5.45 (d, 1H, J$_{5,NH}$=9.53 Hz, NH), 5.37(dd, 1H, J$_{6,7}$=2.20 Hz, H-7), 5.19(m, 1H, H-8), 2.19–1.87(12s, 36H, 11AcO, AcN)

Sphingosine unit: 8.06–7.42(m, 5H, OBz), 5.92(m, 1H, J$_{5,6}$=J$_{5,6'}$=6.59 Hz, H-5), 1.24(s, 22H, 11CH$_2$), 0.87(t, 3H, CH$_3$)

O-(5-Acetamido-1,4,7,8,9-penta-O-acetyl-3,5-dideoxy-D-glycero-α-D-galacto-2-nonulopyranosyl)-(2→3)-O-(2,4,6-tri-O-acetyl-β-D-galactopyranosyl)-(1→4)-O-(2,3,6-tri-O-acetyl-β-D-glucopyranosyl)-(1→1)-(2S,3R,4E)-3-benzoyl-2-octadecanamid-4-octadecene-1,3-diol (Compound 64)

Compound 63 (19.5 mg, 0.01 mmol) was dissolved in a mixed solvent of 5/1 pyridine/water (3.6 ml) and the solution was stirred at room temperature for 30 hrs. while blowing hydrogen sulfide gas. After a completion of the reaction was confirmed by T.L.C. (ethyl acetate), the reaction solution was evaporated under reduced pressure to dryness. The solid was dissolved in dichloromethane (6 ml), stearic acid (20 mg, 0.07 mmol) was WSC (20 mg) were added and the mixture was stirred at room temperature overnight. After a completion of the reaction was confirmed by T.L.C. (dichloromethane:methanol=18:1), the reaction solution was subjected to column chromatography with an eluting solvent (dichloromethane:methanol=65:1) to afford Compound 64 (19.0 mg, 84.1%).

C$_{88}$H$_{135}$N$_2$O$_{32}$ (1733.03)

[α]$_D$=+23.15° (c 0.380, CHCl$_3$)

IR ν$^{film}_{max}$cm$^{-1}$: 3700–3170 (NH), 3170–2800 (CH), 1760 (ester), 1670, 1550 (amide), 720 (phenyl) 270 MHz $^1$H-NMR(CDCl$_3$)

Lac unit: δ5.31(dd, 1H, H-4'), 5.16(t, 1H, J$_{2,3}$=J$_{3,4}$=9.16 Hz, H-3), 4.98(dd, 1H, J$_{1',2'}$=7.69 Hz, J$_{2',3'}$=10.26 Hz, H-2'), 4.89(dd, 1H, J$_{1,2}$=8.06 Hz, H-2), 4.54(d, 1H, H-1'), 4.45(d, 1H, H-1), 4.36(dd, 1H, H-3')

Neu5Ac unit: 5.56(d, 1H, J$_{5,NH}$=9.89 Hz, NH), 5.36(dd, 1H, H-7), 5.18 (m, 1H, H-8), 3.86(dd, 1H, J$_{6,7}$=2.20 Hz, H-6), 2.17–1.87(12s, 36H, 11AcO, AcN)

Cer unit: 8.02–7.41(m, 5H, 0 Bz), 5.84(td, 1H, J$_{5,6}$=J$_{5,6'}$=6.60 Hz, H-5), 1.25(s, 50H, 25CH$_2$), 0.88(t, 6H, 2CH$_3$)

O-(5-Acetamido-3,5-dideoxy-D-glycero-α-D-galacto-2-nonulopyranosyl)-(2→3)-O-(β-D-galactopyranosyl)-(1→4)-O-(β-D-glucopyranosyl)-(1→1)-(2S,3R,4E)-2-octadecanamid-4-octadecene-1,3-diol (Compound 8)

Compound 64 ((18.5 mg, 0.047 mmol) was dissolved in methanol (1 ml), 28% sodium methylate solution (5 drops) was added and the mixture was stirred at room temperature for 8 hrs. Water (0.5 ml) was added and the mixture was stirred for further 10 hrs. After a completion of the reaction was confirmed by T.L.C. (butanol:ethanol:water=4:2:1), the reaction solution was neutralized with ion exchange resin IR-120 (H+), filtered and concentrated under reduced pressure. The resultant syrup was subjected to gel filtration with Sephadex LH-20 to afford Compound 8 (13 mg, quant.).

C$_{59}$H$_{110}$N$_2$O$_{20}$ (1167.52) [α]$_D$=0.00° (c 0.284, methanol:dichloromethane=1:1)

IR ν$^{KBr}_{max}$cm$^{-1}$: 3700–2800 (OH, NH), 2930, 2850 (Me, methylene), 1720 (C=O), 1640, 1550 (amide) 270 MHz $^1$H-NMR(CDCl$_3$)

Lac unit: δ4.43(d, 1H, $J_{1',2'}$=7.69 Hz, H-1'), 4.30(d, 1H, $J_{1,2}$=7.69 Hz, H-1), 4.19(dd, 1H, $J_{2',3'}$=9.52 Hz, $J_{3',4'}$=3.66 Hz, H-3')

Neu5Ac unit: 2.00(s, 3H, AcN)

Cer unit: 5.69(td, 1H, $J_{5,6}=J_{5,6'}$=6.59 Hz, H-5), 5.45(dd, 1H, $J_{4,5}$=7.32 Hz, H-4), 1.28(s, 50H, 25CH$_2$), 0.89(t, 6H, 2CH$_3$)

What is claimed is:

1. A ganglioside GM$_3$ analog represented by the formula

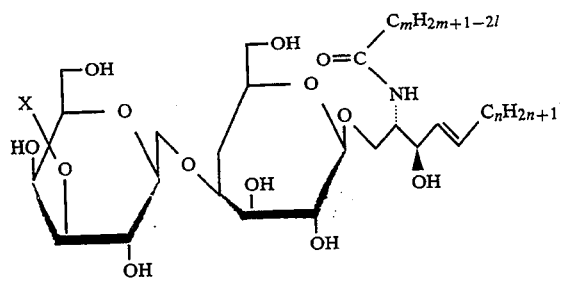

in which X represents a radical having a formula selected from the group consisting of the following formula

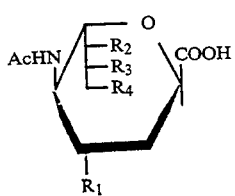

wherein at least one of $R_1$, $R_2$, $R_3$, and $R_4$ is hydrogen and the remainder is hydroxyl;

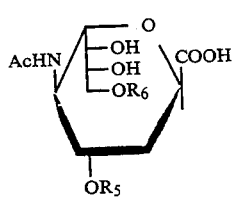

wherein at least one of $R_5$ and $R_6$ is hydrogen and the remainder is methyl; and

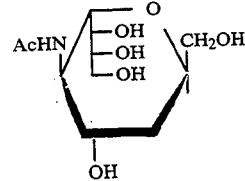

wherein m is an integer of 15 to 25, l is an integer of 0 to 3, n is an integer of 11 to 15 and Ac represents acetyl.

2. A ganglioside GM$_3$ analog of claim 1 wherein m is 15-25, straight chain, l is 0-3 and n is 13 or 15, straight chain.

3. A ganglioside GM$_3$ analog of claim 1 wherein X represents a radical having a formula selected from the group consisting of the following formulae

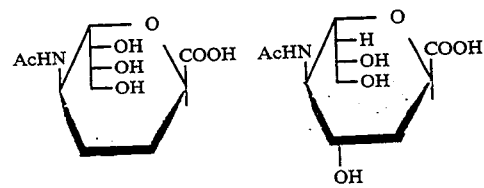

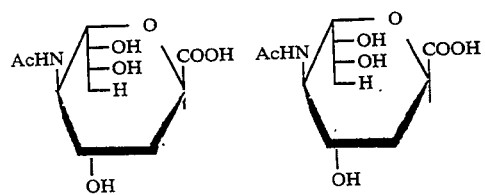

wherein Ac represents acetyl; m is 17, l is 0 and n is 13.

* * * * *

UNITED STATES PATENT AND TRADEMARK OFFICE
CERTIFICATE OF CORRECTION

PATENT NO. : 5,380,832
DATED : January 10, 1995
INVENTOR(S) : Akira HASEGAWA, et al.

It is certified that error appears in the above-indentified patent and that said Letters Patent is hereby corrected as shown below:

On the title page, Item [75], the inventorship should read:

--Akira Hasegawa; Makoto Kiso, both of Gifu, Japan--

Signed and Sealed this

Sixteenth Day of May, 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,380,832
DATED : January 10, 1995
INVENTOR(S) : Akira Hasegawa et al.

It is certified that error appears in the above-indentified patent and that said Letters Patent is hereby corrected as shown below:

Column 65:
    Claim 1, lines 27 and 28, "formula" should read
        --formulae--.

Column 66:
    Claim 3, line 30, first of the two formulas:

" 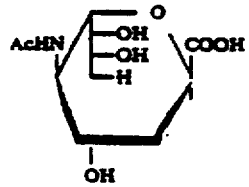 "

should read:

-- 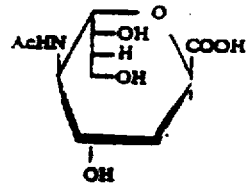 --

Signed and Sealed this

Tenth Day of September, 1996

Attest:

BRUCE LEHMAN

Attesting Officer      Commissioner of Patents and Trademarks